(12) United States Patent
Hiramoto et al.

(10) Patent No.: US 9,358,191 B2
(45) Date of Patent: Jun. 7, 2016

(54) DEODORANT COMPOSITION

(71) Applicant: TAKASAGO INTERNATIONAL CORPORATION, Tokyo (JP)

(72) Inventors: Tadahiro Hiramoto, Hiratsuka (JP); Ryo Takeuchi, Hiratsuka (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/293,681

(22) Filed: Jun. 2, 2014

(65) Prior Publication Data
US 2014/0271522 A1    Sep. 18, 2014

Related U.S. Application Data

(62) Division of application No. 12/252,558, filed on Oct. 16, 2008, now Pat. No. 8,778,320, which is a division of application No. 10/532,976, filed as application No. PCT/JP03/13794 on Oct. 28, 2003, now abandoned.

(30) Foreign Application Priority Data

Oct. 28, 2002 (JP) .................. 2002-312981
Oct. 28, 2002 (JP) .................. 2002-312982
Oct. 9, 2003 (JP) .................. 2003-351216

(51) Int. Cl.
*A61K 8/34* (2006.01)
*A61K 8/44* (2006.01)
(Continued)

(52) U.S. Cl.
CPC . *A61K 8/347* (2013.01); *A61K 8/44* (2013.01); *A61K 8/97* (2013.01); *A61L 9/01* (2013.01);
(Continued)

(58) Field of Classification Search
None
See application file for complete search history.

(56) References Cited

U.S. PATENT DOCUMENTS 2,226,177 A    12/1940    Orelup et al.
2,875,769 A     3/1959    Rosmarin et al.
(Continued)

FOREIGN PATENT DOCUMENTS

JP    60-153778       8/1985
JP    63-270648 A    11/1988
(Continued)

OTHER PUBLICATIONS

XP-002390750 (1968)—Hans Beyer "Lehrbuch der organischen Chemie", pp. 430-438.
(Continued)

*Primary Examiner* — Bethany Barham
*Assistant Examiner* — Barbara Frazier
(74) *Attorney, Agent, or Firm* — Sughrue Mion, PLLC

(57) ABSTRACT

It is intended to provide a novel deodorant composition which is excellent in the deodorizing effect, is capable of affording a deodorant composition by a convenient method, and shows no decrease in the deodorizing performance even after a long period of time, once the deodorant being prepared. Specifically, there is provided a deodorant composition containing, as the active component, a colored compound obtainable by reacting a polyphenol in a solvent showing alkalinity in the coexistence of an oxygen molecule at a reaction pH value of 6.5 or more. As a substitute for a polyphenol, use can be made of a plant extract containing a polyphenol but containing substantially no amino acid. It is also possible to further employ an amino acid. Furthermore, use can be made of a plant extract and/or a plant body containing a polyphenol and an amino acid.

4 Claims, 1 Drawing Sheet

(51) Int. Cl.

| | | |
|---|---|---|
| *A61K 8/97* | (2006.01) | |
| *A61L 9/01* | (2006.01) | |
| *A61L 9/013* | (2006.01) | |
| *A61Q 5/02* | (2006.01) | |
| *A61Q 15/00* | (2006.01) | |
| *C11D 3/00* | (2006.01) | |
| *C11D 3/40* | (2006.01) | |
| *A61Q 11/00* | (2006.01) | |

(52) U.S. Cl.
CPC . *A61L 9/013* (2013.01); *A61Q 5/02* (2013.01); *A61Q 11/00* (2013.01); *A61Q 15/00* (2013.01); *C11D 3/0068* (2013.01); *C11D 3/40* (2013.01)

(56) References Cited

U.S. PATENT DOCUMENTS

| | | |
|---|---|---|
| 6,190,891 B1 | 2/2001 | Echigo et al. |
| 6,294,161 B1 | 9/2001 | Hiramoto et al. |
| 2003/0041391 A1 | 3/2003 | Rozzell et al. |

FOREIGN PATENT DOCUMENTS

| | | |
|---|---|---|
| JP | 64-016713 | 1/1989 |
| JP | 9-38183 | 2/1997 |
| JP | 10-212221 | 8/1998 |
| JP | 10-262690 | 10/1998 |
| JP | 11-31 9051 | 11/1999 |
| JP | 2000-135277 A | 5/2000 |
| JP | 2003-102821 | 4/2003 |

OTHER PUBLICATIONS

Yabuta, et al., "Structure of Green Pigment Formed by the Reaction of Caffeic Acid Esters (or Chlorogenic acid) with a Primary Amino Compound", Biosci. Biotechnol. Biochem., vol. 65 No. 10 (2001), pp. 2121-2130.

Negishi, et al. "Enzymatic Deodorization with Variegatic Acid from Boletus subvelutipes and Its Mechanism", Food Sci. Technol. Res., vol. 6, No. 3, (2000), pp. 186-191.

European Patent Office, Office Action issued in European Application No. 03759009.8, dated Oct. 16, 2008.

European Patent Office, Office Action issued in European Application No. 03759009.8, dated Nov. 25, 2010.

European Patent Office, Office Action dated Feb. 14, 2013, issued in European Patent Application No. 03 759 009.8.

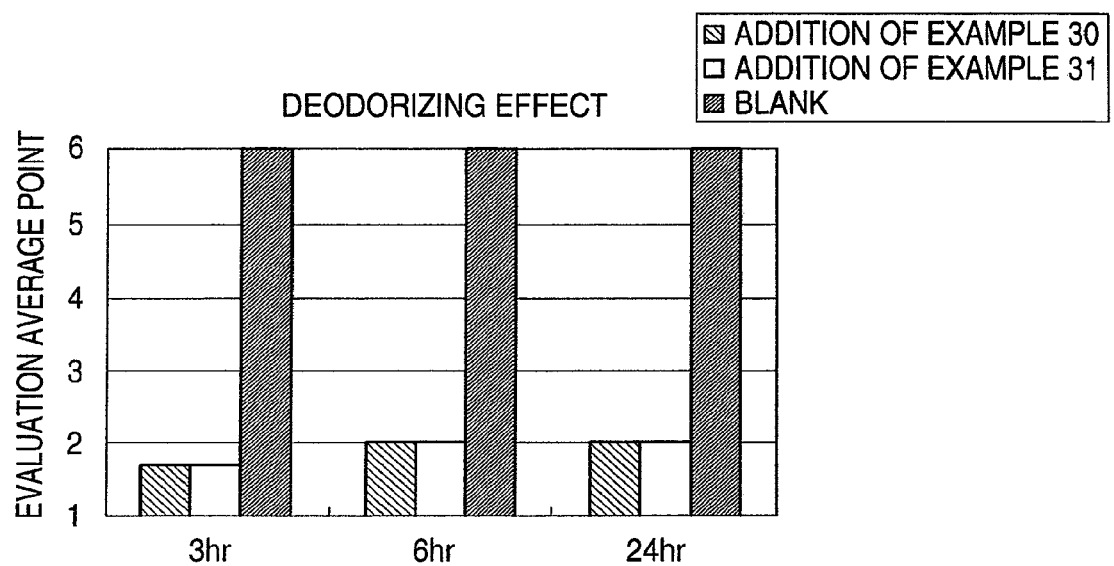
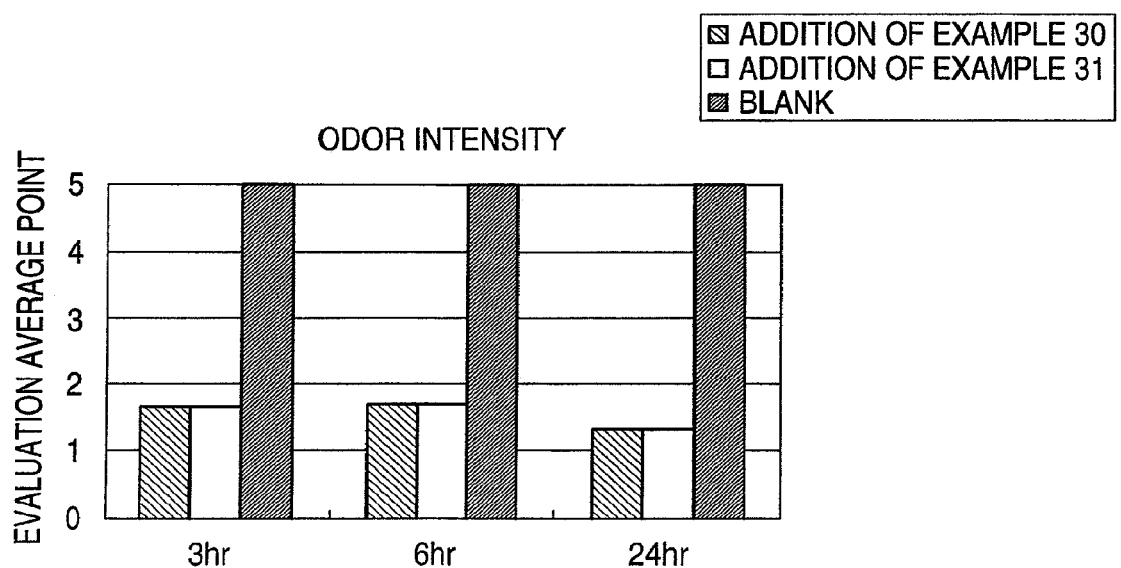

DEODORANT COMPOSITION

CROSS REFERENCE TO RELATED APPLICATIONS

This is a Divisional of U.S. application Ser. No. 12/252,558, filed Oct. 16, 2008, which is a Divisional of U.S. application Ser. No. 10/532,976 filed Apr. 28, 2005, now abandoned, which is a 371 of PCT International Application No. PCT/JP2003/013794 filed Oct. 28, 2003, claiming priority of JP 2002-312981, filed Oct. 28, 2002, JP 2002-312982 filed Oct. 28, 2002, and JP 2003-351216 filed Oct. 9, 2003, all of the above-noted applications are incorporated herein by reference in their entirety.

TECHNICAL FIELD

The present invention relates to a novel deodorant composition. Specifically, it relates to a novel deodorant composition comprising a colored compound obtainable by reacting a polyphenol in a solvent showing alkalinity in the coexistence of oxygen molecules at a reaction pH value of 6.5 or more. Precisely, it relates to a novel deodorant composition comprising a colored compound obtainable by reacting a specific polyphenol in a solvent showing alkalinity in the coexistence of oxygen molecules at a reaction pH value of 6.5 or more and to a novel deodorant composition comprising a colored compound obtainable by reacting a specific polyphenol and an amino acid in a solvent showing alkalinity in the coexistence of oxygen molecules at a reaction pH value of 6.5 or more. More precisely, it relates to a novel deodorant composition to be used for elimination or reduction of odors felt in daily life, such as bad breath (halitosis), body odor, odor in refrigerator, odor of raw garbage, odor of footwear cupboard, body odor of human and animals, odor of feces and urine of human and animals, odors in factories and industrial wastes.

BACKGROUND ART

Recently, with diversification of lives, improvement of life level, changes and improvement of attitudes, and the like, attention has been paid to various points around one's life. One of them is existence of various malodors. Main malodorous components to be targeted include nitrogenous compounds such as ammonia, urea, indole, skatole, and amines; sulfur compounds such as methyl mercaptan, hydrogen sulfide, and dimethyl sulfide; and lower fatty acids such as butyric acid. Heretofore, there are a number of reports on deodorants that are used to eliminate or reduce the malodors.

For example, JP-A-11-319051 discloses a deodorant containing a polyphenol component extracted from apple as an active component. However, the deodorant is insufficient in the deodorizing effect. Moreover, a deodorant composition containing a plant extract and a phenol oxidase as components is also known (cf. e.g., JP-A-9-38183, JP-A-10-212221, and so forth). However, although these deodorants are excellent in the deodorizing effect, they have a problem that preparation processes thereof are rather complicated.

On the other hand, there is a report in Food. Sci. Technol. Res., 6(3), 186-191, 2000 that the deodorizing effect of a specific polyphenol is confirmed in an $NH_4OH$ solution or in an $NaHCO_3$ solution. Moreover, in Biosci. Biotechnol. Biochem., 65(10), 2121-2130, 2001, there is a report that a colored compound can be prepared by reacting a caffeic acid ester and an amino acid.

As the deodorant composition, there is desired a deodorant composition capable of maintaining a deodorizing ability for a long period of time as far as possible. Moreover, a deodorant composition having an excellent deodorizing effect on various malodorous components such as nitrogenous compounds, sulfur compounds, and lower fatty acids is expected.

DISCLOSURE OF THE INVENTION

An object of the invention is to provide a novel deodorant composition which is excellent in the deodorizing effect and obtainable by a simple process. Moreover, it is to provide a novel deodorant composition which shows no decrease in the deodorizing performance even after a long period of time, once the deodorant being prepared. Furthermore, it is to provide a deodorant composition having an excellent deodorizing effect on a wide range of malodorous components.

As a result of the extensive studies for solving the above problems, the present inventors have found that a colored compound obtainable by reacting a specific polyphenol in a solvent showing alkalinity in the coexistence of an oxygen molecule at a reaction pH value of 6.5 or more has an excellent deodorizing effect. Also, they have found that a colored compound obtainable by reacting a specific polyphenol and an amino acid in a solvent showing alkalinity in the coexistence of an oxygen molecule at a reaction pH value of 6.5 or more has an excellent deodorizing effect. Furthermore, even when a composition containing the deodorizing component is stored for a long period of time, the deodorizing effect of the deodorant composition is maintained for a long time. As a result of further studies, they have finally reached the present invention.

Namely, the invention is as follows.

(1) A deodorant composition comprising, as an active component, a colored compound obtainable by reacting a polyphenol in a solvent showing alkalinity in the coexistence of oxygen molecules at a reaction pH value of 6.5 or more.

(2) The deodorant composition according to (1), wherein an oxygen molecule supply during the reaction is 1 mg/L or more.

(3) The deodorant composition according to (1) or (2), wherein the reaction temperature is in the range of 0 to 60° C.

(4) The deodorant composition according to any one of (1) to (3), wherein a metal ion is further added to the reaction system and the reaction is carried out.

(5) The deodorant composition according to any one of (1) to (4), wherein the polyphenol is a polyphenol having an o-diphenol structure.

(6) The deodorant composition according to any one of (1) to (4), wherein the polyphenol is hydroquinone.

(7) A deodorant composition comprising, as an active component, a colored compound obtainable by reacting a plant extract containing a polyphenol but containing substantially no amino acid in a solvent showing alkalinity in the coexistence of oxygen molecules at a reaction pH value of 6.5 or more.

(8) The deodorant composition according to any one of (1) to (7), wherein an amino acid is further added to the reaction system and the reaction is carried out.

(9) The deodorant composition according to (8), wherein the amino acid is an α-amino acid.

(10) A deodorant composition comprising, as an active component, a colored compound obtainable by reacting a plant extract and/or a plant body containing a polyphenol and an amino acid in a solvent showing alkalinity in the coexistence of oxygen molecules at a reaction pH value of 6.5 or more.

BEST MODE FOR CARRYING OUT THE INVENTION

The following will describe the present invention in detail.

In the invention, a polyphenol is reacted in a solvent showing alkalinity in the coexistence of oxygen molecules at a reaction pH value of 6.5 or more to obtain a deodorant composition.

First, the following will describe a polyphenol which is a raw material for preparing the deodorant composition of the invention. The polyphenol to be used in the invention means a compound having two or more phenolic hydroxyl groups in one molecule and a glycoside thereof is also included in the polyphenol. The polyphenol to be used in the invention is not particularly limited as far as it is a polyphenol capable of achieving the desired object.

Specific examples of the polyphenol include apigenin, apigenin glycosides, acacetin, isorhamnetin, isorhamnetin glycosides, isoquercitrin, epicatechin, epicatechin gallate, epigallocatechin, epigallocatechin gallate, aesculetin, ethyl protocatechuate salt, ellagic acid, catechol, γ-acid, catechin, gardenin, gallocatechin, caffeic acid, caffeic esters, chlorogenic acid, kaempferol, kaempferol glycosides, quercetin, quercetin glycosides, quercetagenin, genistin, genistin glycoside, gossypetin, gossypetin glycosides, gossypol, 4-dihydroxyanthraquinone, 1,4-dihydroxynaphthalene, cyanidin, cyanidin glycosides, sinensetin, diosmetin, diosmetin glycosides, 3,4'-diphenyldiol, sinapic acid, stearyl-β-(3,5-di-tert-butyl-4-hydroxyphenyl)propionate, spinacene, tangeritin, taxifolin, tannic acid, daphnetin, tyrosine, delphinidin, delphinidin glycosides, theaflavine, theaflavine monogallate, theaflavine bisgallate, tricetinidin, dopa, dopamine, naringenin, naringin, nordihydroguairetic acid, noradrenaline, hydroquinone, vanillin, patchouletin, herbacetin, vanillyl alcohol, vanitrope, vanillin propylene glycol acetal, vanillic acid, bis(4-hydroxyphenyl)sulfonic acid, bisphenol A, pyrocatechol, vitexin, 4,4'-biphenyldiol, 4-tert-butylcatechol, 2-tert-butylhydroquinone, protocatechuic acid, phloroglucinol, phenolic resins, procyanidin, prodelphinidin, phloretin, phloretin glycosides, fisetin, folin, fervasetin, fraxetin, phloridzin, paeonidin, paeonidin glycosides, pelargonidin, pelagugonidin glycosides, petunidin, petunidin glycosides, hesperetin, hesperidin, gallic acid, gallic esters (lauryl gallate, propyl gallate, butyl gallate), manjiferin, malvidin, malvidin glycosides, myricetin, myricetin glycosides, 2,2'-methylenebis(4-methyl-6-tert-butylphenol), 2,2'-methylenebis(4-ethyl-6-tert-butylphenol), 2,2'-methylenebis(4-methyl-6-tert-butylphenol), 2,2'-methylenebis(4-ethyl-6-tert-butylphenol), methyl atrarate, 4-methylcatechol, 5-methylcatechol, 4-methoxycatechol, 5-methoxycatechol, methylcatechol-4-carboxylic acid, 2-methylresorcinol, 5-methylresorcinol, morin, limocitrin, limocitrin glycosides, limocitrol, luteolin, luteolin glycosides, luteolinidin, luteolinidin glycosides, rutin, resorcin, resveratrol, resorcinol, leukocyanidin, leukodelphinidin, and the like.

Of these polyphenols, preferred are flavonoids such as quercetin, epicatechin, and epigallocatechin and glycosides thereof; polyphenols having an o-diphenol structure, such as gallic acid, gallic esters, chlorogenic acid, caffeic acid, caffeic esters, tannic acid, pyrocatechol, nordihydroguairetic acid, L-dopa, 4-methylcatechol, 5-methylcatechol, 4-methoxycatechol, and 5-methoxycatechol; and hydroquinone. Particularly preferred are hydroquinone and the polyphenols having an o-diphenol structure. In this connection, the o-diphenol structure means a structure wherein two hydroxyl groups are directly substituted on a benzene ring and the hydroxyl groups are adjacent to each other.

These polyphenols may be used solely or as a mixture of two or more of them.

The above polyphenols can be prepared by known methods but commercially available products may be purchased. Moreover, they may be prepared by synthesis. Furthermore, highly concentrated polyphenol fractions prepared from plants can be employed.

In the invention, instead of the above polyphenols, a plant extract can be also employed. The plant extract in this case is preferably a plant extract containing a polyphenol but containing substantially no amino acid. As the plant extract, one prepared by a known method may be used and a commercially available one may be used.

A polyphenol compound and a polyphenol-containing plant extract containing substantially no amino acid may be used in combination.

Moreover, in the invention, a deodorant composition can be also obtained by reacting a polyphenol and an amino acid in an alkaline solvent in the coexistence of oxygen molecules at a reaction pH value of 6.5 or more.

The amino acid usable in the invention is not particularly limited as far as it is an amino acid capable of resulting in the desired effect but, of amino acids, α-amino acids are particularly preferred. The α-amino acid herein means an amino acid wherein one amino group and one carboxyl group are bonded to one identical carbon atom. Examples of the α-amino acid include glycine, alanine, valine, leucine, isoleucine, glutamic acid, aspartic acid, glutamine, asparagine, serine, threonine, lysine, hydroxylysine, arginine, histidine, cystine, methionine, phenylalanine, tyrosine, tryptophan, proline, 4-hydroxyproline, cysteine, theanine, amino acid salts (sodium glutamate, sodium aspartate), and the like.

Of these, particularly, glycine, alanine, glutamic acid, aspartic acid, lysine, arginine, histidine, serine, cystine, methionine, cysteine, sodium glutamate, sodium aspartate, and tyrosine are preferred.

These amino acids can be easily available by purchasing commercially available products. Moreover, these amino acids may be used solely or as a mixture of two or more of them. Furthermore, a plant extract containing an amino acid can be also employed.

In addition, the deodorant composition of the invention can be also obtained by employing a plant extract containing substantially no polyphenol and containing an amino acid instead of an amino acid and a polyphenol in combination. The "plant extract containing substantially no polyphenol and containing an amino acid" herein can be prepared by a known method but a commercially available product can be purchased. In this connection, it is also possible to use an amino acid and an amino acid-containing plant extract containing substantially no polyphenol in combination.

At obtaining the deodorant composition in the invention, examples of using a polyphenol and an amino acid in combination also include an example of using an amino acid-containing plant extract containing substantially no polyphenol and a polyphenol in combination, an example of using a polyphenol-containing plant extract containing substantially no amino acid and an amino acid in combination, and an example of using a polyphenol-containing plant extract containing substantially no amino acid and an amino acid-containing plant extract containing substantially no polyphenol in combination.

The mixing ratio of the polyphenol to the amino acid in the deodorant composition can not be prescribed unconditionally since the ratio varies depending on the polyphenol to the amino acid to be adopted but the polyphenol and the amino acid are preferably mixed in a ratio of 9:1 to 1:9, more preferably in a ratio of 3:1 to 1:3 by mol. In this connection, the prescription is determined for the purpose of effectively utilizing the polyphenol and the amino acid in the case that they are used as raw materials, and the case that either of both substances is present in excess is not excluded.

The deodorant composition of the invention can be prepared by reacting a polyphenol or a polyphenol and an amino acid in a solvent showing alkalinity in the coexistence of oxygen molecules at a reaction pH value of 6.5 or more.

The solvent showing alkalinity is a known one and is representatively an alkaline substance-containing solvent wherein an alkaline substance is dissolved in a solvent such as water.

The alkaline substance is not particularly limited and specifically includes carbonate salts or hydrogen carbonate salts such as sodium carbonate, potassium carbonate, sodium bicarbonate, ammonium carbonate, and guanidine carbonate; borate salts such as potassium borate and sodium borate; silicate salts such as potassium silicate, sodium silicate No. 1, sodium silicate No. 2, sodium silicate No. 3, sodium orthosilicate, and sodium metasilicate; sodium monohydrogen phosphate, sodium sulfite, sodium hydroxide, calcium hydroxide, potassium hydroxide, magnesium hydroxide, ammonium hydroxide, sodium pyrophosphate, and potassium pyrophosphate; and the like.

The solvent for dissolving one or two or more these alkaline substances includes water and various hydrous solvent as preferable solvents. Moreover, so-called alkaline buffer solutions using these alkaline substances and acids may be also employed.

The above solvent usually show alkalinity and it is alkaline before the reaction but sometimes shows weak acidity depending on the substance to be incorporated into the solvent and an added amount thereof. Namely, when the solvent before the reaction is necessarily alkaline and, at obtaining the above deodorant composition, the pH of the solvent in the reaction system after the start of the reaction is 6.5 or more, then a preferable result is obtained. In particular, the pH of the reaction system is preferably in the range of 7 to 13, further preferably in the range of 8 to 13. When the pH in the reaction system during the reaction is below 6.5, it is impossible to afford a deodorant composition having a preferable deodorizing effect.

In the invention, it is necessary to react the polyphenol in the coexistence of oxygen molecules. As a conventional means for supplying oxygen molecules into the reaction system, there may be mentioned supply of oxygen or air into the system utilizing an air pump (bubbling) or active stirring of the system. The reaction in the coexistence of oxygen molecules means a reaction aiming at the acceleration of the reaction of the polyphenol present in the reaction system by actively incorporating oxygen molecules into the reaction liquid. In this case, the deodorant composition can be efficiently obtained by making the oxygen supplying amount into the reaction liquid 1 mg/L or more, preferably 2 mg/L or more. The oxygen supplying amount can be achieved by, for example, actively blowing oxygen gas, air, or a mixture thereof into the reaction system (bubbling) or it can be also achieved by stirring the reaction liquid under a reaction condition that oxygen gas or air can constantly come into contact therewith.

With regard to the temperature at the reaction, the inventive product can be obtained at a temperature of 0° C. to a reflux temperature of the solvent but in order to avoid thermal decomposition of the resulting deodorizing active component, the reaction is carried out at a temperature of preferably 0° C. to 60° C., more preferably 0° C. to 40° C., further preferably 0° C. to 25° C.

In the invention, the polyphenol reacts within a short period of time but from a practical viewpoint, the reaction may be carried out for preferably from several minutes (2 minutes) to about 24 hours, more preferably from about 10 minutes to about 9 hours, further preferably from 10 minutes to 7 hours. At the reaction for preparing the above deodorant composition, pressurization is not particularly necessary but pressure may be applied.

Moreover, when the reaction is carried out in the coexistence of a metal ion or a metal salt which releases a metal ion into the reaction system, a more excellent deodorant composition exhibiting an enhanced deodorizing activity and stability can be obtained.

As a preferable metal ion, there may be mentioned a copper ion, a zinc ion, a calcium ion, a magnesium ion, a silver ion, a tin ion, an aluminum ion, or a manganese ion.

Examples of the compound which releases a metal ion include the following: e.g., copper compounds such as copper chloride, copper fluoride, copper sulfate, copper nitrate, copper hydroxide, copper citrate, copper gluconate, copper aspartate, copper glutamate, sodium copper chlorophyllin and copper chlorophyll; zinc compounds such as zinc chloride, zinc fluoride, zinc sulfate, zinc nitrate, zinc hydroxide, zinc citrate, zinc gluconate, zinc aspartate, zinc glutamate, zinc phosphate, and zinc lactate; calcium compounds such as calcium chloride, calcium hydroxide, calcium citrate, calcium gluconate, calcium L-glutamate, calcium carbonate, calcium lactate, calcium pantothenate, calcium dihydrogen pyrophosphate, calcium propionate, calcium sulfate, tricalcium phosphate, calcium monohydrogen phosphate, calcium dihydrogen phosphate, and disodium calcium ethylenediaminetetraacetate; magnesium compounds such as magnesium chloride, magnesium sulfate, magnesium hydroxide, magnesium L-glutamate, magnesium oxide, and magnesium carbonate; silver compounds such as silver oxide; tin compounds such as tin chloride, tin acetate, and tin fluoride; aluminum compounds such as aluminum chloride, aluminum hydroxide, aluminum acetate, aluminum borate, aluminum phosphate, and aluminum sulfate; permanganese salts such as potassium permanganese, manganese compounds such as manganese sulfate, and the like. In addition, titanium compounds such as titanium dioxide can be also employed.

The addition amount of the metal ion varies depending on the situation of the reaction but it is preferable to add the ion so that the concentration of the metal ion in the reaction liquid becomes 0.00001 mM to 100 mM and the concentration is more preferably from 0.00005 mM to 10 mM, further preferably from 0.1 mM to 5 mM.

Moreover, in the invention, after a deodorant composition is obtained by reacting a polyphenol or a polyphenol and an amino acid in an alkaline solvent in the coexistence of oxygen molecules, a metal ion may be added thereto to form a deodorant composition.

In the invention, at obtaining the deodorant composition by reacting a polyphenol and an amino acid in an alkaline solvent in the coexistence of oxygen molecules, a plant extract containing a polyphenol and an amino acid can be used instead of the polyphenol and the amino acid. As the plant extract in this case, a plant extract containing a polyphenol and an amino acid in a high concentration may be mentioned. As the plant extracts, those prepared by known methods may be used or commercially available ones may be used.

For example, the deodorant composition of the invention can be also obtained by adding a plant extract containing a polyphenol and an amino acid, i.e., an extract from at least one portion selected from leaves, stems, roots, fruits, and the like of a plant to a solvent showing alkalinity, adjusting the reaction liquid during the reaction to pH 6.5 or more, and treating it at an oxygen supplying amount of 1 mg/L or more at a reaction temperature of 0° C. to a refluxing temperature of the solvent for a reaction time of several minutes to 24 hours. Examples of the alkaline substance and solvent in this case include those described in the above and the composition is obtained by operating the reaction under the same conditions as described above. In the case that the plant extract containing a polyphenol and an amino acid is used instead of the polyphenol and the amino acid, at least one selected from a polyphenol-containing plant extract containing substantially no amino acid, an amino acid-containing plant extract containing substantially no polyphenol, a polyphenol, and an amino acid may be further used in combination. Examples of the plant extract will be shown below.

Moreover, in the invention, at obtaining the deodorant composition by reacting a polyphenol and an amino acid in an alkaline solvent in the coexistence of oxygen molecules at a reaction pH value of 6.5 or more, a plant body containing a polyphenol and an amino acid can be also used instead of the polyphenol and the amino acid. The plant body in this case is preferably one containing a polyphenol and an amino acid in a high concentration.

For example, the deodorant composition of the invention can be also obtained by adding a plant body containing the polyphenol and the amino acid of the invention, i.e., at least one portion selected from leaves, stems, roots, fruits, and the like of a plant to a solvent showing alkalinity, adjusting the reaction liquid during the reaction to pH 6.5 or more, and treating it at an oxygen supplying amount of 1 mg/L or more at a reaction temperature of 0° C. to a refluxing temperature of the solvent for a reaction time of several minutes to 24 hours. Examples of the alkaline substance and solvent include those described in the above and the composition is obtained by operating the reaction under the same conditions as described above. As the plant body, plants exemplified in the following plant extract can be used. In the case that the plant body containing a polyphenol and an amino acid is used instead of the polyphenol and the amino acid, at least one selected from a polyphenol-containing plant extract containing substantially no amino acid, an amino acid-containing plant extract containing substantially no polyphenol, a plant extract containing a polyphenol and an amino acid, a polyphenol, and an amino acid may be further used in combination. Herein, the amount of the amino acid or polyphenol which is "substantially not contained" is an amount imparting no influence to the reaction and is an amount which is less than detection limit when measured according to a generally known method.

Examples of the plant extract include extracts obtainable from *aloe*, anise seeds, elder, *eleutherococcus*, psyllium, orange flower, allspice, oregano, valerian, chamomile, *capsicum* pepper, cardamon, *cassia*, garlic, caraway seeds, clove, cumin seeds, kola, coriander seeds, *Rhus javanica*, saffron, *zanthoxylum*, juniper berry, cinnamon, ginger, star anise, St. Johns wart, celery seed, savory, sesame, pieplant, tarragon, turmeric, thistle, *Anethum graveolens*, nutmeg, nettle, *hibiscus, hamamelis*, birch, basil, bitter orange, fennel, primrose, fenugreek, *verbena, Laurus nobilis*, hop, boldo, horseradish, poppy seed, gallnut, marigold, marrow, marjoram, mustard, Millefeuille, mint leaves, *melissa*, mace, lindane, *Gentiana scabra* var. *buergeri*, rosehip, rosemary, *Rosmarinus officinalis*, sunflower seeds, grape pericarp, apple, carrot leaves, banana, strawberry, apricot, peach, plum, pineapple, pear, persimmon, cherry, papaya, mango, avocado, melon, loquat, fig, kiwi, prune, blueberry, black berry, raspberry, cranberry, coffee beans, cacao beans, grape seeds, grape fruits seeds, pecan nut, cashew nut, chestnut, coconut, peanut, walnut, green tea leaves, black tea leaves, oolong tea leaves, tobacco, *perilla* leaves, garden thyme, sage, lavender, spearmint, peppermint, spotted thistle, hyssop, sweet basil, marigold, dandelion, artichoke, *Matricaria chamomille, Agrimonia pilosa* var. *japonica*, licorice, anise, yarrow, *eucalyptus*, wormwood, balm, *Angelica pubescens*, fenugreek, *Capsicum annuum* var. *angulosum*, fennel, red pepper, coriander seeds, caraway seeds, fennel seeds, ginger, horseradish, *Origanum majorana, Origanum vulgare*, mustard, parsley, pepper, savory, tarragon, queen lily, wasabi, dill seeds, citrus fruits, and the like. Two or more of these plant extracts may be used in combination.

At the preparation of the deodorant composition of the invention, additives already conventionally used may be coexisted in the reaction system.

Thus, there is obtained the colored compound which is an active component of the deodorant composition of the invention. The color of the resulting reaction liquid widely varies depending on the kind of the polyphenol as a starting substance, the presence of an amino acid, the kind of the amino acid, and the ratio thereof. Moreover, since the density of the color also varies depending on the reaction time and pH, the color cannot be unconditionally prescribed.

For example, when the case of chlorogenic acid is described as an example, the color of the reaction liquid which is pale yellow at the initial stage of the reaction changes into brown with time and finally into dark brown. In the case of quercetin, the color of the reaction liquid which is pale pink at the initial stage of the reaction increases in red with time and finally into deep wine red. In the case of gallic acid, the color of the reaction liquid which is pale yellow at the initial stage of the reaction changes into greenish with time and finally into dark green. In the case of pyrocatechol, the color of the reaction liquid which is pale pink at the initial stage of the reaction changes into brown with time and finally into dark brown.

Moreover, in the case that glycine is selected as an amino acid and reacted, the reaction liquid with chlorogenic acid is green, the reaction liquid with (+)-catechin is red, the reaction liquid with protocatechuic acid is red, the reaction liquid with pyrocatechol is pale pink, the reaction liquid with aesculetin is brown, the reaction liquid with hydroquinone is brown, the reaction liquid with quercetin is red, and the reaction liquid with gallic acid is brown.

With regard to the reaction with a polyphenol or a polyphenol and an amino acid in most cases, the reaction liquid has a pale color at the initial stage of the reaction but the color of the reaction liquid is darkened and finally tends to become a dark color. The time required for darkening the color of the reaction liquid varies depending on the kind of the polyphenol, the combination of the polyphenol and the amino acid, and the reaction conditions but is about several minutes after the start of the reaction and sometimes about 20 minutes or 30 minutes.

As mentioned above, the deodorant composition prepared in the invention contains the colored compound. The colored compound acts a role as a deodorizing active component. The colored compounds have various chemical structures and, for example, reaction products of polyphenols which are starting materials, polymeric products prepared from polyphenols, reaction products from polyphenols and amino acids, polymeric reaction products prepared from polyphenols and amino acids, oxides of polyphenols, oxides of the above reaction products and polymeric products, and further various radicals such as a phenoxy radical which is one of oxidation products of polyphenols also belong to the category of the colored compounds of the invention.

The ratio of the colored compound contained in the deodorant composition of the invention is from 10 ppm to 100% by weight.

It is preferred that the molecular weight of the colored compound in the resulting deodorant composition exceeds the molecular weight of the polyphenol before the reaction as a starting material or the sum of the molecular weights of the polyphenol and the amino acid, and is 10,000 or less.

The molecular weight of the colored compound can be measured by the following method. Namely, the deodorant composition prepared by one of the above various methods is concentrated by centrifugation and it is determined whether the concentrate passes through or remains on a filtration membrane having a certain pores, whereby a corresponding molecular weight is determined based on the pore size of the filtration membrane on which the concentrate remains. As the filtration membranes to be used, commercially available products may be used.

The deodorizing active component in the invention may be an oxide of a starting material obtained by the reaction of the starting material with oxygen molecules, and hence the range of the molecular weight of the deodorizing active component is expressed as above.

The thus obtained reaction liquid containing the deodorizing active component can be used as the deodorant composition without further treatment. Alternatively, if necessary, by a method of further concentrating the reaction liquid containing the deodorizing active component or the like method, a deodorant composition having a high content of the deodorizing active component can be obtained. Furthermore, a solid deodorant composition can be obtained by removing liquid components from the reaction liquid containing the deodorizing active component by a known method such as a vacuum-drying method or a freeze-drying method. Alternatively, the liquid may be supported on any carrier such as a liquid, a solid, or a gel substance to form a deodorant composition.

Preferred examples of the liquid include water, hydrous alcohols, lower alcohols (methanol, ethanol, butanol, propanol, etc.), polyol-based organic solvents (ethylene glycol, propylene glycol, etc.), benzyl alcohol, glycerin, monoglycerides, diglycerides, animal and plant oils, essential oils, and the like.

Preferred examples of the solid include porous carriers, e.g., sugars such as dextrin, cyclodextrin, glucose, lactose, and starch; plastic carriers such as plastic particles and foam plastics; inorganic particles such as silica gel particles, diatomaceous earth, activated clay, vermiculite, alumina, zeolite, perlite, clay minerals, unglazed pottery, ceramics, metals, glass, and active carbon; water-absorbable polymers; natural carriers such as buckwheat chaff, chaff, sawdust, and baked products thereof; fibrous carriers such as fibers, fiber aggregates, fiber bunch, non-woven fabrics, knitted goods, textiles, pulp, paper, paper products (cardboards, honeycomb, etc.); synthetic molecules such as crown ethers, cryptands, cyclophanes, and carixarenes; and the like. The "porous" herein includes the case that the carrier itself is porous and the case that numerous voids are present between the carriers.

Examples of the gel substances include aqueous gelating agents such as carrageenin, carboxyvinyl polymers, crosslinked polyacrylic acid, hydroxyethyl cellulose, carboxymethyl cellulose, sodium acrylate, agar, gelatin, pectin, pharselan, xanthan gum, locust bean gum, duran gum, and collagen; oily gelating agents such as metal soaps and dibenzylidene sorbitol. They can be used solely or in combination.

As a method for supporting the deodorant composition of the invention on the carrier, there can be mentioned a method of attaching the deodorant composition in a solution state by means of coating, impregnation, spraying, or the like and subsequently drying (e.g., air-drying at 60° C. for 12 hours) as an example.

The deodorant composition of the invention may be used after capsulation by a known method using gelatin, gum arabic, sodium arginate, a cellulose derivative such as ethyl cellulose, polyvinyl alcohol, vinyl methyl ether-maleic anhydride copolymer, styrene-maleic anhydride copolymer, polyethylene, polystyrene, paraffin wax, or the like.

Moreover, particularly in the case that the deodorant composition of the invention is used in a solution state, the reduction of the amount of dissolved oxygen in the solution as far as possible remarkably enhances the storage stability of the composition of the invention in the solution and thus the case is convenient. A rough standard of the amount of dissolved oxygen convenient at storage is, for example, 0.0005% by weight, more preferably 0.00015% by weight or less.

As a method for the reduction of the amount of dissolved oxygen in the solution as far as possible, a known method may be employed, which specifically includes a method of storing the solution under a circumstance of reduced pressure, a method of subjecting the solution to degas treatment, a method of replacement with nitrogen gas or argon gas, a method of treating it under an atmosphere of nitrogen gas or argon gas, and the like.

In the case that the deodorant composition is used in a solid state, when a compound having deliquescence or high hygroscopicity is present together with the deodorant composition, the compound efficiently absorbs the moisture in the air and hence a reaction field suitable for the deodorant composition may be provided, so that the case is more preferred for exhibiting the deodorizing effect of the deodorant composition.

As examples of the compound having deliquescence or high hygroscopicity, salts and alkalis showing deliquescence by the moisture in the air or showing a property of strongly absorbing the moisture in the air are employed and particularly, salts having deliquescence or high hygroscopicity are practical.

Specific examples include lithium chloride, sodium chloride, potassium chloride, magnesium chloride, ammonium magnesium chloride, sodium magnesium chloride, potassium magnesium chloride, manganese chloride, potassium manganese chloride, antimony chloride, antimony cobalt chloride, zinc chloride, iron chloride, bismuth chloride, beryllium chloride, calcium bromide, zinc bromide, copper bromide, iron bromide, cobalt bromide, cadmium bromide, lithium iodide, sodium iodide, magnesium iodide, calcium iodide, iron iodide, nickel iodide, sodium nitrite, potassium nitrite, magnesium nitrite, ammonium nitrate, lithium nitrate, sodium nitrate, calcium nitrate, beryllium nitrate, magnesium nitrate, manganese nitrate, cerium nitrate, ammonium cerium nitrate, iron nitrate, copper nitrate, lithium chlorate, calcium chlorate, magnesium chlorate, zinc chlorate, cadmium chlorate, cobalt chlorate, copper chlorate, potassium carbonate, lithium sulfate, ammonium zinc sulfate, antimony sulfate, iron sulfate, ammonium cadmium sulfate, ammonium thiosulfate, potassium phosphate, ammonium phosphite, potassium phosphite, hydrazinium phosphite, sodium hypophosphite, potassium hypophosphite, sodium permanganate, calcium permanganate, strontium permanganate, magnesium permanganate, zinc permanganate, sodium hydroxide, potassium hydroxide, and the like. These salts may be used solely or two or more of them may be used in combination.

The most suitable amount of the compound having deliquescence or high hygroscopicity to be co-present varies depending on the kind of the compound, the environment to be applied, and intended use and hence the amount is not unconditionally determined but 0.1 to 10 weight equivalents to the deodorant composition may be mentioned as an example.

In the invention, various additives commercially available can be added to the deodorant composition obtained by the above method. Examples of the additives include extenders, antioxidants, dyestuffs, known deodorizing materials, enzymes for reducing malodor, surfactants, flavors, fragrances, stabilizing agents, antibacterial agents, moisture absorbents (calcium chloride, highly water-absorbable polymers, etc.), excipients (lactose, etc.), and the like.

They can be mixed with the deodorant composition of the invention solely or as a combination of two or more of them and thus a characteristic deodorant composition and deodorant can be prepared. Particularly, when an antibacterial agent is mixed to the deodorant composition, the deodorizing effect is synergistically enhanced and hence it becomes possible to prepare a more characteristic deodorant composition and deodorant by combining the agent with other additives to exhibit performances of the additives. The mixing amounts of the above additives are not particularly limited as far as the amounts are such amounts that they can accomplish desired purposes.

The extenders include sugars, polysaccharides, processed starch, casein, gelatin, carboxymethyl cellulose (hereinafter referred to as CMC), lecithin, and the like.

As the antioxidants, there are known butylhydroxytoluene, butylhydroxyanisole, citric acid, biofavoic acid, glutathione, selenium, licopene, vitamin A, vitamin E, and vitamin C, and also pyrrolopyrrole derivatives, free radical scavengers obtainable form extracts of various plants, enzymes having antioxidant properties such as superoxide dismutases and glutathione peroxidases, and the like.

As the dyestuffs, dyes, lakes, organic synthetic dyestuffs (tar dyestuffs) such as organic pigments, natural dyestuffs, inorganic pigments, and the like are known. Specifically, there are known hibiscus dyestuff, huckleberry dyestuff, plume dyestuff, laver dyestuff, duberry dyestuff, grape juice dyestuff, blackberry dyestuff, blueberry dyestuff, mulberry dyestuff, morello cherry dyestuff, red currant dyestuff, loganberry dyestuff, paplica powder, malt extract, rutin, flavonoids, red cabbage dyestuff, red radish dyestuff, adzuki bean dyestuff, turmeric dyestuff, olive tea, cowberry dyestuff, *chlorella* dyestuff, saffron dyestuff, *perilla* dyestuff, strawberry dyestuff, chicory dyestuff, pecannut dyestuff, red rice malt dyestuff, safflower dyestuff, purple sweet potato dyestuff, lac dyestuff, *spirulina* dyestuff, onion dyestuff, tamarind dyestuff, chili pepper dyestuff, *gardenia* dyestuff, *Gardenia jasminoides* dyestuff, sikon dyestuff, rosewood dyestuff, euphausiid dyestuff, orange dyestuff, carrot carotene, carmel, sodium iron chlorophyllin, riboflavin, norbixin potassium, norbixin sodium, alamance, erythrocin, new coccin, phloxine B, rose bengal, acid red, cutoradin, sunset yellow, first green, brilliant blue, indigocarmine, lake red C, lithol red, rhodamine, phloxine, indigo, ponceau, orange I, sudan blue, and the like. Inorganic pigments include mica, talc, calcium carbonate, kaolin, silicic anhydride, aluminum oxide, colcothar, iron oxide, ultramarine, carbon black, titanium dioxide, zinc dioxide, mica, bismuth oxychloride, boron nitride, photochromic pigments, hybrid fine powder, synthetic mica, and the like.

The antibacterial agents include benzoic acid, sodium benzoate, isopropyl p-hydroxybenzoate, isobutyl p-hydroxybenzoate, ethyl p-hydroxybenzoate, methyl p-hydroxybenzoate, butyl p-hydroxybenzoate, propyl p-hydroxybenzoate, sodium sulfite, sodium hyposulfite, potassium pyrosulfite, sorbic acid, potassium sorbate, sodium dehydroacetate, thujaplicin, udo extract, storax extract, wild tansy extract, milt protein extract, zymolytic Job's tears extract, and the like.

Examples of known deodorants include deodorants due to the desulfurizing action of iron sulfates such as ferrous sulfate and iron chlorides; deodorants due to the chemical reaction of acidic agents, alkaline agents, oxidizing agents, and the like; deodorants due to the adding or condensing action of (meth)acrylate esters, maleate esters, and the like as adding agents or glyoxal as a condensing agent; deodorants due to the ion-exchanging action of amphoteric ion-exchange resins, cationic ion-exchange resins, anionic ion-exchange resins, and the like; deodorants due to the chemical substance-attaching or adsorbing action of alkaline or acidic attaching active carbon, mixtures of active carbon and a chemical reagent, and the like; deodorants due to the adsorbing action of porous adsorbents such as neutral active carbon, a fibrous carbon deodorant, zeolite, and active clay; deodorants due to the enzymatic action of digestive enzymes or enzymes produced by mouth good bacterium LS-1 lactic acid bacterium, yeasts, soil bacteria, and the like or bacteria thereof; deodorants due to the antiseptic or bactericidal action of chloramine T, parabens, phenols, and the like; polyphenol deodorants such as persimmon polyphenol, tea chatechin, rosemary extract, oolong tea extract, tansy extract, white oak leave extract, and rice bran/soy bean-firing extract; and the like. In addition, there are also included cyclodextrin, champignon extract, rooibos extract, sodium iron chlorophyllin, active carbon, zeolite, and the like.

Examples of the enzymes for reducing malodor include carbohydrases, lipases, proteases, phytases, and the like. By mixing these enzymes in the deodorant composition, the deodorizing effect can be enhanced.

The surfactants include nonion types (polyoxyethylene alkyl ethers, fatty acid alkylolamides, etc.), acylglutamic acid types, and the like. These surfactants are preferably used solely or as a combination of two or more of them. Examples of the polyoxyethylene alkyl ethers include polyoxyethylene stearyl, polyoxyethylene hardened castor oil, and the like. Examples of the fatty acid alkylolamides include coconut-oil fatty acid diethanolamide. The acylglutamic acid types include glutamate esters of saturated and unsaturated fatty acids having 12 to 18 carbon atoms and coconut-oil fatty acids, hardened coconut-oil fatty acids, palm-oil fatty acids, hardened palm oil fatty acids, beef-tallow fatty acids, hardened beef-tallow fatty acids, and the like which are mixtures thereof, and specifically, include N-coconut-oil fatty acid-acyl-L-glutamic triethanolamine, lauroyl-L-glutamic triethanolamine, sodium N-coconut-oil fatty acid-acyl-L-glutamate, sodium N-lauroyl-L-glutamate, sodium N-myristoyl-L-glutamate, sodium N-coconut-oil fatty acid-hardened tallow fatty acid-acyl-L-glutamate, potassium N-coconut-oil fatty acid-acyl-L-glutamate, and the like.

Moreover, flavors and/or fragrances may be mixed with the deodorant compositions. As a result, a strange odor characteristic to the substrate can be masked and further pleasant aroma can be also imparted.

The mixing amount of the flavors and/or fragrances varies depending on the polyphenol and amino acid to be adopted, the application target of the deodorant composition, the method of using the same, and the like but is usually preferably from 0.001 to 500 equivalents to the deodorant composition by weight.

The flavor to be used in the invention includes synthetic aroma chemicals such as esters, alcohols, aldehydes, ketones, acetals, phenols, ethers, lactones, furans, hydrocarbons, and acids, flavor materials of natural origin, and the like.

Examples of the esters in the synthetic aroma chemicals to be used as the above flavor preferably include acrylate esters (methyl, ethyl, etc.), acetoacetate esters (methyl, ethyl, etc.), anisate esters (methyl, ethyl, etc.), benzoate esters (allyl, isoamyl, ethyl, geranyl, linalyl, phenylethyl, hexyl, cis-3-hexenyl, benzyl, methyl, etc.), anthranilate esters (cinnamyl, cis-3-hexenyl, methyl, ethyl, linalyl, isobutyl, etc.), N-methylanthranilate esters (methyl, ethyl, etc.), isovalerate ester (amyl, allyl, isoamyl, isobutyl, isopropyl, ethyl, octyl, geranyl, cyclohexyl, citronellyl, terpenyl, linalyl, cinnamyl, phenylethyl, butyl, propyl, hexyl, benzyl, methyl, rhodinyl, etc.), isobutyrate esters (isoamyl, geranyl, citronellyl, terpenyl, cinnamyl, octyl, neryl, phenylethyl, phenylpropyl, phenoxyethyl, butyl, propyl, isopropyl, hexyl, benzyl, methyl, ethyl, linalyl, rhodinyl, etc.), undecylenate esters (allyl, isoamyl, butyl, ethyl, methyl, etc.), octanoate esters (allyl, isoamyl, ethyl, octyl, hexyl, butyl, methyl, linalyl, etc.), octenoate esters (methyl, ethyl, etc.), octynecarboxylate esters (methyl, ethyl, etc.), caproate esters (allyl, amyl, isoamyl, methyl, ethyl, isobutyl, propyl, hexyl, cis-3-hexenyl, trans-2-hexenyl, linalyl, geranyl, cyclohexyl, etc.), hexenoate esters (methyl, ethyl, etc.), valerate esters (amyl, isopropyl, isobutyl, ethyl, cis-3-hexenyl, trans-2-hexenyl, cinnamyl, phenylethyl, methyl, etc.), formate esters (anisyl, isoamyl, isopropyl, ethyl, octyl, geranyl, citronellyl, cinnamyl, cyclohexyl, terpinyl, phenylethyl, butyl, propyl, hexyl, cis-3-hexenyl, benzyl, linalyl, rhodinyl, etc.), crotonate esters (isobutyl, ethyl, cyclohexyl, etc.), cinnamate esters (allyl, ethyl, methyl, isopropyl, propyl, 3-phenylpropyl, benzyl, cyclohexyl, methyl, etc.), succinate esters (monomenthyl, diethyl, dimethyl, etc.), acetate esters (anisyl, amyl, α-amylcinnamyl, isoamyl, isobutyl, isopropyl, isopulegyl, isobornyl, isoeugenyl, eugenyl, 2-ethylbutyl, ethyl, 3-octyl, carvyl, dihydrocarvyl, p-cresyl, o-cresyl, geranyl, α- or β-santalyl, cyclohexyl, cycloneryl, dihydrocuminyl, dimethylbenzylcarbinyl, cinnamyl, styrallyl, decyl, dodecyl, terpinyl, guanyl, neryl, nonyl, phenylethyl, phenylpropyl, butyl, furfuryl, propyl, hexyl, cis-3-hexenyl, trans-2-hexenyl, cis-3-nonenyl, cis-6-nonenyl, cis-3, cis-6-nonadienyl, 3-methyl-2-butenyl, menthyl, heptyl, benzyl, bornyl, myrcenyl, dihydromyrcenyl, myrtenyl, methyl, 2-methylbutyl, menthyl, linalyl, rhodinyl, etc.), salicylate esters (allyl, isoamyl, phenyl, phenylethyl, benzyl, ethyl, methyl, etc.), cyclohexylalkanoate esters (ethyl cyclohexylacetate, allyl cyclohexylpropionate, allyl cyclohexylbutyrate, allyl cyclohexylhexanoate, allyl cyclohexyldecanoate, allyl cyclohexylvalerate, etc.), stearate esters (ethyl, propyl, butyl, etc.), sebacate esters (diethyl, dimethyl, etc.), decanoate esters (isoamyl, ethyl, butyl, methyl, etc.), dodecanoate esters (isoamyl, ethyl, butyl, etc.), lactate esters (isoamyl, ethyl, butyl, etc.), nonanoate esters (ethyl, phenylethyl, methyl, etc.), nonenoate esters (allyl, ethyl, methyl, etc.), hydroxyhexanoate esters (ethyl, methyl, etc.), phenylacetate esters (isoamyl, isobutyl, ethyl, geranyl, citronellyl, cis-3-hexenyl, methyl, etc.), phenoxyacetate esters (allyl, ethyl, methyl, etc.), furancarboxylate esters (ethyl furancarboxylate, methyl furancarboxylate, hexyl furancarboxylate, isobutyl furanpropionate, etc.), propionate esters (anisyl, allyl, ethyl, amyl, isoamyl, propyl, butyl, isobutyl, isopropyl, benzyl, geranyl, cyclohexyl, citronellyl, cinnamyl, tetrahydrofurfuryl, tricyclodecenyl, heptyl, bornyl, methyl, menthyl, linalyl, terpinyl, α-methylpropionyl, β-methylpropionyl, etc.), heptanoate esters (allyl, ethyl, octyl, propyl, methyl, etc.), heptynecarboxylate esters (allyl, ethyl, propyl, methyl, etc.), myristate esters (isopropyl, ethyl, methyl, etc.), phenylglycidate esters (ethyl phenylglycidate, ethyl 3-methylphenylglycidate, ethyl p-methyl-β-phenylglycidate, etc.), 2-methylbutyrate esters (methyl, ethyl, octyl, phenylethyl, butyl, hexyl, benzyl, etc.), 3-methylbutyrate esters (methyl, ethyl, etc.), butyrate esters (anisyl, amyl, allyl, isoamyl, methyl, ethyl, propyl, octyl, guanyl, linalyl, geranyl, cyclohexyl, citronellyl, cinnamyl, neryl, terpenyl, phenylpropyl, β-phenylethyl, butyl, hexyl, cis-3-hexenyl, trans-2-hexenyl, benzyl, rhodinyl, etc.), hydroxybutyrate esters (3-hydroxybuyrate methyl, ethyl, or menthyl, etc.), and the like.

Examples of the alcohols to be used as the flavors in the invention preferably include aliphatic alcohols (isoamyl alcohol, isopulegol, 2-ethylhexanol, 1-octanol, 3-octanol, 1-octen-3-ol, 1-decanol, 1-dodecanol, 2,6-nonadienol, nonanol, 2-nonanol, cis-6-nonenol, trans-2, cis-6-nonadienol, cis-3, cis-6-nonadienol, butanol, hexanol, cis-3-hexenol, trans-2-hexenol, 1-undecanol, heptanol, 2-heptanol, 3-methyl-1-pentanol, etc.), terpene alcohols (carveol, borneol, isoborneol, carveol, piperitol, geraniol, α- or β-santalol, citronellol, 4-thujanol, terpineol, 4-terpineol, nerol, myrcenol, myrtenol, menthol, dihydromyrcenol, tetrahydromyrcenol, nerolidol, hydroxycitronerol, farnesol, *perilla* alcohol, rhodinol, linalool, etc.), aromatic alcohols (anise alcohol, α-amylcinnamic alcohol, isopropylbenzylcarbinol, carvacrol, cuminic alcohol, dimethylbenzylcarbinol, cinnamic alcohol, phenylallyl alcohol, phenylethylcarbinol, β-phenylethyl alcohol, 3-phenylpropyl alcohol, benzyl alcohol, etc.), and the like.

Examples of the aldehydes to be used as the flavors in the invention preferably include aliphatic aldehydes (acetaldehyde, octanal, nonanal, decanal, undecanal, 2,6-dimethyl-5-heptanal, 3,5,5-trimethylhexanal, cis-3, cis-6-nonadienal, trans-2, cis-6-nonadienal, valeraldehyde, propanal, isopropanal, hexanal, trans-2-hexenal, cis-3-hexenal, 2-pentenal, dodecanal, tetradecanal, trans-4-decenal, trans-2-tridecenal, trans-2-dodecenal, trans-2-undecenal, 2,4-hexadienal, cis-6-nonenal, trans-2-nonenal, 2-methylbutanal, etc.), aromatic aldehydes (anisaldehyde, α-amylcinnamic aldehyde), α-methylcinnamic aldehyde, cyclamen aldehyde, p-isopropylphenylacetaldehyde, ethylvanillin, cuminaldehyde, salicyladehyde, cinnamic aldehyde, o-, m- or p-tolylaldehyde, vanillin, piperonal, phenylacetaldehyde, heliotropin, benzaldehyde, 4-methyl-2-phenyl-2-pentenal, p-methoxycinnamic aldehyde, p-methoxybenzaldehyde, etc.), terpene aldehydes (geranial, citral, citronellal, α-sinensal, β-sinensal, perillaldehyde, hydroxycitronellal, tetrahydrocitral, myrtenal, cyclocitral, isocyclocitral, citronellyloxyacetaldehyde, neral, α-methylenecitronellal, myrac aldehyde, vernaldehyde, safranal, etc.), and the like.

Preferred examples of the ketones to be used as the flavors in the invention preferably include cyclic ketones (menthone, isomenthone, carvone, dihydrocarvone, pulegone, piperitone, 1-acetyl-3,3-dimethyl-1-cyclohexene, cis-jasmone, α-, β- or γ-iron, ethylmaltol, cyclotene, dihydronootkatone, 3,4-dimethyl-1,2-cyclopentadione, sotolone, α-, β- γ- or δ-damascone, α-, β- or γ-damascenone, nootkatone, 2-sec-butylcyclohexanone, maltol, α-, β- or γ-ionone, α-, β- or γ-methylionone, α-, β- or γ-isomethylionone, furaneol, camphor, etc.), aromatic ketones (acetonaphthone, acetophenone, anisylideneacetone, raspberry ketone, p-methylacetophenone, anisylacetone, p-methoxyacetophenone, etc.), linear ketones (diacetyl, 2-nonanone, diacetyl, 2-heptanone, 2,3-heptanedione, 2-pentanone, methyl amyl ketone, methyl nonyl ketone, β-methyl naphthyl ketone, methylheptanone, 3-heptanone, 4-heptanone, 3-octanone, 2,3-hexanedione, 2-undecanone, dimethyloctenone, 6-methyl-5-heptyn-3-one, etc.), and the like.

Preferred examples of the acetals to be used as the flavors in the invention include acetaldehyde diethyl acetal, acetaldehyde diamyl acetal, acetaldehyde dihexyl acetal, acetaldehyde propylene glycol acetal, acetaldehyde ethyl cis-3-hexenyl acetal, benzaldehyde glycerin acetal, benzaldehyde propylene glycol acetal, citral dimethyl acetal, citral diethyl acetal, citral propylene glycol acetal, citral ethylene glycol acetal, phenylacetaldehyde dimethyl acetal, citronellyl methyl acetal, acetaldehyde phenylethyl propyl acetal, hexanal dimethyl acetal, hexanal dihexyl acetal, hexanal propylene glycol acetal, trans-2-hexenal diethyl acetal, trans-2-hexenal propylene glycol acetal, cis-3-hexenal diethyl acetal, heptanal diethyl acetal, heptanal ethylene glycol acetal, octanal dmethyl acetal, nonanal dimethyl acetal, decanal dimethyl acetal, decanal diethyl acetal, 2-methylundecanal dimethyl acetal, citronellal dimethyl acetal, ambersage (manufactured by Givaudan), ethyl acetoacetate ethylene glycol acetal, 2-phenylpropanal dimethyl acetal, and the like.

Preferred examples of the phenols to be used as the flavors in the invention include eugenol, isoeugenol, 2-methoxy-4-vinylphenol, thymol, carvacrol, guaiacol, chavicol, and the like.

Preferred examples of the ethers to be used as the flavors in the invention include anethole, 1,4-cineole, 1,8-cineole, dibenzyl ether, linalool oxide, limonene oxide, nerol oxide, rose oxide, methylisoeugenol, methyl chavicol, isoamyl phenylethyl ether, β-naphthyl methyl ether, phenyl propyl ether, p-cresyl methyl ether, vanillyl butyl ether, α-terpinyl methyl ether, citronellyl ethyl ether, geranyl ethyl ether, rose-furan, theaspirane, decyl methyl ether, methyl phenylmethyl ether, and the like.

Preferred examples of the lactones to be used as the flavors in the invention include γ- or δ-decalactone, γ-heptalactone, γ-nonalactone, γ- or δ-hexylactone, γ- or δ-octalactone, γ- or δ-undecalactone, δ-dodecalactone, δ-2-decenolactone, methyllactone, 5-hydroxy-8-undecenenoic acid δ-lactone, jasmine lactone, menthalactone, dihydrocoumarin, octahydrocoumarin, 6-methylcoumarin, and the like.

Preferred examples of the furans to be used as the flavors in the invention include furan, 2-methylfuran, 3-methylfuran, 2-ethylfuran, 2,5-diethyltetrahydrofuran, 3-hydroxy-2-methyltetrahydrofuran, 2-(methoxymethyl)furan, 2,3-dihydrofuran, menthofuran, furfural, 5-methylfurfural, 3-(2-furyl)-2-methyl-2-propenal, 5-(hydroxymethyl)furfural, 2,5-dimethyl-4-hydroxy-3(2H)-furanone (furaneol), 4,5-dimethyl-3-hydroxy-2(5H)-furanone (sotolone), 2-ethyl-4-hydroxy-5-methyl-3(2H)-furanone (homofuranol), 5-ethyl-3-hydroxy-4-methyl-2(5H)furanone (homosotolone), 3-methyl-1,2-cyclopentanedione (cyclotene), 2(5H)-furanone, 4-methyl-2(5H)-furanone, 5-methyl-2(5H)-furanone, 2-methyl-3(2H)-furanone, 5-methyl-3(2H)-furanone, 2-acetylfuranone, 2-acetyl-5-methylfuran, furfuryl alcohol, methyl 2-furancarboxylate, ethyl 2-furancarboxylate, furfuryl acetate, and the like.

Preferred examples of the hydrocarbons to be used as the flavors in the invention include α-bisabolene, β-caryophyllene, p-cymene, terpinene, terpinolene, cadinene, farnesene, limonene, ocimene, myrcene, α- or β-pinene, 1,3,5-undecatriene, valencene, and the like.

Moreover, preferred examples of the acids to be used as the flavors in the invention include octanoic acid, nonanoic acid, decanoic acid, 2-decenoic acid, geranic acid, dodecanoic acid, myristic acid, stearic acid, lactic acid, phenylacetic acid, pyruvic acid, trans-2-methyl-2-pentenoic acid, 2-methyl-cis-3-pentenoic acid, 2-methyl-4-pentenoic acid, cyclohexanecarboxylic acid, and the like.

Furthermore, examples of the flavor materials of natural origin to be used as the flavors include anise, orange, lemon, lime, mandarin, petit grain, bergamot, lemon balm, grapefruit, elemi, olibanum, lemon grass, neroli, marjoram, angelica root, star anise, basil, bay, calamus, chamomile, caraway, cardamom, *cassia*, cinnamon, peppermint, spearmint, mint, penny royal, pepper, *perilla*, cypress, oregano, cascarilla, ginger, parsley, pine needle, sage, hyssop, tea tree, mustard, horseradish, clarisage, clove, cognac, coriander, estragon, eucalyptus, fennel, guaiac wood, dill, cajuput, worm seed, pimento, juniper, fenugreek, garlic, laurel, mace, mil, nutmeg, spruce, geranium, citronella, lavender, lavandin, palmarosa, rose, rosemary, sandalwood, oak moth, cider wood, vetiver, linaloe, bois de rose, patchouli, labdanum, cumin, thyme, ylang-ylang, birth, *capsicum*, celery, tolu balsam, djenne, inmortel, benzoin, jasmine, *cassia*, tuberose, mignonette, marigold, mimosa, opopanax, orris, vanilla, licorice, and the like. The flavor components contained in these flavor materials of natural origin can be also used.

The fragrance to be used in the invention includes hydrocarbons, alcohols, phenols, aldehydes and/or acetals, ketones and/or ketals, ethers, synthetic musks, acids, lactones, esters, halogen-containing compounds, fragrance materials of natural origin, and the like.

The hydrocarbons to be used as fragrances in the invention are not particularly limited as far as they are volatile organic compounds composed of carbon and hydrogen. Examples thereof include aliphatic hydrocarbons, alicyclic hydrocarbons, terpene hydrocarbons, aromatic hydrocarbons, and the like. Preferred examples include 1,3,5-undecatriene, p-cymene, α-pinene, α-phellandrene, β-caryophyllene, β-pinene, Δ-carene, allo-ocimene, ocimene, dihydromyrcene, dipentene, sclarene, cedrene, terpinene, terpinolene, valencene, bisabolene, farnesene, myrcene, limonene, longifolene, adamantane, isolongifolene, camphene, guaiene, diphenyl, diphenylmethane, biphenyl, 3,7-dimethyl-1,3,6-octatriene, 4-isopropyl-1-methyl-2-propenylbenzene, 7-methyl-3-methylene-1,6-octadiene, p-ethylstyrene, α-p-dimethylstyrene, isoprene, undecatriene, undecane, octadecadiene, octadecane, octadecene, octane, octene, cumene, sabinene, cyclohexane, cyclohexene, cyclopentadiene, dicyclopentadiene, styrene, decalin, decane, tetradecane, tetralin, dodecane, tridecane, tridecene, naphthalene, nonane, nonene, norbornane, norbornene, hexadecane, hexane, heptadecadiene, heptadecane, heptadecene, heptane, and pentadecane. Further preferred examples include 1,3,5-undecatriene, p-cymene, α-pinene, α-phellandrene, β-caryophyllene, β-pinene, Δ-carene, allo-ocimene, ocimene, dihydromyrcene, dipentene, sclarene, cedrene, terpinene, terpinolene, valencene, bisabolene, farnesene, myrcene, limonene, longifolene, adamantane, isolongifolene, and camphene.

The alcohols to be used as fragrances in the invention are not particularly limited as far as they are volatile organic compounds having a hydroxyl group. Examples thereof include aliphatic alcohols, alicyclic alcohols, terpene alcohols, aromatic alcohols, and the like. Preferred examples include 10-undecenol, 1-octen-3-ol, 2,6-nonadienol, 2-tert-butylcyclohexanol, 2-ethylhexanol, 2-heptanol, 3,5,5-trimethylhexanol, 3-octanol, 3-phenylpropyl alcohol, L-menthol, n-decyl alcohol, α-dimethylbenzyl alcohol, p-tert-butylcyclohexanol, p-methyldimethylbenzylcarbinol, α,3,3-trimethyl-2-norbornanemethanol, α-n-amylcinnamic alcohol, α-fenchyl alcohol, β-phenylethyl alcohol, anise alcohol, amber core, ambrinol, isononyl alcohol, isophytol, isopulegol, isoborneol, ethyllinalool, octanol, carveol, geraniol, santalol, cis-3-hexen-1-ol, cis-6-nonenol, citronellol, dihydro-α-terpineol, dihydrocitronellol, dihydromyrcenol, dihydrolinalool, dimethylphenylethylcarbinol, dimethylbenzylcarbinol, cinnamic alcohol, styrally alcohol, cedrol, terpineol, terpinen-4-ol, Timberol, tetrahydrogeraniol, tetrahydromyrcenol, tetrahydromugol, tetrahydrolinalool, nerol, nerolidol, nonanol, nonyl alcohol, nopol, hydrotropyl alcohol, Bacdanol, patchouli alcohol, farnesol, phytol, phenylethylmethylethylcarbinol, phenoxyethyl alcohol, furfuryl alcohol, vetivenol, *perilla* alcohol, benzyl alcohol, mayol, myrcenol, myrtenol, lavandulol, linalool, 1-(2,2,6-trimethylcyclohexanyl)-hexan-3-ol, 1,1-dimethyl-3-phenylpropanol, 1-decanol, 1-dodecanol, 1-nonen-3-ol, 1-heptanol, 1-penten-3-ol, 2,2-dimethyl-3-phenylpropanol, 2,4-dimethyl-3-cyclohexene-1-methanol, 2,4-dimethylbenzyl alcohol, 2,4-hexadienol, 2,5,5-trimethyloctahydro-2-naphthol, 2,6-dimethylheptan-2-ol, 2-isobutyl-4-hydroxy-4-methyltetrahydropyran, 2-undecanol, 2-octanol, 2-nonanol, 2-phenylpropyl alcohol, 2-methyl-3-buten-2-ol, 2-methyl-4-(2,2,3-trimethyl-3-cyclopentenyl)-2-butenol, 2-methyl-4-(2,2,3-trimethyl-3-cyclopentenyl)-butanol, 2-methyloctanol, 2-methyldecanol, 2-methoxy-2-phenylethyl alcohol, 3,3-dimethyl-Δ2,β-norbornane-2-ethanol, 3,4,5,6,6-pentamethyl-2-heptanol, 3,6-dimethyloctan-3-ol, 3,7-dimethyl-1-octanol, 3,7-dimethyl-7-methoxyoctan-2-ol, 3-thujanol, 3-dodecanol, 3-heptanol, 3-methyl-1-phenyl-3-pentanol, 3-methyl-2-buten-1-ol, 3-methyl-5-(2,2,3-trimethyl-3-cyclopentenyl)pentan-2-ol, 3-methyl-5-phenylpentanol, 3-methylpentanol, 4-isopropylcyclohexanol, 4-thujanol, 4-methyl-3-decen-5-ol, 5-methyl-2-phenyl-2-hexanol, 6,8-dimethyl-2-nonanol, 9-decenol, 9-decen-1-ol, E.G. monobutyl ether, sec-undecylic alcohol, sec-octyl alcohol, sec-nonyl alcohol, α,α,p-trimethylphenylethyl alcohol, α,α-dimethylphenylethyl alcohol, α-isobutylphenylethyl alcohol, α-bisabolol, α-propylphenylethyl alcohol, β,γ-hexenol, β-caryophyllene alcohol, γ-4-dimethyl-3-cyclohexene-1-propanol, allo-ocimenol, Ambestol, isocamphylcyclohexanol, isocyclogeraniol, isodihydrolavandulol, isobutylbenzylcarbinol, undecanol, ethylene glycol, ethylene glycol monoethyl ether, ethylene glycol monobutyl ether, ethylene glycol monopropyl ether, ethylene glycol monomethyl ether, ocimenol, Camekol DH, cumin alcohol, geranyllinalool, sabinene hydrate, diethylene glycol, diethylene glycol monoethyl ether, diethylene glycol monobutyl ether, diethylene glycol monopropyl ether, diethylene glycol monomethyl ether, cyclohexylethyl alcohol, cyclomethylene citronellol, cis-4-hexen-1-ol, cis-p-isopropylcyclohexylmethanol, dihydrocarveol, dipropylene glycol, dipropylene glycol monoethyl ether, dipropylene glycol monobutyl ether, dipropylene glycol monopropyl ether, dipropylene glycol monomethyl ether, dimethyloctanol, dimethylvinylcarbinol, sclareol, decahydro-β-naphthol, tetrahydroallo-ocimenol, trans-2-octanol, trans-2-hexenol, trans-3-hexen-1-ol, neopentyl glycol, hydrocinnamic alcohol, vanillyl alcohol, pinocarveol, butane-1,3-diol, butane-1,3-diol monoethyl ether, butane-1,3-diol monobutyl ether, butane-1,3-diol monopropyl ether, butane-1,3-diol monomethyl ether, butane-2,3-diol, butane-2,3-diol monoethyl ether, butane-2,3-diol monobutyl ether, butane-2,3-diol monopropyl ether, butane-2,3-diol monomethyl ether, butylene glycol, propylene glycol, propylene glycol monoethyl ether, propylene glycol monobutyl ether, propylene glycol monopropyl ether, propylene glycol monomethyl ether, hexamethylene glycol, hexylene glycol, pentamethylene glycol, muguet alcohol, methyl β-phenylethyl alcohol, and methyl sandeflor. Further preferred examples thereof include 10-undecenol, 1-octen-3-ol, 2,6-nonadienol, 2-tert-butylcyclohexanol, 2-ethylhexanol, 2-heptanol, 3,5,5-trimethylhexanol, 3-octanol, 3-phenylpropyl alcohol, L-menthol, n-decyl alcohol, α-dimethylbenzyl alcohol, p-tert-butylcyclohexanol, p-methyldimethylbenzylcarbinol, α,3,3-trimethyl-2-norbornanemethanol, α-n-amylcinnamic alcohol, α-fenchyl alcohol, β-phenylethyl alcohol, anise alcohol, amber core, ambrinol, isononyl alcohol, isophytol, isopulegol, isoborneol, ethyllinalool, octanol, carveol, geraniol, santalol, cis-3-hexen-1-ol, cis-6-nonenol, citronellol, dihydro-α-terpineol, dihydrocitronellol, dihydromyrcenol, dihydrolinalool, dimethylphenylethylcarbinol, dimethylbenzylcarbinol, cinnamic alcohol, styrally alcohol, cedrol, terpineol, terpinen-4-ol, Timberol, tetrahydrogeraniol, tetrahydromyrcenol, tetrahydromugol, tetrahydrolinalool, nerol, nerolidol, nonanol, nonyl alcohol, nopol, hydrotropyl alcohol, Bacdanol, patchouli alcohol, farnesol, phytol, phenylethylmethylethylcarbinol, phenoxyethyl alcohol, furfuryl alcohol, vetivenol, perillaalcohol, benzyl alcohol, mayol, myrcenol, myrtenol, lavandulol, and linalool.

The phenols to be used as fragrances in the invention are not particularly limited as far as they are organic compounds which are phenolic compounds or derivatives thereof and have aroma or pleasant odor, and examples thereof include monovalent, divalent, or trivalent phenolic compounds, polyphenols, or ether derivatives thereof. Preferred examples thereof include p-cresol, isoeugenol, estragol, eugenol, hinokithiol, benzylisoeugenol, benzyleugenol, methylisoeugenol, methyleugenol, 2-methoxynaphthalene, 2,6-dimethoxyphenol, 4-ethylguaiacol, 4-methylguaiacol, 5-propenylguaetol, β-naphthol isobutyl ether, p-allylphenol, p-ethylphenol, isosafrol, ethylisoeugenol, catechol dimethyl ether, carvacrol, guaiacol, creosol, safrol, dihydroeugenol, thymol, chavicol, hydroquinone dimethyl ether, vanitrope, bromelia, methoxybenzene, resorcinol dimethyl ether, and shogaol.

The aldehydes or acetals to be used as fragrances in the invention are not particularly limited as far as they are volatile organic compounds having an aldehyde group or an acetal group in the molecule. Examples thereof include aliphatic aldehydes or acetals, terpene aldehydes or acetals, aromatic aldehydes or acetals, and the like. Preferred examples include 10-undecenal, 2,4-dimethyl-4,4a,5,9b-tetrahydroindeno[1,2d]-1,3-dioxine, 2,4-decadienal, 2,6-nonadienal, 2-butyl-4,4,6-trimethyl-1,3-dioxane, 2-hexyl-5-methyl-1,3-dioxolane, 2-methylundecanal, 2-methylundecanal dimethyl acetal, 3-ethyl-2,4-dioxaspiro[5.5]undec-8-ene, 3-ethyl-8(9),11-dimethyl-2,4-dioxaspiro[5.5]undec-8-ene, 3-propylbicyclo[2.2.1]-hept-5-ene-2-carboxyaldehyde, 4-isopropyl-5,5-dimethyl-1,3-dioxane, 4-heptenal, 5-methyl-5-propyl-2-(1-methylbutyl)-1,3-dioxane, o-methoxycinnamic aldehyde, o-methoxybenzaldehyde, p-tolylaldehyde, α-n-hexylcinnamic aldehyde, α-amylcinnamic aldehyde, acetaldehyde, acetaldehyde ethyl linalyl acetal, acetaldehyde diethyl acetal, anisaldehyde, aldehyde C-10, aldehyde C-11, aldehyde C-12, aldehyde C-6, aldehyde C-6 DEA, aldehyde C-6 DMA, aldehyde C-6 PG acetal, aldehyde C-8, aldehyde C-8 DEA, aldehyde C-8 DMA, aldehyde C-9, aldehyde C-9 DEA, aldehyde C-9 DMA, isocyclocitral, ethylvanillin, canthoxal, cucumber aldehyde, cumin aldehyde, geranial, cyclamen aldehyde, cis-6-nonenal, citral, citronellal, citronellyloxyacetaldehyde, cinensal, Dupical, trans-2-hexenal, trans-2-hexenal diethyl acetal, Triplal, neral, hydrotropaldehyde, vanillin, hydroxycitronellal, phenylacetaldehyde, phenylacetaldehyde P.G. acetal, phenylacetaldehyde dimethyl acetal, furfural, Floralozone, heliotropin, helional, perillaldehyde, bergamal, beltaldehyde, bernaldehyde, benzaldehyde, homo-myrac aldehyde, myrac aldehyde, melonal, lilal, lilial, 2,4,6- triisopropyl-1,3,5-trioxane, 2,4-undecadienal, 2,4-octadienal, 2,4-dioxa-3-methyl-7,10-methanospiro[5.5]-undecane, 2,4-dodecadienal, 2,4-nonadienal, 2,4-hexadienal, 2,4-heptadienal, 2,5,6-trimethyl-4-heptenal, 2,6,10-trimethyl-5,9-undecadienal, 2-methyl-3-(4-methylphenyl)-propanal, 2-methyl-4-(2,6,6-trimethyl-2-cyclohexenyl)-3-butenal, 2-methylbutanal, 3-phenylpropionic aldehyde, 3-phenylpropionic aldehyde dimethyl acetal, 3-methyl-5-phenylvaleraldehyde, 4-(2,2,6-trimethyl-2(1)-cyclohexane)-2-methylbutanal, 4-(4-methyl-3-cyclohexen-1-ylidene)-pentanal, 4-methyl-2-phenyl-2-pentenal, 5-(hydroxymethyl)-2-furfural, 5,9-dimethyl-4,9-decadienal, 5-methylfurfural, n-valeraldehyde, p-tert-butylhydrocinnamic aldehyde, p-isobutyl-α-methylhydrocinnamic aldehyde, p-isopropylhydrotropaldehyde, p-methylhydrotropaldehyde, p-methylphenylacetaldehyde, p-methylphenoxyacetaldehyde, p-methoxybenzaldehyde, α-n-amylcinnamic aldehyde diethyl acetal, α-amylcinnamic aldehyde dimethyl acetal, α-camphorenaldehyde, α-methylcinnamic aldehyde, β-methylhydrocinnamic aldehyde, γ-n-hexylcinnamic aldehyde, acetaldehyde ethyl isoeugenyl acetal, acetaldehyde ethyl cis-3-hexenyl acetal, acetaldehyde ethyl phenylethyl acetal, acetaldehyde ethyl hexyl acetal, acetaldehyde citronellyl ethyl acetal, acetaldehyde citronellyl methyl acetal, acetaldehyde phenylethyl n-propyl acetal, aldehyde C-13, aldehyde C-14, aldehyde C-5, aldehyde C-7, aldehyde C-7 DEA, aldehyde C-7 DMA, isovaleraldehyde, octahydro-4,7-methano-1H-indenecarboxyaldehyde, caryophyllenaldehyde, geranyloxyacetaldehyde, safranal, salicylaldehyde, cyclocitral, cis-3-hexenal, cis-3-hexenal diethyl acetal, cis-4-decenal, citral PG acetal, citral diethyl acetal, citral dimethyl acetal, citronellal EG acetal, dihydroindenyl-2,4-dioxane, dimethyloctanal, cinnamic aldehyde, decanal diethyl acetal, decanal dimethyl acetal, tetrahydrocitral, dodecanal dimethyl acetal, trans-2-undecenal, trans-2-decen-1-al, trans-2-dodecenal, trans-2-tridecenal, trans-2-nonenal, trans-2-heptenal, trans-2-pentenal, trans-4-decenal, trimethylundecenal, trimethyldecadienal, hydrotropaldehyde E.G. acetal, hydrotropaldehyde dimethyl acetal, vanillin P.G. acetal, paraldehyde, hydroxycitronellal diethyl acetal, phenylacetaldehyde 2,3-butylene glycol acetal, phenylacetaldehyde 2,4-dihydroxy-4-methylpentane acetal, phenylacetaldehyde diisobutyl acetal, phenoxyacetaldehyde, furfurylacrolein, heptanal E.G. acetal, heliotropin diethyl acetal, heliotropin dimethyl acetal, benzaldehyde PG acetal, benzaldehyde glyceryl acetal, benzaldehyde diethyl acetal, benzaldehyde dimethyl acetal, formaldehyde cyclododecyl ethyl acetal, methyldecanal, methylnonylacetaldehyde dimethyl acetal, methylvanillin, methoxydicyclopentadienecarboxyaldehyde, and methoxycitronellal. Further preferred examples include 10-undecenal, 2,4-dimethyl-4,4a,5,9b-tetrahydroindeno[1,2d]-1,3-dioxine, 2,4-decadienal, 2,6-nonadienal, 2-butyl-4,4,6-trimethyl-1,3-dioxane, 2-hexyl-5-methyl-1,3-dioxolane, 2-methylundecanal, 2-methylundecanal dimethyl acetal, 3-ethyl-2,4-dioxaspiro[5.5]undec-8-ene, 3-ethyl-8(9),11-dimethyl-2,4-dioxaspiro[5.5]undec-8-ene, 3-propylbicyclo[2.2.1]-hept-5-ene-2-carboxaldehyde, 4-isopropyl-5,5-dimethyl-1,3-dioxane, 4-heptenal, 5-methyl-5-propyl-2-(1-methylbutyl)-1,3-dioxane, o-methoxycinnamic aldehyde, o-methoxybenzaldehyde, p-tolylaldehyde, α-n-hexylcinnamic aldehyde, α-amylcinnamic aldehyde, acetaldehyde, acetaldehyde ethyl linalyl acetal, acetaldehyde diethyl acetal, anisaldehyde, aldehyde C-10, aldehyde C-11, aldehyde C-12, aldehyde C-6, aldehyde C-6 DEA, aldehyde C-6 DMA, aldehyde C-6 PG acetal, aldehyde C-8, aldehyde C-8 DEA, aldehyde C-8 DMA, aldehyde C-9, aldehyde C-9 DEA, aldehyde C-9 DMA, isocyclocitral, ethylvanillin, kantokisal, cucumber aldehyde, cumin aldehyde, geranial, cyclamen aldehyde, cis-6-nonenal, citral, citronellal, citronellyloxyacetaldehyde, cinensal, Dupical, trans-2-hexenal, trans-2-hexenal diethyl acetal, Triplal, neral, hydrotropaldehyde, vanillin, hydroxycitronellal, phenylacetaldehyde, phenylacetaldehyde P.G. acetal, phenylacetaldehyde dimethyl acetal, furfural, Floralozone, heliotropin, helional, perillaldehyde, bergamal, beltaldehyde, bernaldehyde, benzaldehyde, homo-myrac aldehyde, myrac aldehyde, melonal, lilal, and lilial.

The ketones or ketals to be used as fragrances in the invention are not particularly limited as far as they are volatile organic compounds having a ketone group or a ketal group in the molecule include aliphatic ketones or ketals, terpene ketones or ketals, aromatic ketones or ketals, and the like. Preferred examples include 2-sec-butylcyclohexanone, 2-acetyl-3,3-dimethylnorbornane, 2-acetyl-5-methylfuran, 2-acetylfuran, 2-butyl-1,4-dioxaspiro[4,4]nonane, 2-hexylcyclopentanone, 3-hydroxy-4,5-dimethyl-2-(5H)-furanone, 5-ethyl-3-hydroxy-4-methyl-2[5H]-furanone, 6-methyl-3,5-heptadien-2-one, d-pulegone, L-carvone, o-tert-butylcyclohexanone, p-tert-butylcyclohexanone, p-methylacetophenone, p-methoxyacetophenone, α-dinascone, α-fenchone, β-methylnaphthylketone, acetylcedrene, acetophenone, anisylacetone, allyl α-ionone, ionone, iso-E-super, isojasmone, isodamascone, isolongifolanone, irone, ethyl isoamyl ketone, ethylmaltol, Cashmeran, carone, camphor, Koavone, cyclotene, cis-jasmone, dihydrocarvone, dihydrojasmone, dibenzyl ketone, cedorenone, sotolone, damascone, damascenone, trimofix O, nootkatone, furaneol, plicatone, florex, vertfix, verbenone, benzophenone, maltol, methylionone, methylcyclopentenolone, methylheptenone, menthone, raspberry ketone, 1-(4-methoxyphenyl)-1-penten-3-one, 1-(p-menthen-6-yl)-1-propanone, 1-acetyl-3,3-dimethyl-1-cyclohexene, 2-(1-cyclohexen-1-yl)cyclohexanone, 2,2,5,5-tetramethyl-4-isopropyl-1,3-dioxane, 2,2,5-trimethyl-5-pentylcyclopentanone, 2,3,5-trimethylcyclohexen-4-yl-1-methyl ketone, 2,3-hexadione, 2,3-heptanedione, 2,3-pentadione, 2,4-di-tert-butylcyclohexanone, 2,5,5-trimethyl-2-phenyl-1,3-dioxane, 2,6,10-trimethyl-1-acetyl-2,5,9-cyclododecatriene, 2,6,6-trimethyl-2-cyclohexene-1,4-dione, 2-n-butylidene-3,5,5(3,3,5)-trimethylcyclohexanone, 2-n-heptylcycloheptanone, 2'-acetonaphthone, 2-undecanone, 2-octanone, 2-cyclopentylcyclopentanone, 2-tridecanone, 2-nonanone, 2-hydroxy-6-isopropyl-3-methyl-2-cyclohexenone, 2-butanone, 2-heptanone, 2-heptylcyclopentanone, 2-pentanone, 2-pentyl-2-cyclopentenone, 2-pentylcyclopentanone, 3,3-dimethylcyclohexyl methyl ketone, 3,4-dimethyl-1,2-cyclopentadione, 3,4-hexadione, 3,5-dimethyl-1,2-cyclopentadione, 3-acetyl-2,5-dimethylfuran, 3-octanone, 3-nonanone, 3-hydroxymethyl-2-nonanone, 3-hexanone, 3-heptanone, 3-hepten-2-one, 3-methyl-4-phenyl-3-buten-2-one, 3-methyl-5-(2,2,3-trimethyl-3-cyclopentenyl)-3-penten-2-one, 3-methyl-5-propyl-2-cyclohexenone, 4-(4-hydroxy-3-methoxyphenyl)-2-butanone, 4-(4-methoxyphenyl)-3-buten-2-one, 4(5)-acetyl-7,7,9-(7,9,9)-trimethylbicyclo[4.3.0]nona-1-ene, 4,7-dihydro-2-(3-pentanyl)-1,3-dioxepine, 4,7-dihydro-2-isoamyl-2-methyl-1,3-dioxiepine, 4-tert-amylcyclohexanone, 4-oxoisophorone, 4-cyclohexenyl-4-methyl-2-pentanone, 4-heptanone, 4-methyl-3-penten-2-one, 4-methyl-4-phenyl-2-pentanone, 4-methylene-3,5,6,6-tetramethyl-2-heptanone, 5-cyclohexadecen-1-one, 5-hydroxy-4-octanone, 5-phenyl-5-methyl-3-hexanone, 5-methyl-2,3-hexadione, 7-methyl-3,5-dihydro-2H-benzodioxepin-3-one, p-hydroxyphenylbutanone, p-methoxyphenylacetone, α-methylanisalacetone, acetylisovaleryl, acetyl caryophyllene, acetyldimethyltetrahydrobenzindane, acetoin, acetoketal, acetophenone neopentyl glycol acetal, acetone, atrinone, anisylidenacetone, amylcyclopentanone, ethyl acetoacetate E.G. ketal, ethyl acetoacetate propylene glycol acetal, oxocedrane, cryptone, geranylacetone, diacetyl, diacetone alcohol, diosphenol, cyclohexanone, cyclohexenone, cyclopentanone, cis-2-acetonyl-4-methyltetrahydropyran, dimethyloctenone, zingerol, cedranone, vitalide, piperitenone, piperitone, piperonylacetone, farnesylacetone, pseudoionone, butylideneacetone, furfural acetone, propiophenone, heliotropylacetone, verdoxane, benzylideneacetone, homofuraneol, mesityl oxide, methyl α-furyl ketone, methyl isopropyl ketone, methyliritone, methylcedorilone, and methyltetrahydrofuranone. Further preferred examples include 2-sec-butylcyclohexanone, 2-acetyl-3,3-dimethylnorbornane, 2-acetyl-5-methylfuran, 2-acetylfuran, 2-butyl-1,4-dioxaspiro[4,4]nonane, 2-hexylcyclopentanone, 3-hydroxy-4,5-dimethyl-2-(5H)-furanone, 5-ethyl-3-hydroxy-4-methyl-2 [5H]-furanone, 6-methyl-3,5-heptadien-2-one, d-pulegone, L-carvone, o-tert-butylcyclohexanone, p-tert-butylcyclohexanone, p-methylacetophenone, p-methoxyacetophenone, α-dinascone, α-fenchone, β-methylnaphthylketone, acetylcedrene, acetophenone, anisylacetone, allyl α-ionone, ionone, iso E super, isojasmone, isodamascone, isolongifolanone, irone, ethyl isoamyl ketone, ethylmaltol, Cashmeran, carone, camphor, Koavone, cyclotene, cis-jasmone, dihydrocarvone, dihydrojasmone, dibenzyl ketone, cedorenone, sotolone, damascone, damascenone, trimofix O, nootkatone, furaneol, plicatone, florex, vertfix, verbenone, benzophenone, maltol, methylionone, methylcyclopentenolone, methylheptenone, menthone, raspberry ketone.

The ethers to be used as fragrances in the invention are not particularly limited as far as they are volatile organic compounds having an ether group in the molecule. Examples thereof include aliphatic ethers, terpene ethers, aromatic ethers, and the like. Preferred examples include 1,4-cineol, 1,8-cineol, p-cresyl methyl ether, β-caryophyllene oxide, β-naphthyl isobutyl ether, β-naphthyl ethyl ether, β-naphthyl methyl ether, anethole, ambroxane, isoamyl phenylethyl ether, isobornyl methyl ether, grisalva, cyclamber, diphenyl oxide, cedrambar, cedryl methyl ether, teaspyran, nerol oxide, phenylethyl methyl ether, madrox, linalool oxide, limetol, Rhubofix, rhouboflor, rose oxide, rose furan, 13-oxabicyclo[10.3.0]pentadecane, 1-methylcyclododecyl methyl ether, 2,2,6-trimethyl-6-vinyltetrahydrofuran, 2,2-dimethyl-5-(1-methyl-1-propenyl)-tetrahydropyran, 2-ethylidene-6-isopropoxybicyclo[2.2.1]heptane, 2-oxaspiro[4.7]dodecane, 2-butyl-4,6-dimethyldihydropyran, 2-methyl-2-butenylphenyl ethyl ether, 3,3,5-trimethylcyclohexyl ethyl ether, 3-oxabicyclo[10.3.0]-pentadec-6-ene, 4-allylanisole, 5-isopropenyl-2-methyl-2-vinyltetrahydrofuran, 8,9-epoxycedrene, n-decyl vinyl ether, tert-butylhydroquinone dimethyl ether, α-cedrene epoxide, α-terpinyl methyl ether, allyl phenylethyl ether, isoamyl benzyl ether, isolongifolene epoxide, ethyl o-methoxybenzyl ether, ocimene epoxide, geranyl ethyl ether, cyclodecenyl methyl ether, cyclohexyl ethyl ether, cyclohexyl phenylethyl ether, citroxide, citroneryl ethyl ether, dibenzyl ether, juniparome, cedrol methyl ether, decyl methyl ether, tricyclodecenyl methyl ether, trimethylcyclododecatriene epoxide, methylphenyl ethyl ether, methyl hexyl ether, methyl benzyl ether, limonene oxide, 1,2-dimethoxybenzene, 1,3-dimethoxybenzene, 1,4-dimethoxy-2-tert-butylbenzene, ethylene glycol diethyl ether, ethylene glycol dibutyl ether, ethylene glycol dipropyl ether, ethylene glycol dimethyl ether, diethyl ether, diethylene glycol diethyl ether, diethylene glycol dibutyl ether, diethylene glycol dipropyl ether, diethylene glycol dimethyl ether, dimethyl ether, tetrahydrofuran, propylene glycol diethyl ether, and propylene glycol dimethyl ether. Further preferred examples thereof include 1,4-cineol, 1,8-cineol, p-cresyl methyl ether, β-caryophyllene oxide, β-naphthyl isobutyl ether, β-naphthyl ethyl ether, β-naphthyl methyl ether, anethole, ambroxane, isoamyl phenylethyl ether, isobornyl methyl ether, grisalva, cyclamber, diphenyl oxide, cedrambar, cedryl methyl ether, teaspyran, nerol oxide, phenylethyl methyl ether, madrox, linalool oxide, limetol, Rhubofix, rhouboflor, rose oxide, and rose furan.

The synthetic musks to be used as fragrances in the invention are not particularly limited as far as they are organic compounds having musk odor or musk-like odor and examples thereof include 10-oxahexadecanolide, 11-oxahexadecanolide, 12-oxahexadecanolide, ambrettolide, Ambreton, exaltolide, exaltone, Galaxolide, cyclohexadecanolide, cyclopentadecanolide, cyclopentadecanone, civetone, cervolide, celestolide, Tonalide, fantolide, pentalide, formylethyltetramethyltetralin, muscone, versalide, and the like.

The acids to be used as fragrances in the invention are not particularly limited as far as they are organic compounds having a carboxyl group in the molecule and examples thereof include phenylacetic acid, 2-ethylbutyric acid, 2-ethylhexanoic acid, 2-decenoic acid, 2-hexenoic acid, 2-methyl-2-pentenoic acid, 2-methylbutyric acid, 2-methylheptanoic acid, 4-pentenoic acid, 4-methylpentanoic acid, undecanoic acid, undecylenic acid, octanoic acid, oleic acid, geranic acid, cinnamic acid, stearic acid, tiglic acid, decanoic acid, dodecanoic acid, tridecanoic acid, nonanoic acid, hydrocinnamic acid, pyruvic acid, propionic acid, hexanoic acid, heptanoic acid, myristic acid, lactic acid, linolic acid, linoleic acid, levulinic acid, oxalic acid, glutalic acid, citric acid, succinic acid, tartaric acid, terephthalic acid, vanillic acid, valine, phytic acid, fumaric acid, benzoic acid, malic acid, maleic acid, malonic acid, and the like.

The lactones to be used as fragrances in the invention are not particularly limited as far as they are organic compounds having a lactone group in the molecule and examples thereof include aliphatic lactones, terpene lactones, aromatic lactones, and the like. Preferred examples thereof include 6-methylcoumarin, α-angelica lactone, γ-n-butyrolactone, γ-undecalactone, γ-octalactone, γ-decalactone, γ-nonalactone, γ-valerolactone, γ-hexylactone, γ-heptalactone, δ-2-decenolactone, δ-undecalactone, δ-octalactone, δ-decalactone, δ-tetradecalactone, δ-dodecalactone, δ-tridecalactone, δ-nonalactone, δ-hexylactone, ε-decalactone, ε-dodecalactone, aldehyde C-14 (peach), aldehyde C-18 (coconut), whisky lactone, dihydrojasmone lactone, jasmine lactone, jasmolactone, methyl γ-decalactone, menthalactone, 4,6,6(4, 4,6)-trimethyltetrahydropyran-2-one, 7-decene-1,4-lactone, octahydrocoumarin, dihydrocoumarin, dodecalactone, 3-n-butylidenephthalide, 3-n-butylphthalide, 3-propylidenephthalide, and 3-propylphthalide.

The esters to be used as fragrances in the invention are not particularly limited as far as they are volatile organic compounds having an ester group in the molecule and examples thereof include aliphatic esters, terpene esters, aromatic esters, and the like. Preferred examples thereof include 1-ethynylcyclohexyl acetate, 1-octen-3-yl acetate, 2-ethylhexyl acetate, 2-phenoxyethyl isobutyrate, 2-phenoxyethyl propionate, 3,5,5-trimethylhexyl acetate, 3,7-dimethyloctanyl acetate, 3-phenylpropyl acetate, 9-decen-1-yl acetate, L-menthyl acetate, L-menthyl propionate, o-tert-butylcyclohexyl acetate, p-tert-butylcyclohexyl acetate, p-cresyl acetate, p-cresyl isobutyrate, p-cresyl phenylacetate, acetylisoeugenol, acetyleugenol, anisyl acetate, aphermate, amyl acetate, amyl caprylate, amyl caproate, amyl salicylate, amyl valerate, amyl butyrate, amyl formate, allyl 2-ethylbutyrate, allylamyl glycolate, allyl isovalerate, allyl octanoate, allyl caprylate, allyl caproate, allyl cyclohexylacetate, allyl cyclohexyloxyacetate, allyl cyclohexylbutyrate, allyl cyclohexylpropionate, allyl cinnamate, allyl phenoxyacetate, allyl butyrate, allyl heptanoate, allyl benzoate, aldehyde C-16 (strawberry), aldehyde C-19 (pineapple), aldehyde C-20 (raspberry), isoamyl acetate, isoamyl angelate, isoamyl isovalerate, isoamyl isobutyrate, isoamyl undecylenate, isoamyl octanoate, isoamyl salicylate, isoamyl cinnamate, isoamyl decanoate, isoamyl dodecanoate, isoamyl butyrate, isoamyl propionate, isoamyl hexanoate, isoamyl heptyne carbonate, isoamyl benzoate, isoamyl formate, isoamyl levulinate, isoeugenyl phenylacetate, isodihydrolavandulyl acetate, isobutyl acetate, isobutyl isovalerate, isobutyl isobutyrate, isobutyl salicylate, isobutyl cinnamate, isobutyl valerate, isobutyl phenylacetate, isobutyl butyrate, isobutyl propionate, isobutyl hexanoate, isobutyl benzoate, isopulegyl acetate, isopropyl acetate, isopropyl isovalerate, isopropyl isobutyrate, isopropyl cinnamate, isopropyl decanoate, isopropyl phenylacetate, isopropyl butyrate, isopropyl hexanoate, isopropyl benzoate, isopropyl myristate, isobornyl acetate, isobornyl propionate, Winter Green, ethyl 2-tert-butylcyclohexyl carbonate, ethyl 2-ethylhexanoate, ethyl 2-octenoate, ethyl 2-decenoate, ethyl 2-furoate, ethyl 2-hexylacetoacetate, ethyl 2-benzylacetoacetate, ethyl 2-methylvalerate, ethyl 2-methylbutyrate, ethyl 3,5,5-trimethylhexanoate, ethyl 3-hydroxybutyrate, ethyl 3-hydroxyhexanoate, ethyl 3-hydroxy-3-phenylpropionate, ethyl 3-phenylglycidate, ethyl 3-phenylpropionate, ethyl o-methoxybenzoate, ethyl p-anisate, ethyl acetate, ethyl acetoacetate, ethyl isovalerate, ethyl isobutyrate, ethyl octyne carbonate, ethyl oleate, ethyl caprinate, ethyl caprylate, ethyl caproate, ethyl crotonate, ethyl geranate, ethyl safranate, ethyl salicylate, ethyl cyclogeraniate, ethyl cinnamate, ethyl valerate, ethyl phenylacetate, ethyl butyrate, ethyl propionate, ethyl heptanoate, ethyl heptyne carbonate, ethyl pelargonate, ethyl benzoate, ethyl formate, ethyl myristate, ethyl methyl p-tolylglycidate, ethyl methyl phenylglycidate, ethyl laurate, ethyl lactate, ethyl linalylacetate, ethyl levulinate, ethylene dodecanedioate, ethylene brassylate, eugenyl phenylacetate, octyl acetate, octyl isovalerate, octyl isobutyrate, octyl octanoate, octyl butyrate, octyl heptanoate, octyl formate, ocimenyl acetate, caryophyllen acetate, caryophyllen formate, calyxol, carvyl acetate, guaiac acetate, cuminyl acetate, geranyl acetate, geranyl isovalerate, geranyl isobutylate, geranyl tiglate, geranyl phenylacetate, geranyl butyrate, geranyl propionate, geranyl hexanoate, geranyl benzoate, geranyl formate, coniferin, santaryl acetate, diethyl adipate, diethyl succinate, diethyl sebacate, diethyl tartrate, diethyl phthalate, diethyl malonate, cyclohexyl acetate, cyclohexyl isovalerate, cyclohexylethyl acetate, cyclohexyl crotonate, cyclohexyl butyrate, cis-3-hexenyl 2-methylbutyrate, cis-3-hexenyl acetate, cis-3-hexenyl angelate, cis-3-hexenyl isovalerate, cis-3-hexenyl isobutyrate, cis-3-hexenyl caproate, cis-3-hexenyl salicylate, cis-3-hexenyl tiglate, cis-3-hexenyl valerate, cis-3-hexenyl phenylacetate, cis-3-hexenyl butyrate, cis-3-hexenyl propionate, cis-3-hexenyl benzoate, cis-3-hexenyl formate, cis-3-hexenyl lactate, citryl acetate, citronellyl acetate, citronellyl isovalerate, citronellyl isobutyrate, citronellyl tiglate, citronellyl phenylacetate, citronellyl butylate, citronellyl propionate, citronellyl hexanoate, citronellyl formate, dihydrocarvyl acetate, dihydrocuminyl acetate, dihydroterpinyl acetate, dihydromyrcenyl acetate, dimethyl succinate, dimethylphenylethylcarbinyl acetate, dimethyl phthalate, dimethylbenzylcarbinyl acetate, dimethylbenzylcarbinyl isobutyrate, dimethylbenzylcarbinyl butyrate, dimethylbenzylcarbinyl propionate, jasmal, cinnamyl acetate, cinnamyl isovalerate, cinnamyl isobutyrate, cinnamyl cinnamate, cinnamyl tiglate, cinnamyl butyrate, cinnamyl propionate, cinnamyl benzoate, cinnamyl formate, styrallyl acetate, styrallyl isobutyrate, styrallyl propionate, cedryl acetate, cedryl formate, terpinyl acetate, terpinyl isovalerate, terpinyl isobutyrate, terpinyl butyrate, terpinyl propionate, terpinyl formate, decahydro-β-naphthyl formate, decyl acetate, tetrahydrofurfuryl butyrate, tetrahydrogeranyl acetate, tetrahydrofurfuryl acetate, tetrahydromugyl acetate, tetrahydrolinalyl acetate, dodecyl acetate, trans-2-hexenyl acetate, trans-2-hexenyl butyrate, trans-2-hexenyl propionate, trans-2-hexenyl hexanoate, trans-decahydro-β-naphthyl acetate, trans-decahydro-β-naphthyl isobutyrate, triacetin, triethyl citrate, tricyclodecyl acetate, tricyclodecenyl acetate, tricyclodecenyl isobutyrate, tricyclodecenyl propionate, neryl acetate, neryl isobutyrate, neryl butyrate, neryl propionate, neryl formate, nonyl acetate, nopyl acetate, hydrotropic acetate, phenylethyl 2-methylbutyrate, phenylethyl acetate, phenylethyl angelate, phenylethyl isovalerate, phenylethyl isobutyrate, phenylethyl caprylate, phenylethyl salicylate, phenylethyl cinnamate, phenylethyl tiglate, phenylethyl nonanoate, phenylethyl valerate, phenylethyl pivalate, phenylethyl phenylacetate, phenylethyl butyrate, phenylethyl propionate, phenylethyl benzoate, phenylethyl formate, phenylethyl methacrylate, phenylethylmethylethylcarbinyl acetate, phenyl salicylate, fenchyl acetate, butyl acetate, butyl angelate, butyl isovalerate, butyl isobutyrate, butyl octanoate, butyl salicylate, butyl decanoate, butyl dodecanoate, butyl valerate, butyl phenylacetate, butyl butyryllactate, butyl butyrate, butyl propionate, butyl hexanoate, butyl levulinate, furfuryl acetate, prenyl acetate, prenyl angelate, prenyl benzoate, propyl acetate, propyl isovalerate, propyl isobutyrate, propyl octanoate, propyl cinnamate, propyl trans-2, cis-4-decadienoate, propyl phenylacetate, propyl butyrate, propyl propionate, propyl hexanoate, propyl heptanoate, propyl benzoate, propyl formate, hexyl 2-methylbutyrate, hexyl acetate, hexyl isovalerate, hexyl isobutyrate, hexyl octanoate, hexyl salicylate, hexyl tiglate, hexyl phenylacetate, hexyl butyrate, hexyl propionate, hexyl hexanoate, hexyl benzoate, hexyl formate, veticol acetate, vetiveryl acetate, heptyl acetate, heptyl octanoate, heptyl butyrate, heptyl hexanoate, heliotropyl acetate, benzyl 2-methylbutyrate, benzyl acetate, benzyl isovalerate, benzyl isobutyrate, benzyl caprylate, benzyl salicyalte, benzyl cinnamate, benzyl tiglate, benzyl dodecanoate, benzyl valerate, benzyl phenylacetate, benzyl butyrate, benzyl propionate, benzyl hexanoate, benzyl benzoate, benzyl formate, pentyl salicylate, myraldyl acetate, myrcenyl acetate, myrtenyl acetate, methyl 1-methyl-3-cyclohexenecarboxylate, methyl 2-nonenoate, methyl 2-furoate, methyl 2-methylbutyrate, methyl 3-nonenoate, methyl 9-undecenoate, methyl o-methoxybenzoate, methyl acetate, methyl atrarate, methyl anisate, methyl angelate, methyl isovalerate, methyl isobutyrate, methyl isohexanoate, methyl octanoate, methyl octyne carbonate, methyl oleate, methyl caprinate, methyl caprylate, methyl caproate, methyl geranate, methyl salicylate, methyl cyclooctyl carbonate, methyl cyclogeranate, methyl cyclopentylideneacetate, methyl dihydrojasmonate, methyl jasmonate, methyl cinnamate, methyl decanoate, methyl decyne carbonate, methyl tetradecanoate, methyl dodecanoate, methyl trans-2-hexenoate, methyl trans-3-hexenoate, methyl nonanoate, methyl hydroxyhexanoate, methyl valerate, methyl phenylacetate, methyl phenylglycidate, methyl butyrate, methyl heptanoate, methyl heptyne carbonate, methyl pelargonate, methyl benzoate, methyl myristate, methyl laurate, methyl lactate, lavandulyl acetate, linalyl acetate, linalyl isovalerate, linalyl isobutyrate, linalyl octanoate, linalyl cinnamate, linalyl butyrate, linalyl propionate, linalyl hexanoate, linalyl benzoate, linalyl formate, rosamusk, rosephenone, rhodinyl acetate, rhodinyl isobutyrate, rhodinyl phenylacetate, rhodinyl butyrate, rhodinyl propionate, rhodinyl formate, 1,3-dimethyl-3-butenyl isobutyrate, 1-acetoxy-2-sec-butyl-1-vinylcyclohexane, 1-cyclohex-1-ene isopropylacetate, 2,4-dimethyl-3-cyclohexylmethyl acetate, 2,4-hexadienyl isobutyrate, 2-methyl-2-methylpentyl valerate, 2-methylbutyl acetate, 2-methylbutyl isovalerate, 3-octyl acetate, 3-phenylpropyl isovalerate, 3-phenylpropyl isobutyrate, 3-phenylpropyl propionate, 3-methylpentyl angelate, 4-methylbenzyl acetate, 5-methyl-3-butyltetrahydropyran-4-yl acetate, 6,10-dimethyl-5,9-undecatrien-2-yl acetate, 9-decen-1-yl propionate, E.G. diacetate, E.G. monobutyl ether acetate, L-carvyl propionate, L-perillyl acetate, L-bornyl propionate, L-menthyl isovalerate, L-menthyl phenylacetate, P.G. dibutyrate, P.G. dipropionate, p-cresyl caprylate, p-cresyl salicylate, α-amylcinnamyl acetate, acetylvanillin, anisyl propionate, anisyl formate, isobutyl 2-furanpropionate, isobutyl angelate, isobutyl crotonate, ethyl acrylate, ethyl citronellyl oxalate, ethyl stearate, ethyl tiglate, ethyl decadienoate, ethyl dehydrocyclogeranate, ethyl dodecanoate, ethyl trans-2-hexanoate, ethyl trans-3-hexanoate, ethyl nonanoate, ethyl palmitate, ethyl valerate, ethyl pyruvate, eugenyl formate, oxyoctalin formate, nerolidyl acetate, nonanediol-1,3-diacetate, phenyl glycol diacetate, pseudolinalyl acetate, butyl 10-undecenoate, butyl stearate, butyl formate, butyl lactate, furfuryl valerate, and propyl 2-furanacrylate. Further preferred examples include 1-ethynylcyclohexyl acetate, 1-octen-3-yl acetate, 2-ethylhexyl acetate, 2-phenoxyethyl isobutyrate, 2-phenoxyethyl propionate, 3,5,5-trimethylhexyl acetate, 3,7-dimethyloctanyl acetate, 3-phenylpropyl acetate, 9-decen-1-yl acetate, L-menthyl acetate, L-menthyl propionate, o-tert-butylcyclohexyl acetate, p-tert-butylcyclohexyl acetate, p-cresyl acetate, p-cresyl isobutyrate, p-cresyl phenylacetate, acetylisoeugenol, acetyleugenol, anisyl acetate, aphermate, amyl acetate, amyl caprylate, amyl caproate, amyl salicylate, amyl valerate, amyl butyrate, amyl formate, allyl 2-ethylbutyrate, allylamyl glycolate, allyl isovalerate, allyl octanoate, allyl caprylate, allyl caproate, allyl cyclohexylacetate, allyl cyclohexyloxyacetate, allyl cyclohexylbutyrate, allyl cyclohexylpropionate, allyl cinnamate, allyl phenoxyacetate, allyl butyrate, allyl heptanoate, allyl benzoate, aldehyde C-16 (strawberry), aldehyde C-19 (pineapple), aldehyde C-20 (raspberry), isoamyl acetate, isoamyl angelate, isoamyl isovalerate, isoamyl isobutyrate, isoamyl undecylenate, isoamyl octanoate, isoamyl salicylate, isoamyl cinnamate, isoamyl decanoate, isoamyl dodecanoate, isoamyl butyrate, isoamyl propionate, isoamyl hexanoate, isoamyl heptyne carbonate, isoamyl benzoate, isoamyl formate, isoamyl levulinate, isoeugenyl phenylacetate, isodihydrolavandulyl acetate, isobutyl acetate, isobutyl isovalerate, isobutyl isobutyrate, isobutyl salicylate, isobutyl cinnamate, isobutyl valerate, isobutyl phenylacetate, isobutyl butyrate, isobutyl propionate, isobutyl hexanoate, isobutyl benzoate, isopulegyl acetate, isopropyl acetate, isopropyl isovalerate, isopropyl isobutyrate, isopropyl cinnamate, isopropyl decanoate, isopropyl phenylacetate, isopropyl butyrate, isopropyl hexanoate, isopropyl benzoate, isopropyl myristate, isobornyl acetate, isobornyl propionate, ethyl 2-tert-butylcyclohexyl carbonate, ethyl 2-ethylhexanoate, ethyl 2-octenoate, ethyl 2-decenoate, ethyl 2-furoate, ethyl 2-hexylacetoacetate, ethyl 2-benzylacetoacetate, ethyl 2-methylvalerate, ethyl 2-methylbutyrate, ethyl 3,5,5-trimethylhexanoate, ethyl 3-hydroxybutyrate, ethyl 3-hydroxyhexanoate, ethyl 3-hydroxy-3-phenylpropionate, ethyl 3-phenylglycidate, ethyl 3-phenylpropionate, ethyl o-methoxybenzoate, ethyl p-anisate, ethyl acetate, ethyl acetoacetate, ethyl isovalerate, ethyl isobutyrate, ethyl octyne carbonate, ethyl oleate, ethyl caprinate, ethyl caprylate, ethyl caproate, ethyl crotonate, ethyl geranate, ethyl safranate, ethyl salicylate, ethyl cyclogeraniate, ethyl cinnamate, ethyl valerate, ethyl phenylacetate, ethyl butyrate, ethyl propionate, ethyl heptanoate, ethyl heptyne carbonate, ethyl pelargonate, ethyl benzoate, ethyl formate, ethyl myristate, ethyl methyl p-tolylglycidate, ethyl methyl phenylglycidate, ethyl laurate, ethyl lactate, ethyl linalylacetate, ethyl levulinate, ethylene dodecanedioate, ethylene brassylate, eugenyl phenylacetate, octyl acetate, octyl isovalerate, octyl isobutyrate, octyl octanoate, octyl butyrate, octyl heptanoate, octyl formate, ocimenyl acetate, caryophyllen acetate, caryophyllen formate, carvyl acetate, guaiac acetate, cuminyl acetate, geranyl acetate, geranyl isovalerate, geranyl isobutylate, geranyl tiglate, geranyl phenylacetate, geranyl butyrate, geranyl propionate, geranyl hexanoate, geranyl benzoate, geranyl formate, coniferin, santaryl acetate, diethyl adipate, diethyl succinate, diethyl sebacate, diethyl tartrate, diethyl phthalate, diethyl malonate, cyclohexyl acetate, cyclohexyl isovalerate, cyclohexylethyl acetate, cyclohexyl crotonate, cyclohexyl butyrate, cis-3-hexenyl 2-methylbutyrate, cis-3-hexenyl acetate, cis-3-hexenyl angelate, cis-3-hexenyl isovalerate, cis-3-hexenyl isobutyrate, cis-3-hexenyl caproate, cis-3-hexenyl salicylate, cis-3-hexenyl tiglate, cis-3-hexenyl valerate, cis-3-hexenyl phenylacetate, cis-3-hexenyl butyrate, cis-3-hexenyl propionate, cis-3-hexenyl benzoate, cis-3-hexenyl formate, cis-3-hexenyl lactate, citryl acetate, citronellyl acetate, citronellyl isovalerate, citronellyl isobutyrate, citronellyl tiglate, citronellyl phenylacetate, citronellyl butylate, citronellyl propionate, citronellyl hexanoate, citronellyl formate, dihydrocarvyl acetate, dihydrocuminyl acetate, dihydroterpinyl acetate, dihydromyrcenyl acetate, dimethyl succinate, dimethylphenylethylcarbinyl acetate, dimethyl phthalate, dimethylbenzylcarbinyl acetate, dimethylbenzylcarbinyl isobutyrate, dimethylbenzylcarbinyl butyrate, dimethylbenzylcarbinyl propionate, jasmal, cinnamyl acetate, cinnamyl isovalerate, cinnamyl isobutyrate, cinnamyl cinnamate, cinnamyl tiglate, cinnamyl butyrate, cinnamyl propionate, cinnamyl benzoate, cinnamyl formate, styrallyl acetate, styrallyl isobutyrate, styrallyl propionate, cedryl acetate, cedryl formate, terpinyl acetate, terpinyl isovalerate, terpinyl isobutyrate, terpinyl butyrate, terpinyl propionate, terpinyl formate, decahydro-β-naphthyl formate, decyl acetate, tetrahydrofurfuryl butyrate, tetrahydrogeranyl acetate, tetrahydrofurfuryl acetate, tetrahydromugyl acetate, tetrahydrolinalyl acetate, dodecyl acetate, trans-2-hexenyl acetate, trans-2-hexenyl butyrate, trans-2-hexenyl propionate, trans-2-hexenyl hexanoate, trans-decahydro-β-naphthyl acetate, trans-decahydro-β-naphthyl isobutyrate, triacetin, triethyl citrate, tricyclodecyl acetate, tricyclodecenyl acetate, tricyclodecenyl isobutyrate, tricyclodecenyl propionate, neryl acetate, neryl isobutyrate, neryl butyrate, neryl propionate, neryl formate, nonyl acetate, nopyl acetate, hydrotropic acetate, phenylethyl 2-methylbutyrate, phenylethyl acetate, phenylethyl angelate, phenylethyl isovalerate, phenylethyl isobutyrate, phenylethyl caprylate, phenylethyl salicylate, phenylethyl cinnamate, phenylethyl tiglate, phenylethyl nonanoate, phenylethyl valerate, phenylethyl pivalate, phenylethyl phenylacetate, phenylethyl butyrate, phenylethyl propionate, phenylethyl benzoate, phenylethyl formate, phenylethyl methacrylate, phenylethylmethylethylcarbinyl acetate, phenyl salicylate, fenchyl acetate, butyl acetate, butyl angelate, butyl isovalerate, butyl isobutyrate, butyl octanoate, butyl salicylate, butyl decanoate, butyl dodecanoate, butyl valerate, butyl phenylacetate, butyl butyryllactate, butyl butyrate, butyl propionate, butyl hexanoate, butyl levulinate, furfuryl acetate, prenyl acetate, prenyl angelate, prenyl benzoate, propyl acetate, propyl isovalerate, propyl isobutyrate, propyl octanoate, propyl cinnamate, propyl trans-2, cis-4-decadienoate, propyl phenylacetate, propyl butyrate, propyl propionate, propyl hexanoate, propyl heptanoate, propyl benzoate, propyl formate, hexyl 2-methylbutyrate, hexyl acetate, hexyl isovalerate, hexyl isobutyrate, hexyl octanoate, hexyl salicylate, hexyl tiglate, hexyl phenylacetate, hexyl butyrate, hexyl propionate, hexyl hexanoate, hexyl benzoate, hexyl formate, veticol acetate, vetiveryl acetate, heptyl acetate, heptyl octanoate, heptyl butyrate, heptyl hexanoate, heliotropyl acetate, benzyl 2-methylbutyrate, benzyl acetate, benzyl isovalerate, benzyl isobutyrate, benzyl caprylate, benzyl salicyalte, benzyl cinnamate, benzyl tiglate, benzyl dodecanoate, benzyl valerate, benzyl phenylacetate, benzyl butyrate, benzyl propionate, benzyl hexanoate, benzyl benzoate, benzyl formate, pentyl salicylate, myraldyl acetate, myrcenyl acetate, myrtenyl acetate, methyl 1-methyl-3-cyclohexenecarboxylate, methyl 2-nonenoate, methyl 2-furoate, methyl 2-methylbutyrate, methyl 3-nonenoate, methyl 9-undecenoate, methyl o-methoxybenzoate, methyl acetate, methyl atrarate, methyl anisate, methyl angelate, methyl isovalerate, methyl isobutyrate, methyl isohexanoate, methyl octanoate, methyl octyne carbonate, methyl oleate, methyl caprinate, methyl caprylate, methyl caproate, methyl geranate, methyl salicylate, methyl cyclooctyl carbonate, methyl cyclogeranate, methyl cyclopentylideneacetate, methyl dihydrojasmonate, methyl jasmonate, methyl cinnamate, methyl decanoate, methyl decyne carbonate, methyl tetradecanoate, methyl dodecanoate, methyl trans-2-hexanoate, methyl trans-3-hexenoate, methyl nonanoate, methyl hydroxyhexanoate, methyl valerate, methyl phenylacetate, methyl phenylglycidate, methyl butyrate, methyl heptanoate, methyl heptyne carbonate, methyl pelargonate, methyl benzoate, methyl myristate, methyl laurate, methyl lactate, lavandulyl acetate, linalyl acetate, linalyl isovalerate, linalyl isobutyrate, linalyl octanoate, linalyl cinnamate, linalyl butyrate, linalyl propionate, linalyl hexanoate, linalyl benzoate, linalyl formate, rosamusk, rosephenone, rhodinyl acetate, rhodinyl isobutyrate, rhodinyl phenylacetate, rhodinyl butyrate, rhodinyl propionate, and rhodinyl formate.

The halogen-containing compounds to be used as fragrances in the invention are not particularly limited as far as they are harogenide having aroma or pleasant odor, and examples thereof include p-dichlorobenzene and bromostyrol.

The fragrance materials of natural origin to be used as fragrances in the invention are not particularly limited and examples thereof include almond oil, anise oil, abies-far oil, *amyris* oil, *angelica* oil, ambergris tincture, amber sage, ambret seed oil, ylang-ylang oil, incense oil, winter green oil, elemi oil, oak moth absolute, oak moth essence, oak moth oil, opoponax oil, orris absolute, orange oil, orange flower absolute, cascarilla oil, castoreum resinoid, *cassia* china oil, *cassia* absolute, *cassia* oil, *cananga* java oil, chamomile oil blue, chamomile oil, *calamus* oil, cardamom oil, galbanum oil, caraway oil, guaiac wood oil, guaiac oil, cumin oil, clove boulbon oil, clove oil, *costus* oil, copaiba balsam, copaiba oil, coriander oil, cypress oil, sandalwood oil, cystlabdanum oil, ceder wood oil, citronella oil, civet absolute, jasmine absolute, juniper berry oil, camphor oil, jonquille absolute, ginger oil, ginger grass oil, cinnamon Ceylon oil, sweet fennel oil, *styrax* oil, spike lavender oil, spearmint oil, sage oil, sage clary oil, *geranium* oil, *geranium* grass oil, *geranium* Bourbon oil, celery oil, thyme oil, tarragon oil, tangerine oil, tuberose absolute, tolu balsam oil, *Diptheryx odorata* oil, nutmeg oil, narcissus absolute, neroli bigarado oil, verbena oil, violet leaves absolute, pine oil, basil oil, parsley seed oil, patchouli oil, vanilla oil, vanilla resinoid, hyssop oil, bitter almond oil, bitter fennel oil, Hinoki oil, hiba oil, pimento berry oil, hyacinth absolute, petit-grain oil, buchu oil, bay oil, petit-grain grass oil, petit-grain Paraguay oil, petit-grain bergamot oil, petit-grain mandarin, petit-grain lemon oil, vetiver oil Java, vetiver Bourbon, pennyroyal oil, pepper oil, peppermint oil, Peru balsam, Peru balsam oil, bergamot oil, benzoin oil, benzoin resinoid, bois de rose oil, ho oil, horwood oil, marjoram oil, mandarin oil, mimosa absolute, mil oil, musk tonkin tincture, mace oil, merrissa oil, *eucalyptus* oil, lime oil, lavandine oil, labdanum oil, lavender oil, roux oil, lemon oil, lemongrass oil, rose do mai, rose Bulgar oil, rosemary oil, Roman chamomile oil, laurel oil, and lovage oil. These natural materials can be used in various forms such as essential oils, resinoids, balsams, absolutes, concretes, and tinctures.

The following show chemical names of the trade names and general names in the above materials.

Dupical (Quest); 4-(tricyclo[5.2.1.02,6]decylidene-8)butanal.
Jasmal; 3-pentyltetrahydropyran-4-yl acetate.
Aphermate (IFF); α,3,3-trimethylcyclohexanemethyl formate.
Floralozon (IFF); p-ethyl-α,α-dimethylhydrocinnamaldehyde.
Cyclogalbanate (Dragoco); allyl cyclohexyloxyacetate.
Estragole; methyl chavicol.
Rhubofix (Firmenich); an isomeric mixture of spiro[1,4-methanonaphthlene-2(1H), 2'-oxirane],3,4,4a,5,8,8a,-hexahydro-3',7-dimethyl (1) and spiro[1,4-methanonaphthalene-(2H), 2'-oxiran],3,4,4a,5,8,8a-hexahydro-3',6-dimethyl (2).
Triplal (IFF); dimethyl tetrahydrobenzaldehyde.
Koavone (IFF); 4-methylene-3,5,6,6-tetramethyl-2-heptanone.
Limetol; 2,2,6-trimethyl-6-vinyl tetrahydropyran.
Ambroxan (Henkel); decahydro-3a,6,6,9a-tetramethyl-naphtho[2.1-b]furan.
Damascone; α-damascone, β-damascone, γ-damascone, δ-damascone.
Damascenone; α-damascenone, β-damascenone, γ-damascenone.
Ionone; α-ionone, β-ionone, γ-ionone.
Methylionone; α-n-methylionone, β-n-methylionone, γ-n-methylionone, α-iso-methylionone, β-iso-methylionone, γ-iso-methylionone.
Sandal: bacdanol (IFF); 2-ethyl-4-(2,2,3-trimethyl-3-cyclopenten-1-yl)-2-buten-1-ol,
Brahamanol (Dragoco); 2-methyl-4-(2,2,3-trimethyl-3-cyclopenten-1-yl)butanol,
Madranol (Dragoco); β-2,2,3-tetramethyl-3-Cyclopentenyl-2-butenol,
Sandalore (Givaudan); 3-methyl-5-(2,2,3-trimethylcyclopent-3-en-1-yl)-pentan-2-ol,
3,3-dimethyl-5-(2,2,3-trimethylcyclopenten-1-yl)-pent-4-en-2-ol,
Methyl sandeflor (TPC); 2-methyl-1-(methylbicyclo[2.2.1]-hept-5-en-2-yl)-penten-3-ol,
Sandeol (MS), and the like.
Musk: Cashmeran (IFF); 1,2,3,5,6,7-hexahydro-1,1,2,3,3-pentamethyl-4H-inden-4-one,
Galaxolide (IFF); 1,3,4,6,7,8-hexahydro-4,6,6,7,8,8-hexamethyl cyclopenta-γ-2-benzopyran,
Tonalid (PFW); 6-acetyl-1,1,2,4,4,7-hexamethyl tetrahydro naphthalene, phantolid; 5-acetyl-1,1,2,3,3,6-hexamethyl indan,
versalide; 7-acetyl-1,1,4,4-tetramethyl-6-ethyl-1,2,3,4-tetrahydro-naphthalene,
exaltolide; oxacyclohexadecan-2-one,
exaltone; cyclopentadecanone,
oxalide; 10-oxahexadecanolide,
12-oxahexadecanolide, ethylenebrassylate,
celestolide (IFF); 4-acetyl-6-tert-butyl-1,1-dimethylindan,
Traseolide (Quest); 5-aceytl-3-isopropyl-1,1,2,6-tetramethyl indan,
ethylenedodecanedioate, 5-cyclohexadecen-1-one, and the like.
Iso-E-Super (IFF); 7-acetyl-1,2,3,4,5,6,7,8-octahydro-1,1,6,7-tetramethyl-naphthalene.
Timberol (Dragoco); 1-(2,2,6-trimethylcyclohexan-1-yl)-hexan-3-ol.
Irone; α-irone, β-irone, γ-irone.
α-Dynascone (Firmenich); 1-(5,5-dimethylcyclohexen-1-yl)-4-penten-1-one.

Furthermore, in addition to the above flavors and fragrances, use can be made of flavors and fragrances described in "Nippon niokeru Shokuhin Koryo Kagoubutsu no Siyou Jittai Chosa" (2000$^{th}$ Kosei Kagaku Kenkyu Hokokusho; Nihon Koryo Kogyokai, published on March, 2001), "Gosei koryo—Kgaku to Shohin Chisiki" (published on Mar. 6, 1996, written by Motoichi Indoh, The Chemical Daily Co., Ltd.), "Perfume and Flavor Chemicals (Aroma Chemicals) 1, 2" (Steffen Arctender (1969)).

These flavors and fragrances may be used solely or as mixtures of two or more of them.

As these substances, commercially available substances can be also used. Moreover, as a single substance, a synthetic substance or substance which purified from a natural material such as a plant may be used. The essential oils, resinoids, balsams, absolutes, concretes, tinctures, and the like can be also prepared by known methods.

The deodorant composition of the invention is effective for elimination or reduction of a wide range of odors.

Specifically, it is effective for elimination or reduction of various odors including odors felt in daily life, such as bad breath (halitosis), body odor, odor in refrigerator, odor of feces and urine of human, animals, and birds, body odor, and odor of raw garbage, and malodors in factories and industrial wastes.

Moreover, the deodorant composition of the invention is excellent in the deodorizing effect on sulfur compounds such as methyl mercaptan, hydrogen sulfide, and dimethyl sulfide; nitrogenous compounds such as ammonia, urea, indole, skatole, and amines; and lower fatty acids such as butyric acid. Among them, the deodorant composition of the invention is particularly excellent in the deodorizing effect on sulfur compounds such as methyl mercaptan, hydrogen sulfide, and dimethyl sulfide.

Furthermore, the deodorant composition of the invention can be incorporated into the following products or goods to exhibit the deodorizing performance. Specifically, the products or goods include oral care products such as mouthwash, toothpaste, chewing gum, tablets, hard candy, soft candy, capsules, and oral spray; articles for pets and animals including dog, cat, rabbit, hamster, and parakeet, such as cat sand, cat sleeping straw, and sheet; detergents such as laundry detergents, kitchen detergents, bathroom detergents, carpet detergents, and toilet detergents; cosmetics such as soap, body shampoo, hand soap, lotion, skin toner, antiperspirant, foot deodorant spray, and foot powder; hair care products such as shampoo, conditioner, hair rinse, hair coloring agents, permanent-wave agents, wax, hair spray, and mousse; sanitary goods such as diapers, pads, sanitary napkins, sheets, towels, and wet tissues; household cleaning products, footwear cupboard spray, sheets in shoes, raw garbage spray, air cleaner and air conditioner, deodorizer, filters for air blower and air discharger, deodorants for refrigerator, deodorants for cloths, deodorant for drawers, closets, and ambry, room or car deodorants, toilet deodorants, deodorants for textile products, cloths (underwear and socks), car sheets, deodorant fibers, deodorants for factories and industrial wastes, and other various deodorants.

In the case that the deodorant composition of the invention is incorporated in the above products or goods, the amount is not unconditionally prescribed depending on the kind, applying environment, application, and use method of the products or goods but it is preferable to incorporate it usually in an amount of 0.001 to 100% by weight based on the products or goods.

At deodorization of malodor using the deodorant composition of the invention, a known method can be applied. For example, when a solid matter, gel matter, or liquid matter of the deodorant composition of the invention is applied by a method of directly spraying, sprinkling, wiping, immersing, or placing the composition to the site or place where a malodor component is present or the site or place where possible generation of a malodor component may be predicted, it is possible to eliminate the malodor or prevent the generation thereof. Moreover, the deodorant composition of the invention may be applied by a spraying method.

The present invention provides the deodorant composition exhibiting an excellent deodorizing effect on various malodor components. The deodorant composition of the invention is excellent in the deodorizing effect on malodor components such as sulfur compounds such as methyl mercaptan, hydrogen sulfide, and dimethyl sulfide and lower fatty acids such as butyric acid and isovaleric acid among malodor components, and also is excellent in the deodorizing effect on amine malodor components such as ammonia which are alkaline. Furthermore, the method for preparing the deodorant composition is relatively simple. Moreover, once the deodorant composition is prepared, it has an advantage that the deodorant performance is maintained even after the deodorant composition is stored for a long time. Therefore, the composition can be said to be a remarkably excellent deodorant composition.

EXAMPLES

The following will describe the invention more specifically with reference to Examples but the invention is by no means limited thereto.

Example 1

Preparation of Deodorant Composition

A deodorant composition was obtained by adding 1 mmol of each polyphenol described in Table 1 to the inside of a stirring vessel containing 50 mL of a 0.05M $Na_2CO_3$ solution (pH 11.2) and stirring the whole at 25° C. under conditions that air could freely flow and the surface of the reaction liquid could thoroughly come into contact with the air or allowing it to stand after the stirring under the same conditions. The stirring time and standing time are shown in Table 1.

Example 2

Deodorizing Effect on Methyl Mercaptan

Into a 50 mL vial were placed 2 mL of the deodorant composition of Example 1 and 4 μL of a 15% aqueous solution of methyl mercaptan (Tokyo Kasei Kogyo Co., Ltd.) and the vial was capped with Parafilm, followed by stirring at 25° C. After 10 minutes, 50 mL of the head space gas in the vial was passed through a gas detecting tube (manufactured by Gastech Corporation) to measure the concentration of sulfur compounds, which remained in the gas and were malodor components, and a deodorization rate was calculated according to the following expression. The results are shown in Table 1.

Deodorization rate (%)=100×{1−(A/B)}

In the above expression, A means the measured concentration of the malodor components and B means the concentration of the malodor components measured in the control.

The control was prepared by adding a 0.05M $Na_2CO_3$ solution (pH 11.2) instead of the addition of 2 mL of the deodorant composition of Example 1.

The time in the table shows a period of time from the start of stirring for the preparation of the deodorant composition to the end of the preparation of the deodorant composition. The 1 hour, 2 hours, and 3 hours mean the stirring time at the preparation of the deodorant composition. The deodorant compositions after 4 hours are compositions which have been allowed to stand after 3 hours of stirring. The same shall apply to the following tables except Table 18.

TABLE 1

| Polyphenols | 1 hour | 2 hours | 3 hours | 4 hours | 1 day | 5 days | 8 days |
|---|---|---|---|---|---|---|---|
| Pyrocatechol | 78.3 | 100.0 | 100.0 | 100.0 | 100.0 | 100.0 | 100.0 |
| Chlorogenic acid | 100.0 | 100.0 | 100.0 | 100.0 | 100.0 | 100.0 | 86.7 |
| (+)-Catechin | 25.0 | 66.7 | 83.3 | 91.7 | 100.0 | 100.0 | 63.3 |
| Quercetin | 100.0 | 100.0 | 100.0 | 100.0 | 100.0 | 85.0 | — |
| Gallic acid | 100.0 | 100.0 | 100.0 | 100.0 | 100.0 | 100.0 | 100.0 |

In the table, the numerals mean deodorization rates (%) and — means that the case is not measured (the same shall apply hereinafter).

Comparative Example 1

Preparation of Deodorant Composition Using Monophenol

A deodorant composition was obtained in the same manner as in Example 1 except that each monophenol described in Table 2 was used instead of the polyphenol described in Table 1.

Comparative Example 2

Deodorizing Effect of Deodorant Composition Using Monophenol on Methyl Mercaptan The deodorizing effect of the deodorant composition of Comparative Example 1 was measured in the same manner as in Example 2 except that 2 mL of each deodorant composition described in Comparative Example 1 was used instead of 2 mL of the deodorant composition of Example 1, and the deodorization rate was calculated. The results are shown in Table 2.

TABLE 2

| Monophenols | 1 hour | 2 hours | 3 hours | 4 hours | 1 day | 5 days |
|---|---|---|---|---|---|---|
| p-Coumaric acid | −8.3 | −8.3 | −8.3 | −8.3 | 0.0 | 0.0 |
| Ferulic acid | −8.3 | −8.3 | 0.0 | 0.0 | 13.3 | 20.0 |

In any of p-coumaric acid and ferulic acid, it was suggested that the deodorization rate was low and the yield efficiency of deodorizing effective components was extremely low.

Example 3

Preparation of Deodorant Composition

One mmol of chlorogenic acid was added to the inside of a stirring vessel containing 50 mL of a 0.05M $Na_2CO_3$ solution (pH 11.2) and the whole was stirred at 25° C. for 3 hours under conditions that air could freely flow and the surface of the reaction liquid could thoroughly come into contact with the air. Then, the reaction liquid was freeze-dried to obtain 460 mg of an ocher powdered deodorant composition.

Example 4

Deodorizing Effect on Methyl Mercaptan

The deodorizing effect of the deodorant composition of Example 3 was measured in the same manner as in Example 2 except that a solution obtained by dissolving 20 mg of the deodorant composition of Example 3 in 2 mL of water was used instead of 2 mL of the deodorant composition of Example 1. As a result, the deodorization rate was found to be 100%.

Comparative Example 3

Preparation of Deodorant Composition

A deodorant composition was obtained by adding 1 mmol of chlorogenic acid to the inside of a stirring vessel containing 50 mL of a 0.05M $Na_2CO_3$ solution (pH 11.2), from which dissolved oxygen had been removed by ultrasonification under vacuum with a vacuum pump, and stirring the whole at 25° C. under a nitrogen gas atmosphere or allowing it to stand after the stirring under the same conditions. The stirring time and standing time are shown in Table 3. The deodorant composition was yellow.

Comparative Example 4

Deodorizing Effect on Methyl Mercaptan

The deodorizing effect of the deodorant composition of Comparative Example 3 was measured in the same manner as in Example 2 except that 2 mL of the deodorant composition described in Comparative Example 3 was used instead of 2 mL of the deodorant composition of Example 1, and the deodorization rate was calculated. The results are shown in Table 3.

TABLE 3

|  | 1 hour | 2 hours | 3 hours | 7 hours | 24 hours |
|---|---|---|---|---|---|
| Deodorant composition of Comparative Example 3 | 16.7 | 8.3 | 8.3 | 8.3 | 8.3 |

In the case that the deodorant composition was prepared without supplying oxygen molecules, it was suggested that the deodorization rates in any reaction times were extremely low and the yield efficiency of a deodorizing effective component was extremely low.

Example 5

Preparation of Deodorant Composition

A deodorant composition was obtained by adding 1 mmol of each polyphenol described in Table 4 and 1 mmol of glycine to the inside of a reaction vessel containing 50 mL of a 0.05M $Na_2CO_3$ solution (pH 11.2) and stirring it at 25° C. under a condition that it can thoroughly come into contact with the air or allowing it to stand after the stirring under the same conditions. The stirring time and standing time are shown in Table 5.

The color tones of the resulting deodorant compositions (results on third day) are as shown in Table 4.

TABLE 4

| Polyphenols | Color tone of deodorant composition (reaction liquid) |
|---|---|
| Chlorogenic acid | Green |
| (+)-Catechin | Red |
| Protocatechuic acid | Red |
| Pyrocatechol | Pale pink |
| Aesculetin | Brown |
| Hydroquinone | Brown |
| Quercetin | Red |
| Gallic acid | Deep green |
| Tannic acid | Ocher |

Example 6

Deodorizing Effect on Methyl Mercaptan

The deodorizing effect of the deodorant composition of Example 5 was measured in the same manner as in Example 2 except that 2 mL of the deodorant composition described in Example 5 was used instead of 2 mL of the deodorant composition of Example 1, and the deodorization rate was calculated. The results are shown in Table 5.

TABLE 5

|  | 1 hour | 2 hours | 3 hours | 4 hours | 1 day | 3 days | 7 days | 15 days | 19 days | 27 days |
|---|---|---|---|---|---|---|---|---|---|---|
| A | 100.0 | 100.0 | 100.0 | 100.0 | 100.0 | 100.0 | 100.0 | 100.0 | 100.0 | 100.0 |
| B | 66.7 | 100.0 | 100.0 | 100.0 | 100.0 | 100.0 | 100.0 | 73.3 | 66.7 | 53.3 |
| C | 50.0 | — | 53.3 | 68.3 | — | 81.7 | 85.0 | — | 50.0 | 50.0 |
| D | 66.7 | 53.3 | 71.7 | 86.7 | — | 100.0 | 50.0 | — | 8.3 | 8.3 |
| E | 100.0 | 100.0 | 100.0 | 100.0 | 100.0 | 100.0 | 100.0 | 100.0 | 100.0 | 100.0 |
| F | 83.3 | 76.7 | 76.7 | — | 81.7 | — | — | — | — | 40.0 |
| G | 100.0 | 100.0 | 100.0 | 100.0 | 100.0 | 100.0 | 100.0 | 100.0 | 100.0 | 100.0 |
| H | 100.0 | 100.0 | 100.0 | 100.0 | 100.0 | 100.0 | 100.0 | 100.0 | 100.0 | 100.0 |
| I | 100.0 | 100.0 | 100.0 | 100.0 | 100.0 | 100.0 | 100.0 | 100.0 | 100.0 | 100.0 |

In the table, A means pyrocatechol, B means chlorogenic acid, C means protocatechuic acid, D means (+)-catechin, E means quercetin, F means aesculetin, G means gallic acid, H means hydroquinone, and I means tannic acid.

Comparative Example 5

Preparation of Deodorant Composition Using Monophenol

A deodorant composition was obtained in the same manner as in Example 5 except that 1 mmol of each monophenol described in Table 6 was used instead of 1 mmol of the polyphenol described in Table 4.

The color tones of the resulting deodorant compositions (results on third day) are as shown in Table 6.

TABLE 6

| Monophenols | Color tone of deodorant composition (reaction liquid) |
|---|---|
| p-Coumaric acid | None |
| Ferulic acid | Pale yellow |

Comparative Example 6

Deodorizing Effect of Deodorant Composition Using Monophenol on Methyl Mercaptan The deodorizing effect of the deodorant composition of Comparative Example 5 was measured in the same manner as in Example 2 except that 2 mL of each deodorant composition described in Comparative Example 5 was used instead of 2 mL of the deodorant composition of Example 1, and the deodorization rate was calculated.

The results are shown in Table 7.

TABLE 7

|  | 1 hour | 2 hours | 3 hours | 4 hours | 1 day | 3 days | 7 days | 15 days | 19 days | 27 days |
|---|---|---|---|---|---|---|---|---|---|---|
| p-Coumaric acid | 33.3 | 33.3 | 0.0 | 0.0 | 0.0 | 0.0 | 0.0 | 0.0 | 0.0 | 0.0 |
| Ferulic acid | 0.0 | 8.3 | 8.3 | 8.3 | 0.0 | 0.0 | 0.0 | 0.0 | 0.0 | 0.0 |

Example 7

Preparation of Deodorant Composition

A deodorant composition was obtained in the same manner as in Example 5 except that 1 mmol of chlorogenic acid and 1 mmol of each amino acid described in Table 8 were used.

The color tones of the resulting deodorant compositions are as shown in Table 8. Also, the pH of each reaction liquid and evaluation on the odor derived from each deodorizing material were described.

TABLE 8

| Amino acid | Color tone | pH | Material odor |
|---|---|---|---|
| Gly | Dark green | 9.3 | Slight odor |
| Ala | Dark green | 9.4 | Slight odor |
| Val | Dark green | 9.6 | Slight odor |
| Leu | Blackish green | 9.4 | Slight odor |
| Ile | Dark green | 9.4 | Slight odor |
| Glu | Dark green | 9.0 | Slight odor |
| Gln | Dark green | 9.2 | Slight odor |
| Asn | Dark green | 9.1 | Slight odor |
| Asp | Dark green | 8.7 | Slight odor |
| Lys | Dark green | 9.7 | Bean odor |
| Arg | Dark green | 9.8 | Slight odor |
| His | Dark green | 9.3 | No odor |
| Ser | Reddish brown | 9.2 | Almost no odor |
| Thr | Reddish brown | 9.2 | Slight odor |
| Met | Dark green | 9.2 | Odor |
| Cys-Cys | Dark green | 9.1 | Slight odor |
| Phe | Dark green | 9.3 | Odor |
| Tyr | Dark green | — | Almost no odor |
| Trp | Dark brown | — | Odor |
| Pro | Dark brown | — | Odor |
| Glu-Na | Dark green | — | Almost no odor |
| Asp-Na | Dark green | — | Almost no odor |

In the table, the color, pH, and odor show those of the reaction liquid after 3 days from the start of the reaction for the preparation of each deodorant composition.

Example 8

Deodorizing Effect on Methyl Mercaptan

The deodorization rate of each deodorant composition of Example 7 was measured in the same manner as in Example 2 except that 2 mL of each deodorant composition of Example 7 was used. The results are shown in Table 9.

TABLE 9

| Amino acid | 10 minutes | 30 minutes | 1 hour | 2 hours | 3 hours | 24 hours | 7 days | 132 days |
|---|---|---|---|---|---|---|---|---|
| Gly | 56.7 | 56.7 | 100.0 | 100.0 | 100.0 | 100.0 | 100.0 | 33.3 |
| Ala | 98.3 | 100.0 | 100.0 | 100.0 | 100.0 | 100.0 | 100.0 | 25.0 |
| Val | 100.0 | 100.0 | 100.0 | 100.0 | 100.0 | 100.0 | 100.0 | 0 |
| Leu | 100.0 | 100.0 | 100.0 | 100.0 | 100.0 | 100.0 | 100.0 | 0 |
| Ile | 98.3 | 100.0 | 100.0 | 100.0 | 100.0 | 100.0 | 100.0 | 0 |
| Glu | 97.5 | 98.3 | 100.0 | 100.0 | 100.0 | 100.0 | 100.0 | 50.0 |
| Gln | 46.7 | 50.0 | 66.7 | 83.3 | 91.7 | 100.0 | 100.0 | 0 |
| Asn | 41.7 | 66.7 | 73.3 | 90.0 | 100.0 | 100.0 | 100.0 | 8.3 |
| Asp | 16.7 | 16.7 | 36.7 | 65.0 | 68.3 | 68.3 | 75.0 | 25.0 |
| Lys | 100.0 | 100.0 | 100.0 | 100.0 | 100.0 | 100.0 | 100.0 | 50.0 |
| Arg | 100.0 | 100.0 | 100.0 | 100.0 | 100.0 | 100.0 | 100.0 | 33.3 |
| His | 68.3 | 85.0 | 91.7 | 100.0 | 100.0 | 100.0 | 100.0 | 33.3 |
| Ser | 65.7 | 81.7 | 91.7 | 100.0 | 100.0 | 100.0 | 100.0 | 8.3 |
| Thr | 65.0 | 81.7 | 91.7 | 100.0 | 100.0 | 100.0 | 100.0 | 0 |
| Met | 45.0 | 78.3 | 91.7 | 91.7 | 100.0 | 100.0 | 100.0 | 28.3 |
| Cys-Cys | 95.0 | 98.3 | 100.0 | 100.0 | 100.0 | 100.0 | 100.0 | 91.7 |
| Phe | 75.0 | 85.0 | 100.0 | 100.0 | 100.0 | 100.0 | 100.0 | 36.7 |
| Tyr | 65.0 | 56.7 | 78.3 | 86.7 | 96.7 | 100.0 | 100.0 | 53.3 |
| Trp | 53.3 | 36.7 | 75.0 | 91.7 | 100.0 | 100.0 | 100.0 | 33.3 |
| Pro | 100.0 | 100.0 | 100.0 | 100.0 | 100.0 | 100.0 | 100.0 | 0 |
| Glu-Na | — | — | 83.3 | 83.3 | 90.0 | 91.7 | 66.7 | 0 |
| Asp-Na | — | — | 98.3 | 98.3 | 100.0 | 100.0 | 66.7 | 0 |

Example 9

Preparation of Deodorant Composition

One mmol of chlorogenic acid and 1 mmol of glycine were placed in a reaction vessel and 50 mL of a 0.05M $Na_2CO_3$ solution (pH 11.2) was added thereto. The whole was stirred at 25° C. for 3 hours under a condition that it could come into contact with air. Then, the product was freeze-dried to obtain 535 mg of a dark green powdered deodorant composition.

Example 10

Deodorizing Effect on Methyl Mercaptan

The deodorization rate was measured in the same manner as in Example 2 except that 28 mg of the powdered deodorant composition of Example 9 was used instead of the deodorant composition of Example 1 and 2 mL of distilled water was further added.

As a result, the deodorization rate was found to be 100%.

Example 11

Preparation of Deodorant Composition

In a reaction vessel was placed 50 mL of a 0.05M $Na_2CO_3$ solution (pH 11.2), and then each plant extract (an extract containing a polyphenol and an amino acid) described in Table 10 was added thereto so that the polyphenol content becomes 1 mmol. The whole was stirred at 25° C. under a condition that it could come into contact with air or stirred under the same conditions and then allowed to stand to obtain a deodorant composition. The stirring time and the standing time are shown in Table 10.

Example 12

Deodorizing Effect on Methyl Mercaptan

The deodorization rate was measured in the same manner as in Example 2 using each deodorant composition of Example 11 was used. The results are shown in Table 10.

TABLE 10

|  | 1 hour | 3 hours | 24 hours | 4 days | 36 days |
| --- | --- | --- | --- | --- | --- |
| Coffee raw bean extract | 100.0 | 100.0 | 100.0 | 100.0 | 100.0 |
| Green tea extract | 100.0 | 100.0 | 100.0 | 100.0 | 100.0 |
| Apple extract | 100.0 | 100.0 | 100.0 | 100.0 | 100.0 |
| Rosemary extract | 100.0 | 100.0 | 100.0 | 100.0 | 100.0 |
| Peppermint extract | 100.0 | 100.0 | 100.0 | 100.0 | 100.0 |
| Spearmint extract | 100.0 | 100.0 | 100.0 | 100.0 | 100.0 |
| Grape pericarp extract | 100.0 | 100.0 | 100.0 | 100.0 | 100.0 |
| Grape seed extract | 100.0 | 100.0 | 100.0 | 100.0 | 100.0 |

Coffee raw bean extract: polyphenol content 45% by weight
Green tea extract: polyphenol content 30% by weight
Apple extract: polyphenol content 60% by weight
Rosemary extract: polyphenol content 50% by weight
Peppermint extract: polyphenol content 32% by weight
Spearmint extract: polyphenol content 33% by weight
Grape pericarp extract: polyphenol content 90% by weight
Grape seed extract: polyphenol content 40% by weight The polyphenol contents were calculated in terms of chlorogenic acid in the cases of the coffee raw bean extract, apple extract, rosemary extract, peppermint extract, and spearmint extract. In the case of the green tea extract, the content was calculated in terms of catechin. In the cases of the grape pericarp extract and grape seed extract, the contents were adopted following manufacturer's indications.

Preparation of Coffee Raw Bean Extract:
Coffee raw beans were extracted under stirring at 90 to 95° C. for 2 hours with adding 10 weight equivalents of water. After filtration, the filtrate was concentrated by removing the solvent under reduced pressure to obtain a coffee raw bean extract (yield based on coffee raw beans: about 16.8%).

Preparation of Green Tea Extract:
Green tea was extracted under stirring at 90 to 95° C. for 2 hours with adding 20 weight equivalents of water. After filtration, the filtrate was concentrated by removing the solvent under reduced pressure to obtain a green tea extract (yield based on green tea: about 25.7%).

Apple extract: manufactured by Nikka Whisky K.K.

Preparation of Rosemary Extract:
Dry rosemary was extracted under stirring at 45 to 50° C. for 2 hours with adding 20 weight equivalents of 30% hydrous ethanol. After filtration, the filtrate was concentrated by removing the solvent under reduced pressure to obtain a rosemary extract (yield based on dry rosemary: about 15.4%).

Preparation of Peppermint Extract:
Dry peppermint after oil components had been removed by steam distillation treatment was extracted under stirring at 90 to 95° C. for 2 hours with adding 10 weight equivalents of water. After filtration, the filtrate was concentrated by removing the solvent under reduced pressure to obtain a peppermint extract (yield based on dry peppermint: about 17.8%).

Preparation of Spearmint Extract:
Dry spearmint after oil components had been removed by steam distillation treatment was extracted under stirring at 90 to 95° C. for 2 hours with adding 10 weight equivalents of water. After filtration, the filtrate was concentrated by removing the solvent under reduced pressure to obtain a spearmint extract (yield based on dry spearmint: about 15.8%).

Grape pericarp extract: manufactured by Polyphenolics
Grape seed extract: manufactured by Polyphenolics

Example 13

Dried pericarp of apples (a variety of Fuji) was pulverized into powder by a mill to obtain an apple powder. To 80 g of the powder was added 800 mL of a 50 mM sodium carbonate solution, and the whole was vigorously stirred at 40° C. for 3 hours in a state that it could come into contact with air (the pH of the reaction solution was 7.6). After the reaction liquid was filtered, the filtrate was dried under reduced pressure to obtain 81.6 g of a deodorant composition powder (102% based on dried pericarp).

Example 14

To 80 g of dry tea leaves of green tea was added 1600 mL of a 50 mM sodium carbonate solution, and the whole was vigorously stirred at 30° C. for 1 hour in a state that it could come into contact with air (the pH of the reaction solution was 8.7). After the reaction liquid was filtered, the filtrate was freeze-dried under reduced pressure to obtain 51.8 g of a deodorant composition powder (64% based on dried tea leaves).

Example 15

A hundred grams of dried leaves and stems of *perilla* after oil parts had been removed by steam distillation treatment were pulverized by a mill. Thereto was added 20 weight equivalents of a 50 mM sodium carbonate solution (pH 11.2), and the whole was vigorously stirred and extracted at 25° C. for 3 hours in a state that it could come into contact with air (the pH of the reaction solution was 8.5). After the reaction liquid was filtered, the filtrate was freeze-dried to obtain 25.8 g of a deodorant composition powder (25.8% based on dried *perilla*).

Example 16

To 100 g of coffee raw beans was added 10 weight equivalents of a 50 mM sodium carbonate solution (pH 11.2), and the whole was vigorously stirred at 15° C. for 3 hours in a state that it could come into contact with air (the pH of the reaction solution was 7.8). After the reaction liquid was filtered, the filtrate was freeze-dried to obtain 17.3 g of a deodorant composition powder (17.3% based on coffee raw beans).

Example 17

To 100 g of dried pericarp of grapes was added 10 weight equivalents of a 50 mM sodium carbonate solution (pH 11.2), and the whole was vigorously stirred at 15° C. for 3 hours in a state that it could come into contact with air (the pH of the reaction solution was 7.3). After the reaction liquid was filtered, the filtrate was freeze-dried to obtain 15.4 g of a deodorant composition powder (15.4% based on dried pericarp of grapes).

Example 18

The deodorization rate was measured in the same manner as in Example 2 except that a solution obtained by dissolving 40 mg of each deodorant composition powder obtained in Examples 13 to 17 in 2 mL of water was used instead of the deodorant composition of Example 1. The results are shown in Table 11.

TABLE 11

| Deodorant composition | Color tone of solution | Deodorization rate |
|---|---|---|
| Example 13 (derived from apple pericarp) | red | 100% |
| Example 14 (derived from green tea) | red | 100% |
| Example 15 (derived from *perilla*) | red | 100% |
| Example 16 (derived from coffee raw bean) | green | 100% |
| Example 17 (derived from grape pericarp) | red | 100% |

Example 19 and Comparative Example 7

In a reaction vessel, 1 mmol of gallic acid, 1 mmol of sodium glutamate, and each of $Na_2CO_3$ aqueous solutions having various concentrations described in Table 12 or each of NaOH aqueous solutions having various concentrations described in Table 13 were mixed. The whole was stirred at room temperature under a condition that air could come into contact therewith or stirred under the same conditions and then allowed to stand to prepare a deodorant composition. The stirring time and the standing time were shown in Tables 12 and 13.

Using each of the above deodorant composition, the deodorization rate was measured in the same manner in Example 2. In the control corresponding to B in the expression of Example 2, each of alkaline solvents having various concentrations described in Tables 12 and 13 was added instead of the deodorant composition.

The results are shown in Tables 12 and 13.

TABLE 12

| $Na_2CO_3$ aqueous solution | 3 hours | 1 day | 3 days | 5 days | 20 days | 28 days | pH of reaction liquid during reaction | pH of alkaline solution before reaction |
|---|---|---|---|---|---|---|---|---|
| 1M | 100.0 | 100.0 | 100.0 | 100.0 | 100.0 | 100.0 | 10.7 | 11.6 |
| 500 mM | 100.0 | 100.0 | 100.0 | 100.0 | 100.0 | 100.0 | 10.6 | 11.5 |
| 100 mM | 100.0 | 100.0 | 100.0 | 100.0 | 100.0 | 100.0 | 9.9 | 11.4 |
| 50 mM | 100.0 | 100.0 | 100.0 | 100.0 | 100.0 | 100.0 | 9.0 | 11.4 |
| 25 mM | 100.0 | 100.0 | 100.0 | 100.0 | 85.0 | 56.7 | 8.0 | 11.4 |
| 10 mM | 0 | 0 | 25.0 | 25.0 | 36.7 | 16.7 | 6.0 | 11.1 |
| 1 mM | 0 | 0 | 0 | 0 | 0 | 0 | 4-5 | 10.9 |

TABLE 13

| NaOH aqueous solution | 3 hours | 1 day | 3 days | 5 days | 14 days | 21 days | pH of reaction liquid during reaction | pH of alkaline solution before reaction |
|---|---|---|---|---|---|---|---|---|
| 1M | 100.0 | 100.0 | 100.0 | 100.0 | 100.0 | 100.0 | 12.9 | 13.5 |
| 500 mM | 100.0 | 100.0 | 100.0 | 100.0 | 100.0 | 100.0 | 12.8 | 13.4 |
| 100 mM | 100.0 | 100.0 | 100.0 | 100.0 | 100.0 | 100.0 | 10.1 | 12.8 |
| 50 mM | 100.0 | 100.0 | 100.0 | 100.0 | 100.0 | 100.0 | 8.0 | 12.5 |
| 25 mM | 100.0 | 100.0 | 100.0 | 100.0 | 50.0 | 50.0 | 7.0 | 12.2 |
| 10 mM | 0 | 0 | 0 | 0 | 0 | 0 | 4.6 | 11.8 |
| 1 mM | 0 | 0 | 0 | 0 | 0 | 0 | 4.6 | 10.7 |

The pH of the reaction liquid was measured after 3 days from the start of the reaction (stirring).

In any alkaline solvents, the deodorant compositions prepared at pH of the reaction liquid of 6.5 or higher during the reaction exhibited an excellent deodorizing effect but the deodorant compositions prepared at pH of the reaction liquid of 6.0 or lower during the reaction exhibited a low deodorization rate.

Example 20 and Comparative Example 8

Preparation of Deodorant Compositions

To a reaction vessel in which 50 mL of the following alkaline solvent, alkaline buffer solvent, or neutral buffer solvent were added 1 mmol of chlorogenic acid and 1 mmol of glycine, and the whole was stirred at 25° C. or stirred at 25° C. and then allowed to stand, whereby a deodorant composition was obtained. The stirring time and the standing time are shown in Table 14.
(A) 0.05M $NaHCO_3$ solution (pH 8.3)
(B) 0.05M $NaHCO_3/Na_2CO_3$ solution (pH 9.1)
(C) 0.05M $NaHCO_3/Na_2CO_3$ solution (pH 10.0)
(D) 0.05M $Na_2CO_3$ solution (pH 11.2)
(E) 0.05M $Na_2HPO_4/NaH_2PO_4$ solution (pH 6.5)

Example 21

Deodorizing Effect on Methyl Mercaptan

Using each deodorant composition of Example 20, the deodorizing effect of Example 20 was measured in the same manner in Example 2. In the control corresponding to B in the expression of Example 2, each of (A) to (E) solvents was added instead of the deodorant composition.
The results are shown in Table 14.

TABLE 14

|     | 3 hours | 4 hours | 6 hours | 8 hours | 24 hours | pH of reaction liquid during reaction | pH of alkaline solution before reaction |
|-----|---------|---------|---------|---------|----------|---------------------------------------|-----------------------------------------|
| (A) | 16.7    | 25.0    | 75.0    | 83.3    | 83.3     | 6.5                                   | 8.3                                     |
| (B) | 33.3    | 71.7    | 100.0   | 100.0   | 100.0    | 9.0                                   | 9.1                                     |
| (C) | 50.0    | 81.7    | 100.0   | 100.0   | 100.0    | 10.0                                  | 10.0                                    |
| (D) | 91.4    | 100.0   | 100.0   | 100.0   | 100.0    | 9.3                                   | 11.2                                    |
| (E) | 0.0     | 0.0     | 0.0     | 0.0     | 0.0      | 6.5                                   | 6.5                                     |

In the tables, (A), (B), (C), (D), and (E) represent deodorant compositions prepared using a 0.05M $NaHCO_3$ solution (pH 8.3), a 0.05M $NaHCO_3/Na_2CO_3$ solution (pH 9.1), a 0.05M $NaHCO_3/Na_2CO_3$ solution (pH 10.0), a 0.05M $Na_2CO_3$ solution (pH 11.2), and a 0.05M $Na_2HPO_4/NaH_2PO_4$ solution (pH 6.5), respectively.

In the case that chlorogenic acid and glycine were added to the buffer solution of pH 6.5 and reacted, the pH of the reaction liquid during the reaction was maintained at pH 6.5 and no deodorizing effect was observed at any reaction times.

On the other hand, even when the pH of the reaction liquid during the reaction was 6.5, a deodorizing effect was observed and a deodorant composition was formed in the case that the solvent before the reaction was alkaline and the pH became 6.5 as a result of the reaction with the addition of chlorogenic acid and glycine.

From Examples 19, 20, and 21, it is suggested that the formation of the deodorant composition does not depend on the kind and concentration of the alkaline solvent and the pH of the alkaline solvent before the reaction but it is an important factor to make the pH of the reaction liquid during the reaction 6.5 or higher by using the alkaline solvent with the pH of 7.0 or higher.

Example 22

Influence of Oxygen Supplying Amount

One mmol of gallic acid and 1 mmol of sodium glutamate were added to the inside of the reaction vessel containing 100 mL of a 0.05M sodium carbonate solution (pH 11.2), and the whole was stirred at each temperature described in Table 15 with continuously supplying air and the concentration of dissolved oxygen in the reaction liquid was measured with time. Moreover, in the case of 100 mL of a 0.05M sodium carbonate solution (pH 11.2) without adding gallic acid and sodium glutamate, the concentration of dissolved oxygen in the reaction liquid was measured with time in the same manner. The results are shown in Table 15.

The concentration of dissolved oxygen in the reaction liquid was measured using a dissolved oxygen measuring apparatus (manufactured by TOA Electric K.K., oxygen electrode: OE-2102) at 23.4° C. and 42.4° C. and using a Ponal Kit for measuring dissolved oxygen (manufactured by Dojindo Laboratories) at 60° C. and 80° C., and in boiling water.

With regard to the case after 3 hours of stirring at each temperature, as in Example 2, a deodorizing activity test was conducted. The results are shown in Table 16.

TABLE 15

|                      | Solvent alone (stirring time) | | | (+)Gallic acid + Glu-Na (stirring time) | | |
|----------------------|--------|--------|--------|--------|--------|--------|
| Reaction temperature | 0 min  | 10 min | 3 hr   | 0 min  | 10 min | 3 hr   |
| 23.4° C.             | 3.7    | 7.8    | 7.8    | 0      | 0      | 0      |
| 42.4° C.             | 3.2    | 5.2    | 5.2    | 0      | 0      | 0      |
| 60.0° C.             | 2.5    | 2.0    | 2.0    | 0      | 0      | 0      |
| 80.0° C.             | 0.5    | 1.5    | 1.5    | 0      | 0      | 0      |
| Boiling temperature  | 0.5    | 0.5    | 0.5    | 0      | 0      | 0      |

Amount of Dissolved Oxygen in the Reaction Liquid (mg/L)

In the case of the solvent alone, at the measured temperatures except boiling temperature, the amount of dissolved oxygen reached equilibrium within 10 minutes of stirring but the amount decreased as the temperature was elevated. In the case that gallic acid and sodium glutamate were added and reacted, the amount of dissolved oxygen in the reaction liquid was 0 at any time. From these results, it is revealed that gallic acid and sodium glutamate rapidly consume dissolved oxygen when they are dissolved in an alkaline solvent and subsequently continue to consume it.

TABLE 16

| Reaction temperature | Deodorization rate at 3 hours stirring (%) |
|----------------------|--------------------------------------------|
| 23.4° C.             | 100                                        |
| 42.4° C.             | 100                                        |
| 60.0° C.             | 100                                        |
| 80.0° C.             | 100                                        |
| Boiling temperature  | 25                                         |

As a result of the deodorizing activity test at 3 hours of stirring with adding gallic acid and sodium glutamate, the deodorization rate was 100% in all cases at the reaction temperature other than boiling temperature but the deodorization rate was 25% in the case that the reaction was carried out at boiling temperature.

From the above results, it is suggested that the yield efficiency of the deodorizing effective component considerably decreases at the amount of dissolved oxygen in the case that the reaction was carried out at boiling temperature (0.5 mg/L).

Example 23

Measurement of Molecular Weight

One mmol of tannic acid and 1 mmol of sodium glutamate were added to the inside of a stirring vessel containing 50 mL of a 0.05M sodium carbonate solution (pH 11.2). The whole was stirred at 25° C. for 3 hours under a condition that it could come into contact with air and then allowed to stand to obtain a deodorant composition.

One mmol of gallic acid and 1 mmol of glycine were added to the inside of a stirring vessel containing 50 mL of a 0.05M sodium carbonate solution (pH 11.2). The whole was stirred at 25° C. for 3 hours under a condition that it could come into contact with air and then allowed to stand to obtain a deodorant composition.

Two grams of each resulting deodorant composition was subjected to centrifugal membrane filtration at 3,000 rpm for 1 hour. In the centrifugal membrane filtration, two kinds of filtration membranes were used, which were a filtration membrane whose separating molecular weight was 3,000 and a filtration membrane whose separating molecular weight was 10,000. In the filtration of separating molecular weight of 3,000, substances having a molecular weight of 3,000 or less were separated as the filtrate and substances having a molecular weight of more than 3,000 were separated as the filtration residue. In the filtration of separating molecular weight of 10,000, substances having a molecular weight of 10,000 or less were separated as the filtrate and substances having a molecular weight of more than 10,000 were separated as the filtration residue.

After the centrifugal membrane filtration, a deodorizing activity test was conducted on the filtrate and the filtration residue as in Example 2 to measure the deodorization rate. In this connection, the liquid obtained by dissolving the filtration residue in 2 g of water was referred to as a filtration residual liquid.

The results are shown in Table 17.

Filtration membrane for molecular weight 3,000 separation:
Centricon (registered trademark) YM-3 (manufactured by Millipore, for cutting molecular weight 3,000)
Filtration membrane for molecular weight 10,000 separation:
Centricon (registered trademark) YM-10 (manufactured by Millipore, for cutting molecular weight 10,000)

TABLE 17

|  | Filtration for cutting molecular weight 3,000 | Filtration for cutting molecular weight 10,000 |
|---|---|---|
| (Tannic acid × Glu-Na) | | |
| Filtration residual liquid | 100 | 0 |
| Filtrate | 100 | 100 |
| (Gallic acid × Gly) | | |
| Filtration residual liquid | 100 | 0 |
| Filtrate | 100 | 100 |

The numerals in the table mean deodorization rates (%).

The same results were obtained in the cases of both of the deodorant composition derived from tannic acid and sodium glutamate and the deodorant composition derived from gallic acid and glycine. Namely, in the case of the centrifugal filtration apparatus for cutting molecular weight of 3,000, a strong deodorizing activity was observed on both of the filtrate and the filtration residual liquid. However, in the case of the centrifugal filtration apparatus for cutting molecular weight of 10,000, a strong deodorizing activity was observed on the filtrate but no deodorizing effect was observed on the filtration residual liquid. Based on the results, it is suggested that the molecular weight of the active component in the deodorant composition should be 10,000 or less.

Example 24

Reaction Temperature and Reaction Time at Preparation of Deodorant Composition One mmol of gallic acid and 1 mmol of sodium glutamate were added to the inside of a reaction vessel containing 50 mL of a 0.05M sodium carbonate solution (pH 11.2). The whole was continued to stir at each temperature for each period of time described in Table 18 under a condition that it could come into contact with air. Two milliliters of the reaction liquid was sampled with time and the deodorizing activity was measured according to Example 2.

The results are shown in Table 18

TABLE 18

| Stirring time (Hr) | Reaction temperature | | | | | | |
|---|---|---|---|---|---|---|---|
|  | 5° C. | 25° C. | 40° C. | 50° C. | 60° C. | 70° C. | 80° C. |
| 0 | 100 | 100 | 100 | 100 | 100 | 100 | 100 |
| 1 | 100 | 100 | 100 | 100 | 100 | 100 | 100 |
| 2 | 100 | 100 | 100 | 100 | 100 | 100 | 100 |
| 3 | 100 | 100 | 100 | 100 | 100 | 100 | 100 |
| 4 | 100 | 100 | 100 | 100 | 100 | 100 | 55 |
| 5 | 100 | 100 | 100 | 100 | 100 | 100 | 0 |
| 6 | 100 | 100 | 100 | 100 | 100 | 100 | 0 |
| 7 | 100 | 100 | 100 | 100 | 100 | 55 | 0 |
| 8 | 100 | 80 | 75 | 75 | 25 | 0 | 0 |
| 9 | 100 | 70 | 63 | 63 | 0< | — | — |
| 24 | 70 | <10 | 0< | 0< | 0 | — | — |

The numerals in the table mean deodorization rates.
Moreover, — means no measurement.

With regard to the relation between the reaction (stifling) temperature and the deodorizing activity, it is revealed that the deodorizing activity decreases as the reaction temperature is elevated. Particularly at a high temperature of 70° C. or higher, the deodorizing activity decreased when the stirring time was a long time. Therefore, the reaction temperature at which the yield efficiency of the deodorizing effective component is high is in the range of up to 60° C. The reaction (stirring) time is preferably about 7 hours. Moreover, at the reaction temperature of 80° C., the time up to 3 hours is suitable for the formation of the deodorizing effective component, wherein the deodorization rate of 100% is maintained.

Example 25

Influence of Metal Ion

In a reaction vessel, 1 mmol of chlorogenic acid, 1 mmol of sodium glutamate, 50 mL of a 50 mM $Na_2CO_3$ aqueous solution, and 0.25 mmol of each of various metal salts described in Table 19 were mixed. The whole was stirred at room temperature under a condition that it could come into contact with air or stirred under the same conditions and then allowed to stand to prepare a deodorant composition. The stirring time and the standing time were shown in Table 19. Moreover, "no addition" in the table means a deodorant composition prepared without adding any metal salt.

Using the above deodorant composition, the deodorization rate was measured in the same manner in Example 2. The results are shown in Table 19.

TABLE 19

| Various metal salts | Deodorization rate after 3 hours (%) | Deodorization rate after 48 days (%) | pH | Color tone |
| --- | --- | --- | --- | --- |
| No addition | 100.0 | 45.0 | 7.8 | Dark green –> black green |
| $CaCl_2$ | 96.7 | 83.3 | 8.0 | Green –> black green |
| $MgCl_2$ | 100.0 | 100.0 | 8.1 | Dark green –> dark green |
| $CuCl_2$ | 100.0 | 100.0 | 8.5 | Dark green –> dark brown |
| $MnSO_4$ | 100.0 | 100.0 | 8.7 | Dark blue green –> dark blue green |
| $ZnCl_2$ | 100.0 | 100.0 | 8.5 | Dark green –> dark green |

The pH in the table was a result observed after 3 days from the start of the reaction (stirring). The color tone showed results observed after 3 days and 48 days from the start of the reaction (stirring).

In the case that a metal ion was added, durability of the deodorizing activity was observed as compared with the control (no addition of metal salt). Moreover, the deodorant compositions to which $MgCl_2$, $ZnCl_2$, or $MnSO_4$ was added also exhibited an excellent effect on the stability of the color tone.

Example 26

Influence of Concentration of Metal Ion

In a reaction vessel, 1 mmol of chlorogenic acid, 1 mmol of sodium glutamate, 45 mL of a 50 mM $Na_2CO_3$ aqueous solution, and 5 mL of each of various concentrations of an $MgCl_2$ aqueous solution described in Table 20 were mixed. The whole was stirred at room temperature under a condition that it could come into contact with air or stirred under the same conditions and then allowed to stand to prepare a deodorant composition. The stirring time and the standing time were shown in Table 20. Moreover, "no addition" in the table means a deodorant composition prepared without adding the $MgCl_2$ aqueous solution.

Using the above deodorant composition, the deodorization rate was measured in the same manner in Example 2. The results are shown in Table 20.

TABLE 20

| Concentration of $MgCl_2$ aqueous solution | 3 hours | 13 days | 47 days | pH |
| --- | --- | --- | --- | --- |
| No addition | 100.0 | 83.3 | 46.7 | 7.9 |
| 50 mM | 80.0 | 100.0 | 100.0 | 7.4 |
| 5 mM | 100.0 | 100.0 | 100.0 | 8.9 |
| 0.5 mM | 100.0 | 100.0 | 66.7 | 9.0 |
| 0.05 mM | 100.0 | 100.0 | 55.0 | 9.0 |
| 0.005 mM | 100.0 | 100.0 | 63.3 | 9.1 |
| 0.0005 mM | 100.0 | 100.0 | 63.3 | 9.1 |

The pH was measured after 3 days from the start of the reaction (stirring).

Even in the case that a 0.0005 mM $MgCl_2$ aqueous solution was added, the deodorization rates after 13 days and 47 days were higher than the case of no addition and hence durability of the activity was enhanced by the addition of $MgCl_2$.

Example 27

Deodorizing Effect on Each Malodor and Concentration of Deodorant Composition

One mmol of gallic acid and 1 mmol of sodium glutamate were added to the inside of a reaction vessel containing 50 mL of a 0.05M sodium carbonate solution (pH 11.2). The whole was stirred at 25° C. for 3 hours under a condition that it could come into contact with air. Then, the reaction liquid was freeze-dried to obtain a deodorant composition powder. The powder was dissolved in water to obtain a deodorant composition solution.

A deodorant composition solution having a deodorant composition concentration of 10.00 mg/mL was prepared and tests for the deodorizing effect of the deodorant composition solution on methyl mercaptan, ammonia, and isovaleric acid was conducted.

[Deodorization Test on Methyl Mercaptan]

The test was conducted in the same manner as in Example 2.

[Deodorization Test on Ammonia]

Into a 50 mL vial was placed 2 mL of the deodorant composition, and 5 μL of a 2.8% ammonia water was added thereto. Then, the vial was capped with Parafilm, followed by stirring at 25° C. for 10 minutes. Thereafter, 50 mL of the head space gas in the vial was passed through a gas detecting tube (manufactured by Gastech Corporation) to measure the concentration of the malodor component which remained in the gas, and a deodorization rate was calculated according to the expression shown in Example 2.

[Deodorization Test on Isovaleric Acid]

Into a 50 mL vial was placed 2 mL of the deodorant composition, and 40 μL of isovaleric acid was added thereto. Then, the vial was capped with Parafilm, followed by stirring at 25° C. for 10 minutes. Thereafter, 50 mL of the head space gas in the vial was passed through a gas detecting tube (manufactured by Gastech Corporation) to measure the concentration of the malodor component which remained in the gas, and a deodorization rate was calculated according to the expression shown in Example 2.

As a result, the deodorization rates for methyl mercaptan, ammonia, and isovaleric acid were found to be 100(%), 80(%), and 100(%), respectively.

From this fact, it was revealed that the deodorant composition of the invention provides an excellent deodorizing effect on methyl mercaptan, ammonia, and isovaleric acid and is a multipurpose deodorant composition capable of also providing an excellent deodorizing effect on malodor components exhibiting alkalinity.

Example 28

Deodorizing Effect on Methyl Mercaptan and Concentration of Deodorant Composition One mmol of gallic acid and 1 mmol of sodium glutamate were added to the inside of a reaction vessel containing 50 mL of a 0.05M sodium carbonate solution (pH 11.2). The whole was stirred at 25° C. for 3 hours under a condition that it could come into contact with air. Then, the reaction liquid was freeze-dried to obtain a deodorant composition powder. The powder was dissolved in water to obtain a deodorant composition solution having each concentration shown in Table 21.

The test for the deodorizing effect of the deodorant composition solution having each concentration on methyl mercaptan was conducted.

[Deodorization Test on Methyl Mercaptan]

The test was conducted in the same manner as in Example 2.

The results are shown in Table 21.

TABLE 21

| Deodorization rate (%) | |
| --- | --- |
| Concentration of deodorant composition (mg/ml) | Malodor component Methyl mercaptan |
| 10.00 | 100 |
| 5.00 | 100 |
| 2.50 | 100 |
| 1.25 | 100 |
| 0.63 | 100 |
| 0.31 | 100 |
| 0.15 | 63 |

With regard to the deodorizing effect on methyl mercaptan, the deodorization rate was 100% even when the concentration of the deodorant composition was 0.31 mg/mL and thus an excellent deodorizing effect was exhibited. Furthermore, the deodorizing effect was observed even at the concentration of 0.15 mg/mL.

Example 29

Deodorizing Effect on Isovaleric Acid and Concentration of Deodorant Composition One mmol of gallic acid and 1 mmol of sodium glutamate were added to the inside of a reaction vessel containing 50 mL of a 0.05M sodium carbonate solution (pH 11.2). The whole was stirred at 25° C. for 3 hours under a condition that it could come into contact with air. Then, the reaction liquid was freeze-dried to obtain a deodorant composition powder. The powder was dissolved in water to obtain a deodorant composition solution having each concentration shown in Table 22.

The test for the deodorizing effect of the deodorant composition solution having each concentration on isovaleric acid was conducted.

[Deodorization Test on Isovaleric Acid]

Into a 50 mL vial was placed 2 mL of the deodorant composition, and 40 μL of isovaleric acid was added thereto. Then, the vial was capped with Parafilm, followed by stirring at 25° C. for 10 minutes. Thereafter, 50 mL of the head space gas in the vial was passed through a gas detecting tube (manufactured by Gastech Corporation) to measure the concentration of the malodor component which remained in the gas, and a deodorization rate was calculated according to the expression shown in Example 2.

The results are shown in Table 22.

TABLE 22

| Deodorization rate (%) | |
| --- | --- |
| Concentration of deodorant composition (mg/ml) | Malodor component Isovaleric acid |
| 10.00 | 100 |
| 5.00 | 100 |
| 2.50 | 100 |
| 1.25 | 90 |

Example 30

Urine Odor Suppressing Effect

Twenty mmol of gallic acid, 20 mmol of sodium glutamate, and 1,000 mL of a 50M sodium carbonate solution were mixed and the whole was stirred at room temperature for 3 hours under a condition that it could come into contact with air. Thereafter, the reaction liquid was dried and concentrated by freeze drying. The dried product was grinded to obtain 9.6 g of a deodorant composition powder.

About ½ (10 g) of the urine absorber of a paper diaper (Lifely Urine Pad Supper: manufactured by Unicharm Corporation) was placed in a 500 mL paper cup and 0.5 g of the above deodorant composition powder was added onto top. Then, 100 mL of human urine was added and the cup was capped with a double structure of Saran-Wrap (trade name) and aluminum foil. Sensory evaluation for odor after standing at 34° C. for 3 hours, 6 hours, or 24 hours was conducted by four panelists. The evaluation was conducted on the following items in terms of score evaluation and evaluation results were shown as an average of scores of four panelists.

The case that the deodorant composition powder was not added was adopted as a blank. The results are shown in FIGS. 1 and 2.

[Evaluation Items and Evaluation Scores]

Deodorizing effect on urine odor;
1: nearly no urine odor is felt
2: slight urine odor is felt
3: a little bit urine odor is felt
4: a little urine odor is felt
5: considerable urine odor is felt
6: strong urine odor is felt
Overall odor intensity (odor intensity over the whole system including urine odor, odor of the urine absorber of the paper diaper itself, and the like);
0: no odor is felt
1: odor is slightly felt with effort
2: odor is felt without effort
3: odor is evidently felt
4: odor is strongly felt
5: odor is impatiently strongly felt Example 31

Urine Odor Suppressing Effect

Twenty mmol of gallic acid and 1,000 mL of a 50M sodium carbonate aqueous solution were mixed and the whole was stirred at room temperature for 3 hours under a condition that it could come into contact with air. Thereafter, the reaction liquid was dried and concentrated by freeze drying. The dried product was ground to obtain 5.8 g of a deodorant composition powder.

The application method to the paper diaper and sensory evaluation were conducted in the same manner as in Example 30. The results are shown in FIGS. 1 and 2.

From FIGS. 1 and 2, the paper diaper to which the deodorant composition of the invention had been added exhibited that the score obtained after 24 hours of standing were about the same as the score obtained after 3 hours and thus the generation of urine odor was remarkably suppressed and also the odor intensity over the whole system was weak, so that a strong deodorizing effect was attained.

Example 32

Mouthwash

One mmol of gallic acid and 1 mmol of sodium glutamate were added to the inside of a reaction vessel containing 50 mL of a 0.05M $Na_2CO_3$ solution (pH 11.2). The whole was stirred at 25° C. for 3 hours under a condition that it could come into contact with air. Then, the reaction liquid was freeze-dried and allowed to stand to obtain a deodorant composition powder. The components of the following formulation were mixed and a mouthwash was obtained in a usual manner.

TABLE 23

Composition of mouthwash

| Component | % by weight |
|---|---|
| Ethyl alcohol | 10.00 |
| Polyoxyethylene hydrogenated castor oil | 2.00 |
| Saccharin sodium | 0.02 |
| Glycerin | 10.00 |
| Sodium benzoate | 0.05 |
| Deodorant composition of the invention | 2.00 |
| Purified water | Balance |
| Total | 100.00 |

[Deodorization Test]

A garlic extract solution was prepared from 4 g of garlic and 1 L of water. Ten milliliters of the resulting garlic extract solution was injected into a 50 mL bottle, and 1 mL of the above mouthwash was further added thereto, followed by mixing. Subsequently, the whole was shaken at 34° C. for 3 minutes. Sensory evaluation was conducted on the resulting mixture by five expert panelists according to the following evaluation standard. The results were shown as an average of scores of five panelists.

The results are shown in Table 24.
[Evaluation Standard Scores]
1 point) no garlic odor is felt
2 points) garlic odor is slightly felt
3 points) garlic odor is felt to some extent
4 points) garlic odor is evidently slightly felt
5 points) garlic odor is strongly felt
6 points) garlic odor is intensely felt

TABLE 24

| | Evaluation average score |
|---|---|
| Mouthwash containing inventive product | 1.0 |
| Control | 6.0 |

In the table, the control shows the result at the time when a mouthwash prepared without adding the inventive product was used.

Example 33

Tooth Paste

One mmol of tannic acid and 1 mmol of glycine were added to the inside of a reaction vessel containing 50 mL of a 0.05M $Na_2CO_3$ solution (pH 11.2). The whole was stirred at 25° C. for 3 hours under a condition that it could come into contact with air. Then, the reaction liquid was concentrated to dryness under reduced pressure to obtain a deodorant composition powder. The components of the following formulation were mixed and a tooth paste was obtained in a usual manner.

TABLE 25

Composition of tooth paste

| Component | % by weight |
|---|---|
| Dicalcium phosphate | 10.00 |
| Sodium lauryl sulfate | 2.00 |
| Carboxymethyl cellulose sodium | 0.50 |
| Saccharin sodium | 0.02 |
| Sodium benzoate | 10.00 |
| Deodorant composition of the invention | 0.10 |
| Glycerin | Balance |
| Total | 100.00 |

[Deodorization Test]

In order to evaluate the effect of eliminating bad breath in the case that the deodorant composition was used in the tooth paste, the following method was adopted.

After mouths were well rinsed with water, test subjects kept 10 mL of a 50 ppm solution of sodium methyl mercaptan in their mouths for 1 minute and then spat out the solution. Immediately, a breath was trapped into a 5 L plastic bag. Subsequently, they cleaned their teeth for 2 minutes with the tooth paste prepared in the above. Immediately, a breath was trapped into a 5 L plastic bag.

The breath after tooth cleaning in the plastic bag was subjected to sensory evaluation by four panelists based on the following evaluation standard in comparison with the breath before tooth cleaning in the plastic bag. The results are shown in Table 26 as an average of scores of the four panelists.
[Evaluation Standard Scores]
1 point) no methyl mercaptan is felt
2 points) methyl mercaptan is slightly felt
3 points) methyl mercaptan is felt to some extent
4 points) methyl mercaptan is evidently slightly felt
5 points) methyl mercaptan is strongly felt
6 points) methyl mercaptan is intensely felt

TABLE 26

| | Evaluation average score |
|---|---|
| Tooth paste containing inventive product | 1.0 |
| Control (1) | 6.0 |
| Control (2) | 4.5 |

In the table, the control (1) shows the case of the breath from the subjects who did not clean their teeth and the control (2) shows the case that a tooth paste prepared without adding the inventive product is used.

Example 34

Tablet

In a reaction vessel was placed 50 mL of a 0.05M $Na_2CO_3$ solution (pH 11.2), and a peppermint extract was added thereto so that the polyphenol content became 1 mmol in terms of chlorogenic acid. The whole was stirred at 25° C. for 3 hours under a condition that it could come into contact with air. Then, the reaction liquid was freeze-dried to obtain a deodorant composition powder. The components of the following formulation were mixed and a tablet was obtained in a usual manner.

TABLE 27

Composition of tablet

| Component | % by weight |
|---|---|
| Starch | 97.5 |
| Sucrose fatty acid ester | 0.5 |
| Deodorant composition of the invention | 2.0 |
| Total | 100.00 |

[Deodorization Test]

In order to evaluate the effect of eliminating bad breath in the case that the deodorant composition was incorporated into the tablet, the following method was adopted.

After mouths were well rinsed with water, test subjects kept 10 mL of a 50 ppm solution of sodium methyl mercaptan in their mouths for 1 minute and then spat out the solution. Immediately, a breath was trapped into a 5 L plastic bag. Subsequently, they ate the tablet prepared in the above for 10 minutes. Immediately, a breath was trapped into a 5 L plastic bag.

The breath after tablet eating trapped in the plastic bag was subjected to sensory evaluation by four panelists based on the same evaluation standard as in the case of the tooth paste in comparison with the breath before tablet eating trapped in the plastic bag. The results are shown in Table 28 as an average of scores of the four panelists.

TABLE 28

| | Evaluation average score |
|---|---|
| Tablet containing inventive composition | 1.3 |
| Control (1) | 6.0 |
| Control (2) | 4.8 |

In the table, the control (1) shows the case of the breath from the subjects who did not eat the tablet and the control (2) shows the case that a tablet prepared without adding the inventive product is used.

Example 35

Chewing Gum

In a reaction vessel was placed 50 mL of a 0.05M $Na_2CO_3$ solution (pH 11.2), and a grape pericarp extract was added thereto so that the polyphenol content became 1 mmol in terms of catechin. The whole was stirred at 25° C. for 3 hours under a condition that it could come into contact with air. Then, the reaction liquid was freeze-dried to obtain a deodorant composition powder. The components of the following formulation were mixed and a chewing gum was obtained in a usual manner.

TABLE 29

Composition of chewing gum

| Component | % by weight |
|---|---|
| Gum base | 21.0 |
| Sugar powder | 63.9 |
| Corn starch | 12.5 |
| Acidifying agent | 0.6 |
| Deodorant composition of the invention | 2.0 |
| Total | 100.0 |

[Deodorization Test]

In order to evaluate the effect of eliminating bad breath in the case that a chewing gum containing the above deodorant composition was used, the following method was adopted.

After mouths were well rinsed with water, test subjects kept 10 mL of a 50 ppm solution of sodium methyl mercaptan in their mouths for 1 minute and then spat out the solution. Immediately, a breath was trapped into a 5 L plastic bag.

Subsequently, they continued to chew the chewing gum prepared in the above for 10 minutes. Immediately, a breath was trapped into a 5 L plastic bag.

The breath after continued chewing of the gum trapped in the plastic bag was subjected to sensory evaluation by four panelists based on the same evaluation standard as in the case of the tooth paste in comparison with the breath before chewing of the gum trapped in the plastic bag. The results are shown in Table 30 as an average of scores of the four panelists.

TABLE 30

| | Evaluation average score |
|---|---|
| Inventive product | 1.3 |
| Control (1) | 6.0 |
| Control (2) | 4.3 |

In the table, the control (1) shows the case of the breath from the subjects who did not chew the gum and the control (2) shows the case that a chewing gum prepared without adding the inventive product is chewed.

Example 36

Antiperspirant

One mmol of chlorogenic acid and 1 mmol of sodium glutamate were added to the inside of a reaction vessel containing 50 mL of a 0.05M $Na_2CO_3$ solution (pH 11.2). The whole was stirred at 25° C. for 3 hours under a condition that it could come into contact with air. Then, the reaction liquid was freeze-dried to obtain a deodorant composition powder. A predetermined amount of the components of the following formulation was heated to obtain a homogeneous highly viscous solution. Then, the solution was cast into a mold and cooled to obtain an antiperspirant stick containing the deodorant composition.

TABLE 31

Composition of antiperspirant stick

| Component | % by weight |
|---|---|
| PEG-7 glyceryl cocoate | 2.0 |
| Hydrogenated oil | 5.0 |
| Mirystyl myristate | 15.0 |
| Cyclomethicone | 33.0 |
| Stearyl alcohol | 20.0 |
| Stearyl isononenoate | 3.0 |
| aluminum chlorohydrate | 20.0 |
| Deodorant composition of the invention | 2.0 |
| Total | 100.0 |

[Deodorization Test]

To 5 mL of a 0.25% butyric acid aqueous solution was added 2 g of shavings of the above antiperspirant stick, and the whole was mixed at room temperature. After 10 minutes, the mixture was subjected to sensory evaluation by five expert panelists based on the following evaluation standard. The results are shown as an average of scores of the five panelists in Table 32.

For comparison, using an antiperspirant stick containing no deodorant composition, sensory evaluation was conducted in the same manner as above.

[Evaluation Standard Score]
1 point) no butyric acid odor is felt
2 points) butyric acid odor is slightly felt
3 points) butyric acid odor is felt to some extent
4 points) butyric acid odor is evidently slightly felt
5 points) butyric acid odor is strongly felt
6 points) butyric acid odor is intensely felt

TABLE 32

| | Evaluation average score |
|---|---|
| Antiperspirant containing inventive product | 1.6 |
| Control | 6.0 |

In the table, the control shows the case of the antiperspirant containing no inventive product.

Example 37

Powdery Detergent

One mmol of gallic acid was added to the inside of a reaction vessel containing 50 mL of a 0.05M $Na_2CO_3$ solution (pH 11.2). The whole was stirred at 25° C. for 3 hours under a condition that it could come into contact with air. Then, the reaction liquid was freeze-dried to obtain a deodorant composition powder. The components of the following formulation were mixed and a powdery detergent was obtained in a usual manner.

TABLE 33

Composition of powdery detergent

| Component | % by weight |
|---|---|
| Sodium lauryl sulfate, Sodium stearyl sulfate | 15.0 |
| Sodium carbonate | 15.0 |
| Sodium metasilicate | 13.0 |
| Sodium citrate | 15.0 |
| Carboxymethyl cellulose | 2.0 |
| Sodium sulfate | 38.0 |
| Deodorant composition of the invention | 2.0 |
| Total | 100.0 |

[Deodorization Test]
One of socks worn for a whole day was immersed in water containing the powdery detergent (0.5% by weight) containing the deodorant composition prepared in the above, and it was washed at room temperature for 5 minutes and rinsed. The remaining one of the socks was immersed in water containing a powdery detergent (0.5% by weight) prepared without adding the deodorant composition of the invention, and it was washed at room temperature for 5 minutes at the same time and rinsed (control). The socks were subjected to sensory evaluation by five expert panelists according to the following evaluation standard. The results are shown as an average of scores of the five panelists in Table 34.

[Evaluation Standard Score]
1 point) no typical stuffy odor is felt
2 points) typical stuffy odor is slightly felt
3 points) typical stuffy odor is felt to some extent
4 points) typical stuffy odor is evidently slightly felt
5 points) typical stuffy odor is strongly felt
6 points) typical stuffy odor is intensely felt

TABLE 34

| | Evaluation average score |
|---|---|
| Powdery detergent containing inventive product | 1.2 |
| Control | 4.2 |

Example 38

Shampoo

One mmol of gallic acid and 1 mmol of sodium glutamate were added to the inside of a reaction vessel containing 50 mL of a 0.05M $Na_2CO_3$ solution (pH 11.2). The whole was stirred at 25° C. for 3 hours under a condition that it could come into contact with air. Then, the reaction liquid was freeze-dried to obtain a deodorant composition powder. The components of the following formulation were mixed and a shampoo was obtained in a usual manner.

TABLE 35

Composition of shampoo

| Component | % by weight |
|---|---|
| Sodium lauryl sulfate | 40.00 |
| Sodium cocoamphoacetate | 10.00 |
| Cocoamide DEA | 2.00 |
| Butylene glycol | 2.00 |
| Citric acid | 0.35 |
| Sodium chloride | 0.10 |
| Methylparaben | 0.20 |
| Propylparaben | 0.10 |
| EDTA tetrasodium | 0.10 |
| Green floral fragrance | 0.50 |
| Deodorant composition of the invention | 2.00 |
| Purified water | Balance |
| Total | 100.00 |

[Deodorization Test]
In order to evaluate the effect of eliminating permanent wave odor using the shampoo containing the deodorant composition, the following method was adopted.

A tress of false hair for test (1.8 g) was immersed in 50 mL of a permanent wave first solution (obtained by adjusting a 6% thioglycolic acid aqueous solution to pH 9.3 with ammonia water) for 30 minutes. After the attached first solution was wiped off with paper, the tress was washed with 100 mL of water and then immersed in 50 mL of a permanent wave second solution (5% potassium bromate aqueous solution) for 20 minutes. After the attached second solution was wiped off with paper, the tress was immersed in 1000 mL of water containing the shampoo (1% by weight) prepared in the above for 5 minutes. After the attached water containing the shampoo was wiped off with paper, the tress was washed with 100 mL of water and then the attached water was wiped off with paper. The tress was subjected to sensory evaluation by four panelists according to the following evaluation standard. The results are shown as an average of scores of the four panelists in Table 36.

[Evaluation Standard Score]
1 point) no permanent wave odor is felt
2 points) permanent wave odor is slightly felt
3 points) permanent wave odor is felt to some extent
4 points) permanent wave odor is evidently slightly felt
5 points) permanent wave odor is strongly felt
6 points) permanent wave odor is intensely felt

TABLE 36

|  | Evaluation average score |
| --- | --- |
| Shampoo containing inventive product | 1.5 |
| Control | 5.3 |

In the table, the control shows the case that a shampoo prepared without adding the inventive product is used.

Example 39

Deodorizing Effect on Human Feces and Urine

One mmol of chlorogenic acid was added to the inside of a reaction vessel containing 50 mL of a 0.05M sodium carbonate solution (pH 11.2). The whole was stirred at 25° C. for 3 hours under a condition that it could come into contact with air. Then, the reaction liquid was freeze-dried to obtain a deodorant composition powder.

[Deodorization Test]

Into a 100 mL vial were placed 10 mL of urine of an adult male and 20 mg of the above deodorant composition, and then the vial was capped with Parafilm (manufactured by American National Can), followed by shaking at 25° C. for 10 minutes. Moreover, into a 100 mL vial were placed 10 mL of urine of an adult male, 20 mg of the above deodorant composition, and 10 µL of lavender fragrance (manufactured by Takasago International Corporation), and then the vial was capped with Parafilm, followed by shaking at 25° C. for 10 minutes.

The inside of the vial was subjected to sensory evaluation by seven panelists according to the following evaluation standard. The results are shown as an average of scores of the seven panelists in Table 37.

As comparison, an analyte of the urine alone and an analyte wherein 10 µL of lavender fragrance (manufactured by Takasago International Corporation) was added to the urine were also tested.

[Sensory Evaluation Standard]
1 point) no malodor is felt
2 points) malodor is slightly felt
3 points) malodor is felt to some extent
4 points) malodor is evidently slightly felt
5 points) malodor is strongly felt
6 points) malodor is intensely felt

TABLE 37

|  | Evaluation average score |
| --- | --- |
| Urine + inventive product | 1.3 |
| Urine + inventive product + lavender fragrance | 1.0 |
| Urine alone | 6.0 |
| Urine + lavender fragrance | 4.7 |

Example 40

Deodorizing Effect on Physiological Odor

One mmol of tannic acid and 1 mmol of sodium glutamate were added to the inside of a reaction vessel containing 50 mL of a 0.05M $Na_2CO_3$ solution (pH 11.2). The whole was stirred at 25° C. for 3 hours under a condition that it could come into contact with air. Then, the reaction liquid was freeze-dried to obtain a deodorant composition powder.

[Deodorization Test]

Into a 100 mL vial were placed 10 mL of a physiological malodor and 50 mg of the above deodorant composition, and then the vial was capped with Parafilm, followed by shaking at 25° C. for 10 minutes. Then, sensory evaluation was conducted by seven panelists according to the following evaluation standard. The results are shown as an average of scores of the seven panelists in Table 38.

As comparison, an analyte of the malodor alone was shaken and subjected to sensory evaluation.

[Sensory Evaluation Standard]
1 point) no malodor is felt
2 points) malodor is slightly felt
3 points) malodor is felt to some extent
4 points) malodor is evidently slightly felt
5 points) malodor is strongly felt
6 points) malodor is intensely felt

TABLE 38

|  | Evaluation average score |
| --- | --- |
| Case that inventive product is added | 1.4 |
| Malodor alone | 6.0 |

Example 41

Deodorizing Effect on Feces and Urine of Livestock

One mmol of chlorogenic acid and 1 mmol of sodium glutamate were added to the inside of a reaction vessel containing 50 mL of a 0.05M $Na_2CO_3$ solution (pH 11.2). The whole was stirred at 25° C. for 3 hours under a condition that it could come into contact with air, and then allowed to stand to obtain a deodorant composition.

[Deodorization Test]

Into a 100 mL vial were placed 10 mL of a liquid separated from feces and urine of livestock and 1 mL of the above deodorant composition, and then the vial was capped with Parafilm, followed by shaking at 25° C. for 10 minutes. Then, sensory evaluation was conducted by seven panelists according to the following evaluation standard. The results are shown as an average of scores of the seven panelists in Table 39.

As control, an analyte obtained by culturing the feces and urine of livestock alone was used.

[Sensory Evaluation Standard]
1 point) no feces and urine odor is felt
2 points) feces and urine odor is slightly felt
3 points) feces and urine odor is felt to some extent
4 points) feces and urine odor is evidently slightly felt
5 points) feces and urine odor is strongly felt
6 points) feces and urine odor is intensely felt

TABLE 39

|  | Evaluation average score |
| --- | --- |
| Case that inventive product is added | 1.3 |
| Separated liquid of feces and urine of livestock alone | 6.0 |

Example 42

Deodorizing Effect on Fish Odor

In a reaction vessel was placed 50 mL of a 0.05M $Na_2CO_3$ solution (pH 11.2), and a green tea extract was added thereto so that the polyphenol content became 1 mmol in terms of catechin. The whole was stirred at 25° C. for 3 hours under a condition that it could come into contact with air and then allowed to stand to obtain a deodorant composition.

[Deodorization Test]

To 5 L of water was added 5 mL of the deodorant composition prepared in the above, and the whole was thoroughly mixed. In the mixture, a pan after sardine had been cooked was immersed. Under room temperature, after 10 minutes had been passed, the pan was taken out and the solution containing the deodorant composition was washed away with water. Then, the presence of odor on the pan surface and the degree thereof were evaluated in a sensory manner by five expert panelists based on the following evaluation standard. The results are shown as an average of scores of the five panelists in Table 40.

[Evaluation Standard Score]
1 point) no fish odor is felt
2 points) fish odor is slightly felt
3 points) fish odor is felt to some extent
4 points) fish odor is evidently slightly felt
5 points) fish odor is strongly felt
6 points) fish odor is intensely felt

TABLE 40

|  | Evaluation average score |
| --- | --- |
| Case that inventive product is added | 1.4 |
| Control | 6.0 |

In the table, the control shows the result of the test without adding the deodorant composition of the invention.

Example 43

Deodorizing Effect on Raw Garbage

One mmol of tannic acid was added to the inside of a reaction vessel containing 50 mL of a 0.05M $Na_2CO_3$ solution (pH 11.2). The whole was stirred at 25° C. for 3 hours under a condition that it could come into contact with air and then allowed to stand to obtain a deodorant composition.

[Deodorization Test]

One kilograms of so-called raw garbage composed of vegetable garbage, fish garbage, meat garbage, and the like was placed in a plastic bucket fitted with a cap and 50 mL of an aqueous solution obtained by ten times dilution of the deodorant composition prepared in the above with water was sprayed thereonto, followed by capping the bucket. As a control, 50 mL of water was sprayed onto 1 kg of the same raw garbage. After 3 days standing at room temperature, sensory evaluation was conducted by five panelists according to the predetermined evaluation standard. The results are shown as an average of scores of the five panelists in Table 41.

[Sensory Evaluation Standard]
1 point) no raw garbage odor is felt
2 points) raw garbage odor is slightly felt
3 points) raw garbage odor is felt to some extent
4 points) raw garbage odor is evidently slightly felt
5 points) raw garbage odor is strongly felt
6 points) raw garbage odor is intensely felt

TABLE 41

|  | Evaluation average score | Comment |
| --- | --- | --- |
| Inventive product | 2.4 | Odor intrinsic to vegetable and the like was observed but putrid odor characteristic to raw garbage was hardly observed. |
| Control | 5.8 | Intense putrid odor characteristic to raw garbage was observed. |

Example 44

Deodorizing Effect in Toilet

In a reaction vessel was placed 50 mL of a 0.05M $Na_2CO_3$ solution (pH 11.2), and an apple pericarp extract was added thereto so that the polyphenol content became 1 mmol in terms of chlorogenic acid. The whole was stirred at 25° C. for 3 hours under a condition that it could come into contact with air. Then, the reaction liquid was freeze-dried to obtain a deodorant composition powder.

[Deodorization Test]

Two grams of the inventive product was spread on the water sump of a toilet bowl and then feces were eliminated by five panelists. After the elimination, the odor in the toilet was evaluated in a sensory manner according to the sensory evaluation standard. The results are shown in Table 42.

[Sensory Evaluation Standard]
1 point) no excrement odor is felt
2 points) excrement odor is slightly felt
3 points) excrement odor is felt to some extent
4 points) excrement odor is evidently slightly felt
5 points) excrement odor is strongly felt to the same degree as in the usual case.

TABLE 42

|  | Evaluation average score | Comment |
| --- | --- | --- |
| Inventive product | 1.4 | Excrement odor was hardly felt and excrement odor was remarkably suppressed as compared with the usual case using no inventive product. |

Example 45

Deodorizing Effect on Malodor Gas

One mmol of gallic acid and 1 mmol of glycine were added to the inside of a reaction vessel containing 50 mL of a 0.05M $Na_2CO_3$ solution (pH 11.2). The whole was stirred at 25° C. for 3 hours under a condition that it could come into contact with air and then allowed to stand to obtain a deodorant composition.

[Deodorization Test]

Into a 4 L odorless bag, 4 L of air was included by means of an air pump. Each malodor gas (ammonia, trimethylamine, hydrogen sulfide, or methyl mercaptan) was injected thereinto by an injection syringe to regulate a gas concentration. The bag was set at a test apparatus of closed circulation system fitted with an air pump and the air pump was worked at an air amount of about 1000 mL/minute. One milliliter of the above deodorant composition was supported on an absorbent cotton (0.2 g) and the cotton was set at the discharging side of the air pump. After 2 hours of working, the remaining amount of the malodor gas in the system was measured using a dedicated gas detecting tube (Gastech Corporation) and a deodorization rate was calculated according to the following expression.

As a comparative example, an absorbent cotton impregnated with 1 mL of a 20 mM aqueous solution of gallic acid was set at the discharging side of the air pump, instead of the absorbent cotton on which the above deodorant composition was supported. Then, the test was conducted similarly and the deodorization rate was calculated.

The results are shown in Table 43.

$$\text{Deodorization rate (\%)}=100\times\{1-(A/B)\}$$

In the above expression, A means the measured concentration of the malodor components and B means the concentration of the malodor components measured in the control. The control is the case that an absorbent cotton was impregnated with 1 mL of water instead of 1 mL of the above deodorant composition.

TABLE 43

| Malodor gas | Initial concentration (ppm) | Deodorization rate (%) | |
| --- | --- | --- | --- |
| | | Deodorant composition of the invention | Gallic acid aqueous solution |
| Ammonia | 60 | 100.0 | 85.0 |
| Trimethylamine | 130 | 90.0 | 70.0 |
| Methyl mercaptan | 100 | 95.0 | 0 |
| Hydrogen sulfide | 120 | 100.0 | 5.0 |

The deodorant composition of the invention exhibits the deodorizing effect on various malodor components including amine malodor components such as ammonia and trimethylamine, sulfur compounds such as methyl mercaptan and hydrogen sulfide, and the like.

Industrial Applicability

The deodorant composition of the invention is effective for elimination or reduction of a wide range of odors. Specifically, it is effective for elimination or reduction of various odors including odors felt in daily life, such as bad breath (halitosis), body odor, odor in refrigerator, odor of feces and urine of human, animals, and birds, body odor, and odor of raw garbage, and malodors in factories and industrial wastes.

Moreover, the deodorant composition of the invention is excellent in the deodorizing effect on sulfur compounds such as methyl mercaptan, hydrogen sulfide, and dimethyl sulfide; nitrogenous compounds such as ammonia, urea, indole, skatole, and amines; and lower fatty acids such as butyric acid. Among them, the deodorant composition of the invention is particularly excellent in the deodorizing effect on sulfur compounds such as methyl mercaptan, hydrogen sulfide, and dimethyl sulfide.

Furthermore, the deodorant composition of the invention can be incorporated into the following products or goods to exhibit the deodorizing performance. Specifically, the products or goods include oral care products such as mouthwash, toothpaste, chewing gum, tablets, hard candy, soft candy, capsules, and oral spray; articles for pets and animals including dog, cat, rabbit, hamster, and parakeet, such as cat sand, cat sleeping straw, and sheet; detergents such as laundry detergents, kitchen detergents, bathroom detergents, carpet detergents, and toilet detergents; cosmetics such as soap, body shampoo, hand soap, lotion, skin toner, antiperspirant, foot deodorant spray, and foot powder; hair care products such as shampoo, conditioner, hair rinse, hair coloring agents, permanent-wave agents, wax, hair spray, and mousse; sanitary goods such as diapers, pads, sanitary napkins, sheets, towels, and wet tissues; household cleaning products, footwear cupboard spray, sheets in shoes, raw garbage spray, air cleaner and air conditioner, deodorizer, filters for air blower and air discharger, deodorants for refrigerator, deodorants for cloths, deodorant for drawers, closets, and ambry, room or car deodorants, toilet deodorants, deodorants for textile products, cloths (underwear and socks), car sheets, deodorant fibers, deodorants for factories and industrial wastes, and other various deodorants.

BRIEF DESCRIPTION OF DRAWINGS

FIG. 1 is a drawing illustrating a deodorizing effect of the deodorant composition of the invention on a paper diaper.

FIG. 2 is a drawing illustrating a deodorizing effect of the deodorant composition of the invention on a paper diaper, the effect being different from the above.

The invention claimed is:

1. A deodorant composition comprising, as an active component, a colored compound obtained by reacting a plant extract and/or a plant body containing a polyphenol and an amino acid in a solvent showing alkalinity in the coexistence of oxygen molecules at a reaction pH value of 6.5 or more,
wherein the plan extract and/or the plant body is selected from the group consisting of coffee raw bean, green tea, apple, rosemary, peppermint, spearmint, grape pericarp, grape seed and leaves and the stem of perilla;
the polyphenol is selected from the group consisting of chlorogenic acid, (+)-catechin, protocatechuic acid, pyrocatechol, aesculetin, hydroquinone, quercetin, gallic acid and tannic acid, and
the amino acid is selected from the group consisting of glycine, alanine, valine, leucine, isoleucine, glutamic acid, glutamine, asparagine, aspartic acid, lysine, arginine, histidine, serine, threonine, methionine, cystine, phenylalanine, tyrosine, tryptophan, proline, sodium glutamate and sodium aspartate.

2. The deodorant composition according to claim 1, wherein the concentration of oxygen molecule during the reaction is 1 mg/L or more.

3. The deodorant composition according to claim 1, wherein the reacting is conducted at a temperature in the range of 0 to 60° C.

4. The deodorant composition according to claim 1, wherein the reacting is conducted in the presence of an added metal ion.

* * * * *